(12) United States Patent
Kirihara et al.

(10) Patent No.: US 6,326,527 B1
(45) Date of Patent: Dec. 4, 2001

(54) METHOD FOR ALTERING THE NUTRITIONAL CONTENT OF PLANT SEED

(75) Inventors: Julie A. Kirihara, Bloomington; Kenneth A. Hibberd, Falcon Heights, both of MN (US); Janice Anthony, Wakefield, RI (US)

(73) Assignee: Dekalb Genetics Corporation, Dekalb, IL (US)

( * ) Notice: Subject to any disclaimer, the term of this patent is extended or adjusted under 35 U.S.C. 154(b) by 0 days.

(21) Appl. No.: 08/763,704

(22) Filed: Dec. 9, 1996

Related U.S. Application Data

(63) Continuation-in-part of application No. 08/112,245, filed on Aug. 25, 1993.

(51) Int. Cl.⁷ .......................... C12M 15/00; C12M 15/05; A01H 5/00
(52) U.S. Cl. .......................... 800/278; 800/285; 800/286; 800/320.1
(58) Field of Search .................. 800/260, 263, 800/275, 278, 284, 285, 286, 287, 288, 292, 293, 294, 320.1

(56) References Cited

U.S. PATENT DOCUMENTS

| | | | |
|---|---|---|---|
| 4,370,160 | 1/1983 | Ziemelis | 71/117 |
| 4,399,216 | 8/1983 | Axel et al. | 435/6 |
| 4,520,113 | 5/1985 | Gallo et al. | 436/504 |
| 4,535,060 | 8/1985 | Comai | 435/172.3 |
| 4,536,475 | 8/1985 | Anderson | 435/172.3 |
| 4,559,301 | 12/1985 | Turner | 435/76 |
| 4,559,302 | 12/1985 | Ingolia | 435/172.3 |
| 4,581,847 | 4/1986 | Hibberd et al. | 47/58 |
| 4,634,665 | 1/1987 | Axel et al. | 435/68 |
| 4,642,411 | 2/1987 | Hibberd et al. | 800/1 |
| 4,665,030 | 5/1987 | Close | 435/240 |
| 4,666,844 | 5/1987 | Cheng | 435/240 |
| 4,683,202 | 7/1987 | Mullis | 435/91 |
| 4,708,818 | 11/1987 | Montagnier et al. | 435/5 |
| 4,727,028 | 2/1988 | Santerre et al. | 435/240.2 |
| 4,743,548 | 5/1988 | Crossway et al. | 435/172.3 |
| 4,761,373 | 8/1988 | Anderson et al. | 435/172.3 |
| 4,806,483 | 2/1989 | Wang | 435/240.49 |
| 4,885,357 | 12/1989 | Larkins et al. | 530/373 |
| 4,886,878 | 12/1989 | Larkins et al. | 536/26 |
| 4,940,835 | 7/1990 | Shah et al. | 800/205 |
| 4,945,050 | 7/1990 | Sanford et al. | 435/172.1 |
| 4,956,282 | 9/1990 | Goodman et al. | 435/69.51 |
| 4,971,908 | 11/1990 | Kishore et al. | 435/172.1 |
| 5,001,060 | 3/1991 | Peacock et al. | 435/172.3 |
| 5,004,863 | 4/1991 | Umbeck | 800/205 |
| 5,013,658 | 5/1991 | Dooner et al. | 435/172.3 |
| 5,015,580 | 5/1991 | Christou et al. | 435/172.3 |
| 5,034,322 | 7/1991 | Rogers et al. | 435/172.3 |
| 5,036,006 | 7/1991 | Sanford et al. | 435/170.1 |
| 5,049,500 | 9/1991 | Arnizen et al. | 435/172.3 |
| 5,077,399 | 12/1991 | Brauer et al. | 536/27 |
| 5,082,767 | 1/1992 | Hatfield et al. | 435/6 |
| 5,094,945 | 3/1992 | Comai | 435/172.3 |
| 5,097,093 | 3/1992 | Vandeventer et al. | 800/200 |
| 5,110,732 | 5/1992 | Benfey et al. | 435/172.3 |
| 5,134,074 | 7/1992 | Gordon et al. | 435/240.4 |
| 5,145,777 | 9/1992 | Goodman et al. | 435/172.3 |
| 5,164,310 | 11/1992 | Smith et al. | 435/172.3 |
| 5,177,010 | 1/1993 | Goldman et al. | 435/172.3 |
| 5,187,073 | 2/1993 | Goldman et al. | 435/172.3 |
| 5,187,267 | 2/1993 | Comai et al. | 536/23.1 |
| 5,188,642 | 2/1993 | Shah et al. | 47/58 |
| 5,188,958 | 2/1993 | Moloney et al. | 435/240.4 |
| 5,196,342 | 3/1993 | Donovan | 435/320.1 |
| 5,215,912 | 6/1993 | Hoffman | 435/240.4 |
| 5,240,841 | 8/1993 | Johnston et al. | 435/172.3 |
| 5,250,515 | 10/1993 | Fuchs et al. | 514/12 |
| 5,254,799 | 10/1993 | DeGrave et al. | 800/205 |
| 5,258,300 | 11/1993 | Glassman et al. | 435/240.4 |
| 5,268,463 | 12/1993 | Jefferson | 536/23.7 |
| 5,272,072 | 12/1993 | Kaneko et al. | 435/172.3 |
| 5,273,894 | 12/1993 | Strauch et al. | 435/129 |
| 5,276,268 | 1/1994 | Strauch et al. | 800/205 |
| 5,290,924 | 3/1994 | Last et al. | 536/24.1 |
| 5,302,523 | 4/1994 | Coffee et al. | 435/172.1 |
| 5,310,667 | 5/1994 | Eichholtz et al. | 435/172.3 |

(List continued on next page.)

FOREIGN PATENT DOCUMENTS

| | | | |
|---|---|---|---|
| 80893/87 | 12/1988 | (AU) | C12N/15/00 |
| 2032443 | 12/1990 | (CA) | C12N/15/87 |

(List continued on next page.)

OTHER PUBLICATIONS

Abstracts, 35th Annual Maize Genetics Conference, St. Charles, IL, p. 5, 45–46, (Mar. 18–21, 1993).

(List continued on next page.)

*Primary Examiner*—Gary Benzion
(74) *Attorney, Agent, or Firm*—Schwegman, Lundberg, Woessner & Kluth, P.A.

(57) ABSTRACT

The invention provides genetically engineered, preselected DNA sequences and methods of using them to alter the nutritional content of plant seed. Methods of the invention are directed to increasing the weight percent of at least one amino acid essential to the diet of animals, or increasing the starch content, of a plant. One such method involves stably transforming a cell of a plant with an a preselected DNA sequence encoding an RNA molecule substantially identical or complementary to a messenger RNA (mRNA) encoding a plant seed storage protein, preferably a seed storage protein which is deficient in at least one amino acid essential to the diet of animals. An alternative method employs stably transforming cells with at least two preselected DNA sequences, one of which encodes an RNA molecule substantially identical or complementary to a messenger RNA (mRNA) encoding a plant seed storage protein, and the other preselected DNA molecule which encodes a preselected polypeptide. The transformed cells are used to generate fertile transgenic plants and seeds. Transgenic seeds are characterized by expression of the preselected DNA sequence which results in a substantial inhibition of production of a seed storage protein deficient in at least one amino acid essential to the diet of animals and/or an increase in the weight percent of an amino acid essential to the diet of animals.

34 Claims, 13 Drawing Sheets

U.S. PATENT DOCUMENTS

| | | | |
|---|---|---|---|
| 5,350,689 | 9/1994 | Shillito et al. | 435/240.47 |
| 5,352,605 | 10/1994 | Fraley et al. | 435/240.4 |
| 5,367,110 | 11/1994 | Galili et al. | 800/205 |
| 5,371,003 | 12/1994 | Murry et al. | 435/172.3 |
| 5,371,015 | 12/1994 | Sanford et al. | 435/287 |
| 5,380,831 | 1/1995 | Adang et al. | 536/23.71 |
| 5,384,253 | 1/1995 | Krzyzek et al. | 435/172.3 |
| 5,405,765 | 4/1995 | Vasil et al. | 435/172.3 |
| 5,422,254 | 6/1995 | Londesborough et al. | 435/97 |
| 5,436,389 | 7/1995 | Pfund | 800/200 |
| 5,436,393 | 7/1995 | Rocha-Sosa et al. | 800/205 |
| 5,451,513 | 9/1995 | Maliga et al. | 438/172.3 |
| 5,464,763 | 11/1995 | Schilperoort et al. | 435/172.3 |
| 5,472,869 | 12/1995 | Krzyzek et al. | 435/240.4 |
| 5,484,956 | 1/1996 | Lundquist et al. | 800/205 |
| 5,489,520 | 2/1996 | Adams et al. | 435/172.3 |
| 5,491,288 | 2/1996 | Chaubet et al. | 800/205 |
| 5,495,071 | 2/1996 | Fischhoff et al. | 800/205 |
| 5,500,365 | 3/1996 | Fischhoff et al. | 435/240.4 |
| 5,508,468 | 4/1996 | Lundquist et al. | 800/205 |
| 5,516,668 * | 5/1996 | Maruta et al. | 435/172.3 |
| 5,538,877 | 7/1996 | Lundquist et al. | 435/172.3 |
| 5,538,880 | 7/1996 | Lundquist et al. | 435/172.3 |
| 5,545,545 | 8/1996 | Gengenbach et al. | 435/172.3 |
| 5,550,318 | 8/1996 | Adams et al. | 800/205 |
| 5,554,798 | 9/1996 | Lundquist et al. | 800/205 |
| 5,559,223 | 9/1996 | Falco et al. | 536/23.1 |
| 5,561,236 | 10/1996 | Leemans et al. | 800/205 |
| 5,563,324 | 10/1996 | Tarczynski et al. | 800/205 |
| 5,565,347 | 10/1996 | Fillatti et al. | 435/172.3 |
| 5,567,600 | 10/1996 | Adang et al. | 536/23.71 |
| 5,567,862 | 10/1996 | Adang et al. | 800/205 |
| 5,576,203 | 11/1996 | Hoffman | 435/172.3 |
| 5,578,702 | 11/1996 | Adang et al. | 530/350 |
| 5,580,716 | 12/1996 | Johnston et al. | 435/5 |
| 5,589,615 | 12/1996 | de Clercq et al. | 800/205 |
| 5,589,616 | 12/1996 | Hoffman et al. | 800/205 |
| 5,591,616 | 1/1997 | Hiei et al. | 435/172.3 |
| 5,593,963 | 1/1997 | Van Ooijen et al. | 514/12 |
| 5,595,733 | 1/1997 | Carswell et al. | 424/93.21 |
| 5,596,131 | 1/1997 | Horn et al. | 800/205 |
| 5,623,067 | 4/1997 | Vanderkerckhove et al. | 536/24.1 |
| 5,625,136 | 4/1997 | Koziel et al. | 800/205 |
| 5,641,664 | 6/1997 | D'Halluin et al. | 435/172.3 |
| 5,641,876 | 6/1997 | McElroy et al. | 536/24.1 |
| 5,677,474 | 10/1997 | Rogers | 800/205 |
| 5,693,507 | 12/1997 | Daniell et al. | 435/172.3 |
| 5,773,691 | 6/1998 | Falco et al. | 800/205 |
| 5,780,708 | 7/1998 | Lundquist et al. | 800/205 |
| 5,780,709 | 7/1998 | Adams et al. | 800/205 |
| 5,874,265 | 2/1999 | Adams et al. | 435/172.3 |
| 5,886,244 | 3/1999 | Tomes et al. | 800/293 |
| 5,919,675 | 7/1999 | Adams et al. | 435/172.3 |
| 5,969,213 | 10/1999 | Adams et al. | 800/205 |
| 5,990,387 | 11/1999 | Tomes et al. | 800/293 |

FOREIGN PATENT DOCUMENTS

| | | | |
|---|---|---|---|
| 2064761 | 2/1991 | (CA) | C12N/15/82 |
| 0018970 | 9/1882 | (DE) | 47/58 |
| 37 38 874 A1 | 11/1988 | (DE) | A01H/1/06 |
| 40 13 099 A1 | 10/1991 | (DE) | C12N/15/82 |
| 0 126 537 A2 | 4/1983 | (EP) | A61K/9/52 |
| 0 131 623 B1 | 1/1984 | (EP) | C12N/15/11 |
| 0 141 373 A3 | 5/1985 | (EP) | A01G/7/00 |
| 0 142 924 A2 | 5/1985 | (EP) | C12N/15/00 |
| 0 154 204 A2 | 9/1985 | (EP) | C12N/15/00 |
| 0 160 390 A2 | 11/1985 | (EP) | A01H/15/10 |
| 0 174 791 A2 | 3/1986 | (EP) | C12N/15/00 |
| 0 189 707 A2 | 8/1986 | (EP) | C12N/15/00 |
| 0 193 259 A1 | 9/1986 | (EP) | C12N/15/00 |
| 0 204 549 A2 | 10/1986 | (EP) | C12N/15/00 |
| 0 202 668 A2 | 11/1986 | (EP) | C12N/5/02 |
| 0 242 236 A1 | 10/1987 | (EP) | C12N/15/00 |
| 0 242 246 A1 | 11/1987 | (EP) | C12N/15/00 |
| 0 299 552 A1 | 1/1988 | (EP) | C12N/15/00 |
| 0 257 472 A2 | 3/1988 | (EP) | C12N/15/00 |
| 0 262 971 A2 | 5/1988 | (EP) | A01H/1/02 |
| 0 269 601 A2 | 6/1988 | (EP) | C12N/15/00 |
| 0 270 356 A2 | 6/1988 | (EP) | C12N/15/00 |
| 0 271 408 | 6/1988 | (EP) | C12N/15/00 |
| 0 275 069 A2 | 7/1988 | (EP) | C12N/15/00 |
| 0 280 400 A2 | 8/1988 | (EP) | A01C/1/06 |
| 0 282 164 A2 | 9/1988 | (EP) | C12N/5/00 |
| 0 289 479 A2 | 11/1988 | (EP) | C12N/15/00 |
| 0 290 395 A2 | 11/1988 | (EP) | C12N/15/00 |
| 0 292 435 A1 | 11/1988 | (EP) | C12N/15/00 |
| 0 301 749 A2 | 2/1989 | (EP) | C12N/15/00 |
| 0 353 908 A2 | 7/1989 | (EP) | C12N/15/29 |
| 0 331 083 A2 | 9/1989 | (EP) | C12N/15/00 |
| 0 331 855 A2 | 9/1989 | (EP) | C12M/3/00 |
| 0 334 539 A2 | 9/1989 | (EP) | C12N/15/00 |
| 0 335 528 A2 | 10/1989 | (EP) | C12N/15/00 |
| 0 348 348 A2 | 12/1989 | (EP) | A01N/65/00 |
| 0 385 962 A1 | 2/1990 | (EP) | C12N/15/82 |
| 0 359 472 A2 | 3/1990 | (EP) | C12N/15/32 |
| 0 359 617 A2 | 3/1990 | (EP) | C12N/15/53 |
| 0 360 750 A2 | 3/1990 | (EP) | C12N/15/29 |
| 0 408 403 A1 | 9/1990 | (EP) | C12N/15/32 |
| 0 420 358 A1 | 4/1991 | (EP) | C12N/15/55 |
| 0 424 047 A1 | 4/1991 | (EP) | C12N/15/87 |
| 0 442 174 A1 | 4/1991 | (EP) | C12N/15/82 |
| 0 459 643 A2 | 5/1991 | (EP) | C12N/15/82 |
| 0 442 175 A1 | 8/1991 | (EP) | A01H/1/02 |
| 0 452 269 A2 | 11/1991 | (EP) | C12N/15/82 |
| 0 469 273 A1 | 2/1992 | (EP) | C12N/15/82 |
| 0 485 970 A3 | 5/1992 | (EP) | C12N/15/82 |
| 0 589 110 A1 | 3/1994 | (EP) | A01N/63/02 |
| 0 620 281 A2 | 10/1994 | (EP) | A12N/15/82 |
| 2 661 421 | 11/1991 | (FR) | C12N/15/09 |
| 2 159 173 | 11/1985 | (GB) | C12N/15/00 |
| 61-134343 | 5/1984 | (JP) | . |
| 8-103267 A | 4/1996 | (JP) | C12N/9/02 |
| 8-266179 A | 10/1996 | (JP) | A01H/5/00 |
| 8801444 | 1/1990 | (NL) | C12N/15/87 |
| WO 85/01856 | 5/1985 | (WO) | A01B/76/00 |
| WO 85/02972 | 7/1985 | (WO) | A01C/1/06 |
| WO 85/02973 | 7/1985 | (WO) | A01J/7/00 |
| 86/01536 | 3/1986 | (WO) | C12P/15/00 |
| 86/03776 | 7/1986 | (WO) | C12N/15/00 |
| WO 87/04181 | 7/1987 | (WO) | C12N/1/00 |
| WO 87/05629 | 9/1987 | (WO) | C12N/15/00 |
| 88/08034 | 10/1988 | (WO) | C12P/21/00 |
| WO 89/04371 | 5/1989 | (WO) | C12N/21/00 |
| 89/10396 | 11/1989 | (WO) | C12N/5/00 |
| WO 89/11789 | 12/1989 | (WO) | A01H/1/00 |
| WO 89/12102 | 12/1989 | (WO) | C12N/15/00 |
| 90/01551 | 2/1990 | (WO) | C12N/15/82 |
| WO 90/01869 | 3/1990 | (WO) | A01H/1/00 |
| WO 90/02801 | 3/1990 | (WO) | C12N/15/32 |
| WO 90/10691 | 8/1990 | (WO) | C12N/5/00 |
| WO 90/10725 | 9/1990 | (WO) | C23C/16/00 |
| WO 91/02071 | 2/1991 | (WO) | C12N/15/82 |
| 91/04270 | 4/1991 | (WO) | C07K/13/00 |
| WO 91/04323 | 4/1991 | (WO) | C12N/9/10 |
| WO 91/00183 | 5/1991 | (WO) | . |
| WO 91/10725 | 7/1991 | (WO) | C12N/5/00 |
| WO 91/16432 | 10/1991 | (WO) | C12N/15/31 |
| WO 92/06205 | 4/1992 | (WO) | C12N/15/82 |
| WO 92/09696 | 6/1992 | (WO) | C12N/15/82 |
| WO 92/12250 | 7/1992 | (WO) | C12N/15/82 |

| | | | |
|---|---|---|---|
| 92/14822 | 9/1992 | (WO) | C12N/15/29 |
| 92/17580 | 10/1992 | (WO) | C12N/05/10 |
| WO 92/19731 | 11/1992 | (WO) | C12N/15/00 |
| 93/06220 | 4/1993 | (WO) | C12N/15/82 |
| WO 93/07278 | 4/1993 | (WO) | C12N/15/82 |
| 93/09237 | 5/1993 | (WO) | C12N/15/82 |
| WO 93/08682 | 5/1993 | (WO) | A01H/1/00 |
| WO 93/14210 | 7/1993 | (WO) | C12N/15/82 |
| WO 93/19190 | 9/1993 | (WO) | C12N/15/82 |
| 94/08031 | 4/1994 | (WO) | C12P/13/22 |
| 94/10315 | 5/1994 | (WO) | C12N/15/29 |
| 94/14970 | 7/1994 | (WO) | C12N/15/82 |
| 94/20628 | 9/1994 | (WO) | C12N/15/82 |
| 94/21805 | 9/1994 | (WO) | C12N/15/82 |
| 95/06128 | 3/1995 | (WO) | C12N/15/82 |
| 95/13389 | 5/1995 | (WO) | C12N/15/82 |
| 95/30005 | 11/1995 | (WO) | C12N/15/29 |
| 96/00789 | 1/1996 | (WO) | C12N/15/82 |

OTHER PUBLICATIONS

*In Vitro Cellular & Development Biology*, 21, Program Issue: Thirty–Sixth Annual Meeting of the Tissue Culture Association, New Orleans, LA, 88 p., (Mar. 1985).

*In Vitro Cellular & Development Biology*, 23, Program Issue: Thirty–Eighth Annual Meeting of the Tissue Culture Association, Washington, D.C., 93 p., (Mar. 1987).

*In Vitro Cellular & Development Biology*, 24, Program Issue: Thirty–Ninth Annual Meeting of the Tissue Culture Association, Las Vegas, NV, 92 p., (Mar. 1988).

*In Vitro Cellular & Development Biology*, 25, Program Issue: Fortieth Annual Meeting of the Tissue Culture Association, Orlando, Fl, 73 p., (Mar. 1989).

*In Vitro Cellular & Development Biology*, 26, Program Issue: Forty–First Annual Meeting of the Tissue Culture Association, Houston, TX, 88 p., (Mar. 1990).

*In Vitro Cellular & Development Biology*, 28, Program Issue: 1992 World Congress on Cell and Tissue Culture, Washington, D.C., ISSN 0883–8364 (Jun. 20–25, 1992).

"Ciba–Geigy Joins Maize Transformers" *AGRWO*, No. 118, 20, (Aug. 31, 1990).

"European Firm Devises Insect–Resistant Plants", *Agricultural Biotechnology News*, 1, 6, (Mar.–Apr. 1986).

"Molecular Strategies for Crop Improvement", *Journal of Cellular Biochemistry*, Supplement 14e, List of Plenary and Poster Sessions, organized by Arntzen, C., et al., for The Keystone Conference on Molecular Strategies for Crop Plant Improvement, held at the 19th UCLA Symposia, 257, (1990).

"Monsanto, DeKalb Gunning for Insect–, Disease–Resistant Corn", *Biotechnology Newswatch*, 4–5, (May 7, 1990).

"Plant Science Produces Transformed Corn", *Chemical and Engineering News*, 7, (Jan. 29, 1990).

Abbe, E.C., et al., "The Growth of the Shoot Apex in Maize: Embryogeny", *American Journal of Botany*, 41, 285–293, (Apr. 1954).

Adang, M.J., et al., "Expression of a *Bacillus thuringiensis* Insecticidal Crystal Protein Gene in Tobacco Plants", *Molecular Strategies for Crop Protection*, Arntzen, C.J., et al. (eds.), Alan R. Liss, Inc., New York, 345–353, (1987).

Anderson, P.C., et al., "Herbicide–Tolerant Mutants of Corn", *Genome*, 31, 994–999, (1989).

Angus, T.A., "Implications of Some Recent Studies of *Bacillus thuringiensis* —A Personal Purview", Proceedings of the 4th International Colloquium on Insect Pathology, College Park, MD, 183–189, (Aug. 25–28, 1970).

Armaleo, D., et al., "Biolistic Nuclear Transformation of *Saccharomyces cerevisiae* and Other Fungi", *Curr. Genet.*, 17, 97–103, (1990).

Armstrong, C.L., et al., "Development and Availability of Germplasm with High Type II Culture Formation Response", *Maize Genetics Cooperation Newsletter*, 65, 92–93, (Mar. 1, 1991).

Aronson, A.I., et al., "*Bacillus thuringiensis* and Related Insect Pathogens", *Microbiological Reviews*, 50, 1–24, (Mar. 1986).

Aronson, J.N., et al., "Toxic Trypsin Digest Fragment from the *Bacillus thuringiensis* Parasporal Protein", *Applied and Environmental Microbiology*, 53, 416–421, (Feb. 1987).

Bartels, D., et al., "An ABA and GA Modulated Gene Expressed in the Barley Embryo Encodes an Aldose Reductase Related Protein", *EMBO Journal*, 10, 1037–1043 (1991).

Barton, K.A., et al., "*Bacillus thuringiensis* δ–Endotoxin Expressed in Transgenic *Nicotiana tabacum* Provides Resistance to Lepidopteran Insects", *Plant Physiol.*, 85, 1103–1109, (1987).

Barton, K.A., et al., "Production of *Bacillus thuringiensis* Insecticidal Proteins in Plants", *Transgenic Plants*, vol. 1, Kung, S.–D., et al., (eds.), Academic Press, Inc., San Diego, CA, 297–315, (1993).

Birk, Y., et al., "Separation of a Tribolium–Protease Inhibitor from Soybeans on a Calcium Phosphate Column", *Biochem. Biophys. Acta*, 67, 326–328, (Feb. 12, 1963).

Bishop, D.H., et al., "Genetically Engineered Viral Insecticides—A Progress Report 1986–1989", *Pestic. Sci.*, 27, 173–189, (1989).

Boylan–Pett, W., et al., "Effectiveness of *Bacillus thuringiensis*–Transgenic Potato Plants for Control of Colorado Potato Beetles, 1991", *Insecticide & Acaricide Tests: 1992*, 17, 124–125, (1992).

Boynton, J.E., et al., "Chloroplast Transformation in Chlamydomonas with High Velocity Microprojectiles", *Science*, 240, 1534–1537, (Jun. 10, 1988).

Bryant, J.A., "At Last: Transgenic Cereal Plants from Genetically Engineered Protoplasts", *Trends in Biotechnology*, 6, 291–292, (Dec. 1988).

Burgerjon, A., et al., "Industrial and International Standardization of Microbial Pesticides—I. *Bacillus thuringiensis*", *Entomophaga*, 22, 121–129, (1977).

Busvine, J.R., *A Critical Review of the Techniques for Testing Insecticides*, Table of Contents, Commonwealth Agricultural Bureaux, Slough, England, iii–xi, (1971).

Bytebier, B., et al., "T–DNA Organization in Tumor Cultures and Transgenic Plants of the Monocotyledon *Asparagus officinalis*", *Proc. Natl. Acad. Sci. USA*, 84, 5345–5349, (Aug. 1987).

Caimi, P.G., et al., "Fructan Accumulation and Sucrose Metabolism in Transgenic Maize Endosperm Expressing a *Bacillus amyloliquefaciens SacB* Gene", *Plant Physiol.*, 110, 355–363 (1996).

Calabrese, D.M., et al., "A Comparison of Protein Crystal Subunit Sizes in *Bacillus thuringiensis*", *Canadian Journal of Microbiology*, 26, 1006–1010, (Aug. 1980).

Caplan, A., et al., "Introduction of Genetic Material into Plant Cells", *Science*, 222, 815–821, (Nov. 18, 1983).

Carozzi, N.B., et al., "Expression of a Chimeric CaMV 35S *Bacillus thuringiensis* Insecticidal Protein Gene in Transgenic Tobacco", *Plant Molecular Biology*, 20, 539–548, (1992).

Chaleff, R.S., "Induction, Maintenance, and Differentiation of Rice Callus Cultures on Ammonium as Sole Nitrogen Source", *Plant Cell Tissue Organ Culture*, 2, 29–37, (1983).

Christou, P., et al., "Inheritance and Expression of Foreign Genes in Transgenic Soybean Plants", *Proc. Natl. Acad. Sci. USA*, 86, 7500–7504, (Oct. 1989).

Clemente, T.E., et al., "The Components of Variation Associated with Agrobacterium–Mediated Transformation of Soybean", *In. Vitro Cellular and Developmental Biology*, 31, Abstract No. W–20, 28A, (Mar. 1995).

Cooksey, K.E., "Purification of a Protein from *Bacillus thuringiensis* Toxic to Larvae of Lepidoptera", *Biochem. J.*, 106, 445–454, (1968).

De Block, M., et al., "Expression of Foreign Genes in Regenerated Plants and Their Progeny", *EMBO J.*, 3, 1681–1689, (1984).

De Block, M., et al., "The Use of Phosphinothricin Resistance as a Selectable Marker in Tobacco Protoplast Transformation", In: *Progress in Plant Protoplast Research*, Proceedings of the the 7th International Protoplast Symposium, Wageningen, The Netherlands, Puite, K.J., et al., (eds.), Kluwer Academic Publishers, Dordrecht, The Netherlands, 389–390, (Dec. 6–11, 1987).

Denecke, J., et al., "Quantification of Transient Expression Levels of Genes Transferred to Plant Protoplasts by Electroporation", *Progress in Plant Protoplast Research*, Puite, K.J., et al., (eds.), Proceedings of the 7th International Protoplast Symposium, Wageningen, The Netherlands, 337–338, (Dec. 6–11, 1987).

Denholm, I., et al., "Tactics for Managing Pesticide Resistance in Arthropods: Theory and Practice", *Annu. Rev. Entomol.*, 37, 91–112, (1992).

Di, R., et al., "Transformation of Soybean with Bean Pod Mottle Virus Coat Proteins–Precursor Gene using the Biolistic Method", *Phytopathology*, 83, Abstract No. A394, p. 1374, (Dec. 1993).

Duncan, D.R., et al., "The Production of Callus Capable of Plant Regeneration for Immature Embryos of Numerous *Zea Mays* Genotypes", *Planta*, 165, 322–332, (1985).

Dunder, E., et al., "High Frequency Transformation of Maize by Microprojectile Bombardment of Immature Embryos", Abstracts, 35 Annual Maize Genetics Conference, St. Charles, IL, Poster No. 16, p. 30 (Mar. 18–21, 1993).

Dunder, E., et al., "Transgenic Anthocyanin Color Phenotypes Produced in Callus, Plants and Progeny of Maize", Abstracts, 35th Annual Maize Genetics Conference, St. Charles, IL, Poster No. 15, p. 30 (Mar. 18–31, 1993).

Dunleavy, J.M., "*Curtobacterium plantarum* sp. nov. Is Ubiquitous in Plant Leaves and Is Seed Transmitted in Soybean and Corn", *International Journal of Systematic Bacteriology*, 39, 240–249, (Jul. 1989).

Dybvig, K., et al., "Transposition of Gram–Positive Transposon Tn916 in *Acholeplasma laidlawii* and *Mycoplasma pulmonis*", *Science*, 235, 1392–1394, (Mar. 13, 1987).

Edallo, S., et al., "Chromosomal Variation and Frequency of Spontaneous Mutation Associated with in vitro Culture and Plant Regeneration in Maize", *Maydica*, 26, 39–56, (1981).

European Patent Office, Decision T153/88 (Stahlwerke Peine–Salzgitter/Hot strip) Issued by Technical Board of Appeal 3.3.3 on Jan. 9, 1991 (Not Published in the Official Journal): English Translation from [1997] EPOR pp. 371 to pp. 378, 371–378, (1997).

Fast, P.G., et al., "*Bacillus thuringiensis* δ–Endotoxin: Evidence that Toxin Acts at the Surface of Susceptible Cells", *Experientia*, 34, 762–763, (1978).

Faust, R.M., et al., "Bacteria and Their Toxins as Insecticides", In: *Microbial and Viral Pesticides*, Kurstak, E., (ed.), Marcel Dekker, Inc., New York, 75–208, (1982).

Finkle, B.J., et al., "Growth and Regeneration of *Alfalfa* Callus Lines After Freezing in Liquid Nitrogen", *Plant Science*, 42, 133–140, (1985).

Finney, D.J., In: *Probit Analysis: A Statistical Treatment of the Sigmoid Response Curve*, iii–ix, (1952).

Fischoff, D.A., et al., "Insect Tolerant Transgenic Tomato Plants", *Bio/technology*, 5, 807–812, (1987).

Follansbee, E., et al., "Transformation of *Euphorbia lathyris* by Agrobacterium Rhizogenes", *In Vitro Cellular and Developmental Biology*, Program Issue, Congress on In Vitro Biology, Abstract No. P–1093, 72A, (May 20–24, 1995).

Fromm, M., et al., "Transient Expression and Stable Transformation of Maize Using Microprojectiles", *In: Plant Molecular Biology*, vol. 2, Herrmann, R.G., et al., (eds.), Plenum Press, New York, 219, (1991).

Fukuto, T.R., "Physicochemical Aspects of Insecticidal Action", In: *Insecticidal Biochemistry and Physiology*, Wilkinson, C.F., (ed.), Plenum Press, New York, 397–428, (1976).

Gallagher, S., "Progress and Promise of the Particle Gun", *Ag Biotechnology News*, 6, 12–13, (Mar.–Apr. 1989).

Gallie, D.R., et al., "The 5'–leader Sequence of Tobacco Mosaic Virus RNA Enhances the Expression of Foreign Gene Transcripts in Vitro and In Vivo", *Nucleic Acids Research*, 15, 3257–3273, (1987).

Gatehouse, A.M.R., et al., "Assessment of the Antimetabolic Effects of Trypsin Inhibitors from Cowpea (*Vigna unguiculata*) and Other Legumes on Development of the Bruchid Beetle *Callosobruchus maculatus*", *J. Sci. Food Agric.*, 34, 345–350, (1983).

Genovesi, A.D., et al., "Embryogenesis in Callus Derived from Rice Microspores", *Plant Cell Reports*, 1, 257–260, (1982).

Georghiou, G.P., et al., "Factors Influencing the Evolution of Resistance", In: *Pesticide Resistance: Strategies and Tactics for Management*, Committee on Strategies for the Management of Pesticide Resistant Pest Populations, Board on Agriculture, National Research Council, National Academy Press, Washington, D.C., 157–169, (1986).

Gerlach, W.L., "Genetic Engineering: Its Place in Plant Breeding", In: *Plant Breeding and Genetic Engineering*, Zakri, A.H., (ed.), Society for the Advancement of Breeding Researches in Asia and Oceania, Bangi, Malaysia, 269–277, (1988).

Goff, S.A., et al., "Transactivation of Anthocyanin Biosynthetic Genes Following Transfer of B Regulatory Genes into Maize Tissues", *EMBO Journal*, 9, 2517–2522, (1990).

Goldburg, R.J., et al., "Are B.T.K. Plants Really Safe to Eat?", *Bio/technology*, 8, 1011–1015, (Nov. 1990).

Goldfarb, B., et al., "Transient Expression of Microprojectile–Introduced DNA in Douglas–Fir", *J. Cell. Biochem.*, 13D, Abstract No. M121, p. 259 (1989).

Goldman, S.L., et al., "Transformation of *Zea mays* by *Agrobacterium tumefaciens:* Evidence for Stable Genetic Alterations", *Journal of Cellular Biochemistry*, 11B, Abstract No. F 202, p. 26, (1987).

Gordon, P.N., et al., "Plant Regeneration from Tissue Cultures of Maize", *Maize Genetics Cooperation Newsletter*, 51, 79–80, (Mar. 1, 1977).

Gordon–Kamm, W.J., et al., "Transformation of Maize Using Microprojectile Bombardment: An Update and Perspective", *In Vitro Cellular and Developmental Biology*, 27, 21–27, (Jan. 1991).

Green, C.E., "New Developments in Plant Tissue Culture and Plant Regeneration", In: *Basic Biology of New Developments in Biotechnology*, Hollaender, A., et al., (eds.), Plenum Press, New York, 195–209, (1983).

Green, C.E., "Somatic Embryogenesis and Plant Regeneration from the Friable Callus of *Zea mays*", Proceedings of the 5th International Congress on Plant Tissue & Cell Culture, Tokyo, Japan, 107–108, (1982).

Haccius, B., "Question of Unicellular Origin of Non–Zygotic Embryos in Callus Cultures", *Phytomorphology*, 28, 74–81, (1978).

Hallborn, J., et al., "Xylitol Production by Recombinant *Saccharomyces cerevisiae*", *Bio/technology*, 9, 1090–1095 (Nov. 1991).

Harms, C.T., et al., "Regeneration of Plantlets from Callus Cultures of *Zea mays* L.", *Z. Ptlanzenzuchtg.* 77, 347–351, (1976).

Hartree, E.F., "Determination of Protein: A Modification of the Lowry Method that Gives a Linear Photometric Response", *Analytical Biochemistry*, 48, 422–427, (1972).

Harvey, W.R., et al., "Potassium Ion Transport ATPase in Insect Epithelia", *J. Exp. Biol.*, 106, 91–117, (1983).

Heimpel, A.M., et al., "Recent Advances in the Knowledge of Some Bacterial Pathogens of Insects", Proceedings of the Tenth International Congress of Entomology, vol. 4, 711–722, (1956).

Heimpel, A.M., et al., "The Site of Action of Crystalliferous Bacteria in Lepidoptera Larvae", *Journal of Insect Pathology*, 1, 152–170, (1959).

Hernalsteens, J.–P., et al., "An Agrobacterium–Transformed Cell Culture from the Monocot *Asparagus Officinalis*", *The EMBO Journal*, 3, 3039–3041, (Dec. 1984).

Hibberd, K.A., "Induction, Selection, and Characterization of Mutants in Maize Cell Cultures", In: *Cell Culture and Somatic Cell Genetics of Plants*, vol. 1, Vasil, I.K., (ed.), Academic Press, Inc., Orlando, FL, 571–576, (1984).

Hickle, L.A., et al., "Analytical Chemistry of *Bacillus thuringiensis*: An Overview", *In: Analytical Chemistry of Bacillus thuringiensis*, Hickle, L.A., et al., (eds.), Developed from a Symposium Sponsored by the Division of Agrochemicals at the 198th National Meeting of the American Chemical Society, Miami Beach, FL, vii–ix, 1–8, (Sep. 10–15, 1989).

Hilder, V.A., et al., "A Novel Mechanism of Insect Resistance Engineered into Tobacco", *Nature*, 330, 160–163, (Nov. 12, 1987).

Hodges, T.K., et al., "Genotype Specificity of Somatic Embryogenesis and Regeneration in Maize", *Bio/technology*, 4, 219–223, (Mar. 1986).

Hodges, T.K., et al., "Regeneration of Maize", In: *Biotechnology in Plant Science*, Zaitlin, M., et al., (ed.), Academic Press, Inc., Orlando, FL, 15–33, (1985).

Hoekema, A., et al., "Condon Replacement in the PGK1 Gene of *Saccharomyces cerevisiae:* Experimental Approach to Study the Role of Biased Codon Usage in Gene Expression", *Molecular and Cellular Biology*, 7, 2914–2924, (Aug. 1987).

Hofmann, C., et al., "Binding of the Delta Endotoxin from *Bacillus thuringiensis* to Brush–Border Membrane Vesicles of the Cabbage Butterfly (*Pieris Brassicae*)", *Eur. J. Biochem.*, 173, 85–91, (1988).

Hofmann, C., et al., "Specificity of *Bacillus thuringiensis* δ–Endotoxins is Correlated with the Presence of High–Affinity Binding Sites in the Brush Border Membrane of Target Insect Midguts", *Proc. Natl. Acad. Sci. USA*, 85 7844–7848, (Nov. 1988).

Höfte, H., et al., "Monoclonal Antibody Analysis and Insecticidal Spectrum of Three Types of Lepidopteran–Specific Insecticidal Crystal Proteins of *Bacillus thuringiensis*", *Applied and Environmental Microbiology*, 54, 2010–2017, (Aug. 1988).

Höfte, H., et al., "Structural and Functional Analysis of a Cloned Delta Endotoxin of *Bacillus thuringiensis berliner* 1715", *Eur. J. Biochem.*, 161, 273–280, (1986).

Hollingworth, R.M., "The Biochemical and Physiological Basis of Selective Toxicity", In: *Insecticidal Biochemistry and Physiology*, Wilkinson, C.F., (ed.), Plenum Press, New York, 431–506, (1976).

Horsch, R.B., et al., "A Simple and General Method for Transferring Genes into Plants", *Science*, 227, 1229–1231, (Mar. 8, 1985).

Hu, C.C., et al., "Factors Contributing to the Anomalous Electrophoretic Mobility of Cucumoviruses Coat Proteins in SDS/Polyacrylamide Gels", *Phytopathology*, 83, Abstract No. A393, 1374, (Dec. 1993).

Huber, H.E., et al., "*Bacillus thuringiensis* δ–Endotoxin: Composition and Activation", In: *Pathogenesis of Invertebrate Microbial Diseases*, Davidson, E.W., (ed.), Allanheld, Osmun & Co. Publishers, Inc., Totowa, NJ, 209–234, (1981).

Huber–Lukac, M., et al., "Characterization of Monoclonal Antibodies to a Crystal Protein of *Bacillus thuringiensis* subsp. *kurstaki*", *Infection and Immunity*, 54, 228–232, (Oct. 1986).

Imbrie–Milligan, C.W., et al., "Microcallus Formation from Maize Protoplasts Prepared from Embryogenic Callus", *Planta*, 168, 395–401, (1986).

Ishitani, M., et al. "Expression of the Betaine Aldehyde Dehydrogenase Gene in Barley in Response to Osmotic Stress and Abscisic Acid" *Plant Molecular Biology*, 27, 307–315 (1995).

Jarrett, P., "Potency Factors in the delta–Endotoxin of *Bacillus thuringiensis* var. *aizawi* and the Significance of Plasmids in their Control", *Journal of Applied Bacteriology*, 58, 437–448, (1985).

Johnson, D.E., "Toxicity of *Bacillus thuringiensis* Entomocidal Protein Toward Cultured Insect Tissue", *Journal of Invertebrate Pathology*, 38, 94–101, (1981).

Kausch, A.P., et al., "Effects of Microprojectile Bombardment on Embryogenic Suspension Cell Cultures of Maize (*Zea mays* L.) Used for Genetic Transformation", *Planta*, 196, 510–509, (1995).

King, P., et al., "Maize", In: *Handbook of Plant Cell Culture*, vol. 2, Sharp, W.R., et al., (eds.), Macmillan Publishing Company, New York, 69–91, (1984).

Klein, T.M., "Transformation of Maize Through Particle Bombardment", In: *Biotechnology in Agriculture and Forestry*, 25, Maize, Bajaj, Y.P.S., (ed.), Springer–Verlag, Berlin, 241–251, (1994).

Klein, T.M., et al., "Advances in Direct Gene Transfer into Cereals", *In: Genetic Engineering: Principles and Methods*, vol. 11, Setlow, J.K., (ed.), Plenum Publishing Corp., New York, 13–31, (1989).

Klein, T.M., et al., "Particle Bombardment: A Universal Approach for Gene Transfer to Cells and Tissues", *Current Opinion in Biotechnology*, 4, 583–590, (1993).

Klein, T.M., et al., "Particle Gun Technology: A Novel Method for the Introduction of DNA into Living Cells", Program and Abstracts for an International Symposium: "Biotechnology in Plant Science: Relevance to Agriculture in the Eighties", Poster, #28, Ithaca, NY, 25, (Jun. 23–27, 1985).

Klein, T.M., et al., "Progress in the Genetic Transformation of Recalcitrant Crop Species", *Aspects of Applied Biology*, 39, 35–44, (1994).

Klein, T.M., et al., "Stable Genetic Transformation of Intact Nicotana Cells by the Particle Bombardment Process", *Proc. Natl. Acad. Sci. USA*, 95, 5502–5505, (Nov. 1988).

Klein, T.M., et al., "Transformation of Microbes, Plants and Animals by Particle Bombardment", *Biotechnology*, 10, 286–291, (Mar. 1992).

Knowles, B.H., et al., "Characterization and Partial Purification of a Plasma Membrane Receptor for *Bacillus thuringiensis* var. Kurstaki Lepidopteran–Specific δ–Endotoxin", *J. Cell Sci.*, 83, 89–101, (1986).

Knowles, B.H., et al., "Lectin–Like Binding of *Bacillus thuringiensis* var. Kurstaki Lepidopteran–Specific Toxin is an Initial Step in Insecticidal Action", *FEBS Letters*, 168, 197–202, (Mar. 1984).

Koziel, M.G., et al., "The Insecticidal Crystal Proteins of *Bacillus thuringiensis*: Past, Present and Future Uses", *Biotechnology and Genetic Reviews*, 11, 171–228, (Dec. 1993).

Lamark, T., et al., "DNA Sequence and Analysis of the bet Genes Endcoding the Osmoregulatory Choline–Glycine Betaine Pathway of *Escherichia coli*", *Molecular Microbiology*, 5, 1049–1064 (1991).

Langridge, W.H., et al., "Electric Field Mediated DNA Transformation in Plant Protoplasts", Program and Abstracts for an International Symposium: "Biotechnology in Plant Science: Relevance to Agriculture in the Eighties", Ithaca, NY, Poster #30, p. 25, (Jun. 23–27, 1985).

Leason, M., et al., "Inhibition of Pea Leaf Glutamine Synthetase by Methionine Sulphoximine, Phosphinothricin and Other Glutamate Analogues", *Biochemistry*, 21, 855–857, (1982).

Lee, B., "Cereal Transformation", *Plants Today*, 9–11, (Jan.–Feb. 1989).

Lin, F.–F., et al., "Transformation and Analysis of Inducible Pal Genes in Potato", *In Vitro Cellular and Developmental Biology*, 28, Abstract No. P–1129, p. 123A, (Mar. 1992).

Lörz, H., et al., "Gene Transfer to Cereal Cells Mediated by Protoplast Transformation", *Mol. Gen. Genet.*, 199, 178–182, (1985).

Lowe, K., et al., "Germline Transformation of Maize Following Manipulation of Chimeric Shoot Meristems", *Biotechnology*, 13, 677–682, (Jul. 1995).

Lowe, K., et al., "Germline Transformation of Maize using Shoot Multiplication to Enlarge Chimeric Sectors", *In Vitro Cellular and Developmental Biology*, Program Issue, Congress on In Vitro Biology, Abstract No. P–1095, 72A, (May 20–24, 1995).

Lowe, K., et al., "Plant Regeneration via Organogenesis and Embryogenesis in the Maize Inbred Line B73", *Plant Science*, 41, 125–132, (1985).

Luckow, V.A., et al., "Trends in the Development of Baculovirus Expression Vectors", *Bio/Technology*, 6, 47–55, (Jan. 1988).

Lüthy, P., "Insecticidal Toxins of *Bacillus thuringiensis*", *FEMS Microbiology Letters*, 8, 1–7, (1980).

Mackey, C.J., et al., "Transgenic Maize", In: *Transgenic Plants*, vol. 2, Kung, S.–D., et al., (eds.), Academic Press, Inc., 21–33, (Oct 1992).

Maliga, P., "Plastid Transformation: A New Tool for Basic Science and for Biotechnological Applications", *In Vitro Cellular and Developmental Biology*, 31, Abstract No. W–18, 28A, (Mar. 1995).

Mangano, M.L., et al., "Long–Term Cold Storage of Regenerable Maize Callus", *In Vitro Cellular and Developmental Biology*, 25, Abstract No. 224, p. 66A, (Mar. 1989).

Mariani, T., et al., "The Production and Analysis of Genetically–Engineered Male–Sterile Plants of Maize", Abstracts, 35th Annual Maize Genetics Conference, St. Charles, IL, Poster No. 46, p. 45 (Mar. 18–21, 1993).

Martens, J.W.M., et al., "Insecticidal Activity of a Bacterial Crystal Protein Expressed by a Recombinant Baculovirus in Insect Cells", *Applied and Environmental Microbiology*, 56, 2764–2770, (Sep. 1990).

Martens, J.W., et al., "Mapping Characterization of the Entomocidal Domain of the *Bacillus thuringiensis* CryIA(b) Protoxin", *Mol. Gen. Genet.*, 247, 482–487, (1995).

McElroy, D., et al., "Isolation of an Efficient Actin Promoter for Use in Rice Transformation", *The Plant Cell*, 2, 163–171, (Feb. 1990).

Merryweather, A.T., et al., "Construction of Genetically Engineered Baculovirus Insecticides Containing the *Bacillus thuringiensis* subsp. *Kurstaki* HD–73 Delta Endotoxin", *Journal of General Virology*, 71, 1535–1544, (1990).

Mikula, B.C., "Programming Heritable Epigenetic Change in Gene Expression with Temperature and Light", Abstracts, 35th Annual Maize Genetics Conference, St. Charles, IL, p. 5 (Mar. 18–21, 1993).

Mink, G.I., "Pollen– and Seed–Transmitted Viruses and Viriods", *Annu. Rev. Phytopathol.*, 31, 375–402, (1993).

Moffat, A.S., "Higher Yielding Perennials Point the Way to New Crops", *Science*, 274, 1469–1470, (Nov. 29, 1996).

Molnar, S.J., et al., "Initiation of Totipotent Tissue Cultures from Undeveloped Axillary and Secondary Ears", *Maize Genetics Cooperation Newsletter*, 54, 52–53, (Mar. 31, 1980).

Morelli, G., et al., "A Short Conserved Sequence is Involved in the Light–Inductibility of a Gene Encoding Ribulose 1,5–bisphospate Carboxylase Small Subunit of Pea", *Nature*, 315, 280–284, (May 16, 1995).

Morris, G.D., "Ciba–Geigy Enters the $1.5–Billion/Year Corn Biotech Race", *Chemical Week*, (Sep. 12, 1990).

Murphy, D.W., et al., "*Bacillus thuringiensis* Enzyme–Digested Delta Endotoxin: Effect on Cultured Insect Cells", *Science*, 194, 954–956, (Nov. 26, 1976).

Murray, E.E., et al., "Analysis of Unstable RNA Transcripts of Insecticidal Crystal Protein Genes of *Bacillus thuringiensis* in Transgenic Plants and Electroporated Protoplasts", *Plant Molecular Biology*, 16, 1035–1050, (1991).

Nishiitsutsuji–Uwo, J., et al., "Mode of Action of *Bacillus thuringiensis* δEndotoxin: Effect on TN–368 Cells", *Journal of Invertebrate Pathology*, 34, 267–275, (1979).

Ochatt, S.J., et al., "Selection for Salt/Drought Tolerance using Isolated Protoplasts and Protoplast–Derived Calli of Colt Cherry (*Prunus avium x pseudocerasus*)", In: *Progress in Plant Protoplast Research,* Puite, K.J., et al., (eds.), Kluwer Academic Publishers, Dordrecht, The Netherlands, pp. 391–392 (1988).

Oeda, K., et al., "Formation of Crystals of the Insecticidal Proteins of *Bacillus thuringiensis* subsp. *aizawai* IPL7 in *Escherichia coli*", *Journal of Bacteriology,* 171, 3568–3571, (Jun. 1989).

Pang, Y., et al., "Synthesis and Toxicity of Full–Length and Truncated Bacterial CryIVD Mosquitocidal Proteins Expressed in Lepidopteran Cells Using A Baculovirus Vector", *Journal of General Virology,* 73, 89–101, (1992).

Park, W.D., et al., "High–Level, Sucrose–Inducible Expression of a Chimeric Patatin–GUS Gene In Leaf Explants of Transgenic Tobacco Plants", *Journal of Cellular Biochemistry,* 13D, Abstract No. M 343, p. 310, (Mar. 27–Apr. 7, 1989).

Perlak, F.J., et al., "Expression of *Bacillus thuringiensis* Proteins in Transgenic Plants", *In: Biotechnology, Biological Pesticides and Novel Plant–Pest Resistance for Insect Pest Management,* Roberts, D.W., et al., (eds.), Insect Pathology Resource Center, Boyce Thompson Institute for Plant Research, Cornel University, Ithaca, NY, 77–81, (1988).

Perlak, F.J., et al., "Genetically Improved Potatoes: Protection from Damage by Colorado Potato Beetles", *Plant Molecular Biology,* 22, 313–321, (1993).

Perlak, F.J., et al., "Insect Resistant Cotton Plants", *Bio/technology,* 8, 939–943, (Oct. 1990).

Pescitelli, S.M., et al., "Stable Transformation via Electroporation into Maize Type II Callus and Regeneration of Fertile Transgenic Plants", *Plant Cell Reports,* 14, 712–716, (1995).

Poehlman, J.M., et al., In: *Breeding Field Crops, 3rd Edition,* AVI Publishing Company, Inc., Westport, CT, 149–152, (1987).

Poethig, R.S., "Maize—The Plant and Its Parts", In: *Maize for Biological Research,* Sheridan, W.F., (ed.), Plant Molecular Biology Association., Charlottesville, VA, 9–18, (1982).

Porobo–Dessai, A., et al., "Expression of gusA Gene with an Intron in Sweet Potato and Garden Egg Plant", *In Vitro Cellular and Developmental Biology,* 13D, Abstract No. P–1130, p. 123A, (Mar. 1992).

Potrykus, I., et al., "Direct Gene Transfer: State of the Art and Future Potential", *Plant Molecular Biology Reporter,* 3, 117–128, (Summer 1985).

Prakash, C.S., et al., "High Efficiency Transformation and Regeneration of Transgenic Sweetpotato Plants", *In Vitro Cellular and Developmental Biology,* 31, Abstract No. W–17, 28A, (Mar. 1995).

Randolph, L.F., et al., "Developmental Morphology of the Caryopsis in Maize", *Journal of Agricultural Research,* 53, 881–916, (Dec. 15, 1936).

Register III, J.C., et al., "Structure and Function of Selectable and Non–Selectable Transgenes in Maize after Introduction by Particle Bombardment", *Plant Molecular Biology,* 25, 951–961, (1994).

Rhodes, C.A., et al., "Cytogenetic Stability of Aneuploid Maize Tissue Cultures", *Can. J. Genet. Cytol.,* 28, 374–384, (1986).

Rhodes, C.A., et al., "Factors Affecting Tissue Culture Initiation from Maize Tassels", *Plant Science,* 46, 225–232, (1986).

Rice, T.B., "Tissue Culture Induced Genetic Variation in Regenerated Maize Inbreds", Proceedings of the 37th Annual Corn & Sorghum Industry Research Conference, 148–162, (1982).

Rosahl, S., et al., "Expression of a Tuber–Specific Storage Protein In Transgenic Tobacco Plants: Demonstration Of An Esterase Activity", *EMBO. J,* 6, Press Limited, Oxford, England, 1155, (1987).

Ross, M., et al., "Manipulation of the Maize Meristem for Transformation", *In Vitro Cellular and Developmental Biology,* Program Issue, Congress on In Vitro Biology, Abstract No. P–1094, 72A, (May 20–24, 1995).

Roth, B.A., et al., "C1– and R–Dependent Expression of the Maize Bz1 Gene Requires Sequences with Homology to Mammalian myb and myc Binding Sites", *The Plant Cell,* 3, 317–325, (Mar. 1991).

Roth, B.A., et al., "Genetic Regulation of Transient Expression of Maize Anthocyanin Pathway Genes Introduced into Intact Maize Tissues by Microprojectile Bombardment", *Journal of Cellular Biochemistry,* 13D, Abstract No. M 344, p. 310, (Mar. 27–Apr. 7, 1989).

Roush, R.T., et al., "Ecological Genetics of Insecticidal and Acaricide Resistance", *Ann. Rev. Entomol.,* 32, 361–380, (1987).

Rout, J.R., et al., "Agrobacterium–Mediated Gene Transfer to Rice (*Oryza sativa* L.)", *In Vitro Cellular and Developmental Biology,* 31, Abstract No. W–19, 28A, (Mar. 1995).

Russell, J.A., et al., "Physical Trauma and Tungsten Toxicity Reduce the Efficiency of Biolistic Transformation", *Plant Physiol.,* 98, 1050–1056, (1992).

Ryan, A.J., et al., "The Expression of the Napin Gene Under the Control of Its Own Promoter in Transgenic Tobacco Plants", *Journal of Cellular Biochemistry,* 13D, Abstract No. M 345, p. 310, (Mar. 27–Apr. 7, 1989).

Sanford, J.C., "The Biolistic Process", *Plant Physiology,* 89, Abstract No. 9, p. 2, (Apr. 1989).

Sanford, J.C., et al., "Delivery of DNA into Regenerable Tissues of Monocots, Using High–Velocity Microprojectiles", Grant Application No. 86–0183, United States Department of Agriculture, Science and Education, 57 p., (Feb. 27, 1986).

Sass, J.E., "Comparative Leaf Number in the Embryos of Some Types of Maize", *Iowa State Coll. J. Sci.,* 25, 509–512, (1951).

Schafer, W., et al., "T–DNA Integration and Expression in a Monocot Crop Plant after Induction of Agrobacterium", *Nature,* 327, 529–532, (Jun. 11, 1987).

Schardl, C.L., et al., "Design and Construction of a Versatile System for the Expression of Foreign Genes in Plants", *Gene,* 61, 1–11, (1987).

Schnepf, H.E., et al., "Delineation of a Toxin–Encoding Segment of a *Bacillus thuringiensis* Crystal Protein Gene", *The Journal of Biological Chemistry,* 260, 6273–6280, (1985).

Schnepf, H.E., et al., "Specificity–Determining Regions of a Lepidopteran–Specific Insecticidal Protein Produced by *Bacillus thuringiensis*", *The Journal of Biological Chemistry,* 265, 20923–20930, (Dec. 5, 1990).

Scorza, R., et al., "Transformation of Grape (*Vitis vinifera* L.) Somatic Embryos and Regeneration of Transgenic Plants", *Journal of Cellular Biochemistry*, Supplement 18A, Abstract No. X1–310, 102, (Jan. 4–27, 1994).

Sewell, G.H., et al., "Irish Potato, Control of Potato–Infesting Aphids, 1991", *Insecticidal and Acaricide Tests: 1992*, 17, 138–139, (1992).

Sewell, G.H., et al., "Transgenic Potato Plants, Control of Colorado Potato Beetle, 1991", *Insecticidal and Acaricide Tests: 1992*, 17, 138, (1992).

Shaner, D.L., et al., "Mechanism of Action of the Imidazolinones and Cell Culture Selection of Tolerant Maize", In: *Biotechnology in Plant Sciences*, Zaitlin, M., et al., (eds.), Academic Press, Orlando, FL, 287–299, (1985).

Sharman, B.C., "Developmental Anatomy of the Shoot of *Zea mays* L.", *Annals of Botany*, VI, 246–281, (Apr. 1942).

Shatters, Jr., R.G., et al., "Particle Gun Bombardment of Embryogenic Bahiagrass Callus Culture", *Journal of Cellular Biochemistry*, Supplement 18A, Abstract No. X1–311, 102, (Jan. 4–23, 1994).

Shields, R., "Towards Insect–Resistant Plants", *Nature*, 328, 12–13, (Jul. 2, 1987).

Shivakumar, A.G., et al., "Vegetative Expression of the δ–Endotoxin Genes of *Bacillus thuringiensis* subsp. *kurstaki* in *Bacillus subtilis*", *Journal of Bacteriology*, 166, 194–204, (Apr. 1986).

Smith, G.E., et al., "Molecular Engineering of the *Autographa californica* Nuclear Polyhedrosis Virus Genome: Deletion Mutations Within the Polyhedrin Gene", *Journal of Virology*, 46, 584–593, (May 1983).

Somers, D.A., et al., "In Vitro Selection for Herbicide Tolerance in Maize", In: *Biotechnology in Agriculture and Forestry*, 25, Maize, Bajaj, Y.P.S., (ed.), Springer–Verlag, Berlin, 21 p., (1994).

Sorenson, K.A., et al., "Colorado Potato Beetle Control with Bioinsecticides, 1991", *Insecticide and Acaricide Tests: 1992*, 17, 139, (1992).

Spangenberg, G., et al., "Gene Transfer and Regeneration of Transgenic Plants in Forage Grasses", *Journal of Cellular Biochemistry*, Supplement 18A, Abstract No. X1–312, p. 102, (Jan. 4–23, 1994).

Spencer, T.M., et al., "Characterization of Transgene Insertion and Expression in a Glufosinate–Resistant Maize Line", *In Vitro Cellular and Developmental Biology*, 31, Program Issue, Congress on In Vitro Biology, Abstract No. P–1096, 72A, (May 20–24, 1995).

Spencer, T.M., et al., "Production of Fertile Transgenic Maize by Electroporation", *In vitro Cellular and Developmental Biology*, Program Issue, Congress on Tissue and Cell Culture, Abstract No. P–11, 34, (Jun. 4–7, 1994).

St. Julian, G., et al., "Bacteria, Spirochetes, and Rickettsia as Insecticides", *Annals of the New York Academy of Sciences*, 217, 65–75, (1973).

Stolle, C.A., et al., "Cellular Factor Affecting the Stability of β–globulin mRNA", *gene*, 62, 65–74, (1988).

Strauch, E., et al., "Cloning of a Phosphinothricin N–Acetyltransferase Gene from *Streptomyces Viridochromogenes*Tu494 and its Expression in *Streptomyces lividans* and *Escherichia coli*", *Gene*, 63, 65–74, (1988).

Stroo, H.F., et al., "Heterotrophic Nitrification in an Acid Forest Soil and by an Acid–Tolerant Fungus", *Applied and Environmental Microbiology*, 52, 1107–1111, (Nov. 1986).

Sukhapinda, K., et al., "Maize Haploid Protoplast Transformation and Regeneration of Transgenic Plants", *In Vitro Cellular and Developmental Biology*, 28, Abstract No. P–1132, p. 123A, (Mar. 1992).

Suprasanna, P., et al., "Plantlet Regeneration from Glume Calli of Maize (*Zea mays* L.)", *Theor. Appl. Genet.*, 72, 120–122, (1986).

Teeri, T.H., et al., "Mendelian Inheritance of Transgenes in Barley", *Journal of Cellular Biochemistry*, Supplemental 18A, Abstract No. X1–313, p. 102, (Jan. 4–23, 1994).

Thomas, W.E., et al., "Mechanism of Action of *Bacillus thuringiensis* var *israelensis* Insecticidal δ–Endotoxin", *FEBS Letters*, 154, 362–368, (Apr. 1983).

Tojo, A., et al., "Dissolution and Degradation of *Bacillus thuringiensis* δ–Endotoxin by Gut Juice Protease of the Silkworm *Bombyx mori*", *Applied and Environmental Microbiology*, 45, 576–580, (Feb. 1983).

Tomes, D.T., "Cell Culture, Somatic Embryogenesis and Plant Regeneration in Maize, Rice, Sorghum and Millets", In: *Cereal Tissue and Cell Culture*, Bright, S.W.J., et al., (eds.), Martinus Nijnoff/Dr. W. Junk, Amsterdam, The Netherlands, 175–203, (1985).

Tomes, D.T., "Initiation of Embryogenic Callus Cultures from Immature Embryos of Elite Corn (*Zea mays* L.) Germplasm", *In Vitro*, 20, Abstract No. 146, p. 276, (Mar. 1984).

Tomes, D.T., et al., "The Effect of Parental Genotype on Initiation of Embryogenic Callus from Elite Maize (*Zea mays* L.) Germplasm", *Theor. Appl. Genet.*, 70, 505–509, (1985).

Torne, J.M., et al., "Regeneration of Plants from Mesocotyl Tissue Cultures of Immature Embryos of *Zea mays* L.", *Plant Science Letters*, 17, 339–344, (1980).

Townsend, J.A., et al., "Factors Which Influence the Agrobacterium–Mediated Transformation of Soybean", *Journal of Cellular Biochemistry*, Supplement 18A, Abstract No. X1–104, 78, (Jan. 4–23, 1994).

Vaeck, M., et al., "*Bacillus thuringiensis* Endotoxin Gene Expression and Insect Resistance in Higher Plants", *Pesticide Science*, 20, 319–320, (1987).

Vaeck, M., et al., "Engineering Improved Crops for Agriculture: Protection from Insects and Resistance to Herbicides", In: *Plant Gene Systems and Their Biology*, Key, J.L., et al., (eds.), Alan R. Liss, Inc., New York, 171–181, (1987).

Vaeck, M., et al., "Engineering of Insect Resistant Plants Using a *B. thuringiensis* Gene", *In: Molecular Strategies for Crop Protection*, New York, Alan R. Liss, Inc., 355–366, (1987).

Vaeck, M., et al., "Insect Resistance in Transgenic Plants Expressing *Bacillus thuringiensis* Toxin Gens", *An. Soc. Entomol. Brasil*, 16, 427–435, (1987).

Vaeck, M., et al., "Protein Engineering in Plants: Expression of *Bacillus thuringiensis* Insecticidal Protein Genes", *Cell Culture and Somatic Cell Genetics of Plants*, 6, 425–439, (1989).

Vaeck, M., et al., "Transgenic Plants Protected from Insect Attack", *Nature*, 328, 33–37, (Jul. 2, 1987).

van den Elzen, P.J., et al., "A Chimaeric Hygromycin Resistance Gene as a Selectable Marker in Plant Cells", *Plant Molecular Biology*, 5, 299–302, (1985).

van den Elzen, P.J., et al., "Simple Binary Vectors for DNA Transfer to Plant Cells", *Plant Molecular Biology*, 5, 149–154, (1985).

Van Lammeren, A.A., "Developmental Morphology and Cytology of the Young Maize Embryo (*Zea mays* L.)", *Acta Bot. Neerl.*, 35, 169–188, (Aug. 1986).

Vasil, I.K., "Isolation and Culture of Protoplasts of Grasses", *International Review of Cytology, Supplement 16*, Bourne, G.H., et al., (eds.), Academic Press, New York, 79–88, (1983).

Vasil, I.K., et al., "Molecular Genetic Improvement of Wheat", *Journal of Cellular Biochemistry*, Supplement 18A, Abstract No. X1–105, p. 78, (Jan. 4–23, 1994).

Vasil, I.K., et al., "Molecular Improvement of Cereals", *Plant Molecular Biology*, 25, 925–937 (1994).

Vasil, V., et al., "Histology of Somatic Embryogenesis in Cultured Immature Embryos of Maize (*Zea mays* L.)", *Protoplasma*, 127, 1–8, (1985).

Visser, B., et al., "Transgenic Tobacco Plants Expressing a Modified *Bacillus thuringiensis* cryIC Gene", *Journal of Cellular Biochemistry*, Supplement 16F, Abstract No. Y 136, p. 213, (Apr. 3–16, 1992).

Wan, Y., et al., "Development and Use of an Efficient Transformation System for Barley", *Journal of Cellular Biochemistry*, Supplement 18A, Abstract No. X1–013, 78, (Jan. 4–23, 1994).

Wan, Y., et al., "Efficient Production of Transgenic Barley Plants and Analysis of Transgene Expression in Progeny", *In Vitro Cellular and Developmental Biology*, 30A, Program Issue Congress on Cell and Tissue Culture, Abstract P–10, 34, (Jun. 4–7, 1994).

Wan, Y., et al., "Type 1 Callus as a Bombardment Target for Generating Fertile Transgenic Maize (*Zea mays* L.)", *Planta*, 196, 7–14, (1995).

Warren, G.W., et al., "Field Evaluation of Transgenic Tobacco Containing a *Bacillus thuringiensis* Insecticidal Protein Gene", *Journal of Economic Entomology*, 85, 1651–1659, (1992).

Watson, S.A., "Corn Marketing, Processing and Utilization", *In: Corn and Corn Improvement*, 3rd Edition, Sprague, G.F., et al., (eds.), American Society of Agronomy, Inc., et al., Madison, WI, 881–939, (1988).

Webb, R.P., et al., "Superoxide Dismutase Gene Expression in Transgenic Plants,", *Journal of Cellular Biochemistry*, Supplement 16F, Abstract No. Y 137, 213, (Apr. 3–16, 1992).

Weck, E., "Are Colorized DNA Sequences an Application of Fuzzy Logic?", Abstracts, 35th Annual Maize Genetics Conference, St. Charles, IL, Poster No. 45, p. 45 (Mar. 18–21, 1993).

Weigel, Jr., R.C., et al., "Somatic Embryogenesis in Barley", *In Vitro*, 20, Abstract No. 147, p. 277, (Mar. 1984).

Weissinger, A., et al., "Maize Transformation via Microprojectile Bombardment", *In: Genetic Improvements of Agriculturally Important Crops*, Fraley, R.T., et al., (eds.), Cold Spring Harbor Laboratory, Cold Spring Harbor, NY, 21–25, (1988).

Weissinger, A., et al., "Microprojectile Bombardment for Maize Transformation", *In Vitro Cellular and Developmental Biology*, 23, Program Issue, 38th Annual Meeting of the Tissue Culture Association, Washington, D.C., Abstract No. 254, (Mar. 1987).

Wernicke, W., et al., "Adventitious Embryoid and Root Formation from Rice Leaves", *Z. Pflanzenphysiol. Bd.*, 103, 361–365, (1981).

White, D.W., et al., "Auxin–Inducible Response Promoter Elements", *Journal of Cellular Biochemistry*, Supplement 16F, Abstract No. Y 138, p. 213, (Apr. 3–16, 1992).

Williams, R., et al., "Expression of the Maize Homeobox Gene Knotted–1 in Transgenic Maize", Abstracts, 35th Annual Maize Genetics Conference, St. Charles, IL, Poster No. 47, p. 46 (Mar. 18–21, 1993).

Williams, S., et al., "Chemical Regulation of *Bacillus thuringiensis* δ–Endotoxin Expression in Transgenic Plants", *Bio/technology*, 10, 540–543, (May 1992).

Wilson, F.D., et al., "Resistance of Cotton Lines Containing a *Bacillus thuringiensis* Toxin to Pink Bollworn (*Lepidoptera: Gelechiidae*) and Other Insects", *J. Econ. Entomol.*, 85, 1516–1521, (1992).

Wilson, H.M., et al., "Maize", In: *Transformation of Plants and Soil Microorganisms*, Wang, K., et al., (eds.), Cambridge University Press, New York, 65–80, (1995).

Withers, L., et al., "Proline: A Novel Cryoprotectant for the Freeze Preservation of Cultured Cells of *Zea mays* L.", *Plant Physiology*, 64, 675–678, (1979).

Witt, D.P., et al., "Cytotoxicity of *Bacillus thuringiensis* 67 –Endotoxins to Cultured Cf–1 Cells Does Not Correlate with In Vivo Activity Toward Spruce Budworm Larvae", *In: Fundamental and Applied Aspects of Invertebrate Pathology*, Samson, R.A., et al., (eds.), Fourth International Colloquium of Invertebrate Pathology, Wangingen, The Netherlands, 3–6, (Aug. 18–22, 1986).

Wohllenben, W., et al., "Nucleotide Sequence of the Phosphinothricin N–Acetyltransferase Gene from *Streptomyces viridochromogenes* Tü494 and Its Expression in *Nicotania tabacum*", *Gene*, 70, 25–37, (1988).

Wong, J.R., et al., "Anthocyanin Regulatory Genes from Maize (B–Peru and C1) Activate the Anthocyanin Pathway in Wheat, Barley and Oat Cells", *Journal of Cellular Biochemistry, Supplement 15A*, p. 159, (1991).

Wood, M., "Blast Those Genes!", *Agricultural Research*, 2 p., (Jun. 1989).

Wu, S., et al., "Characterization of Chitinase cDNA Clones for Acidic and Basic Isoforms of Maize", Abstracts, 35th Annual Maize Genetics Conference, St. Charles, IL, Poster No. 48, p. 46 (Mar. 18–21, 1993).

Wyatt, S.D., et al., "Coat Protein Gene–Mediated Resistance to Barley Yellow Dwarf Virus in Maize and Barley", *Phytopathology*, 83, Abstract No. A392, 1374, (Dec. 1993).

Xiayi, K., et al., "Electroporation of Immature Maize Zygotic Embryos and Regeneration of Transgenic Plants", *Transgenic Research*, 5, 219–221, (1996).

Yoshiba, Y., et al., "Correlation Between the Induction of a Gene for $\Delta^1$–Pyrroline–5–Carboxylate Synthetase and the Accumulation of Proline in *Arabidopsis thaliana* under Osmotic Stress", *The Plant Journal*, 7, 751–760 (1995).

Zhang, W., et al., "Analysis of Rice Actl 5' Region Activity in Transgenic Rice Plants and the Study of Regulatory Elements in This Region", *Journal of Cellular Biochemistry*, Supplement 16F, Abstract No. Y 139, p. 213, (Apr. 3–16, 1992).

Beauregard et al. Bio/technology vol. 13 pp. 974–981, Sep. 13, 1995.

Armstrong, C.L., "Regeneration of Plants from Somatic Cell Cultures: Applications for in vitro Genetic Manipulation", In: *The Maize Handbook*, Freeling, M., et al., (eds.), Springer–Verlag, Inc., New York, 663–671, (1994).

Raineri, D.M., et al., "VirA, the Plant–Signal Receptor, is Responsible for the Ti Plasmid–Specific Transfer of DNA to Maize by Agrobacterium", *Proc. Natl. Acad. Sci. USA,* 90, 3549–3553, (Apr. 1993).

Specification of U.S. Patent Application, Serial No. 07/205, 155, entitled "Stable Transformation of Plant Cells," pp. 1–29 (Filed Jun. 1988).

Charest, et al., "Factors Affecting the Use of Chloramphenicol Acetyltransferase as a Marker for Brassica Genetic Transformation", *Plant Cell Reports,* 7, 628–631 (1989).

Herrera–Estrella, et al., "Use of Reporter Genes to Study Gene Expression in Plant Cells", In: *Plant Molecular Biology Manual B1,* Kluwer Academic Publishers, Dordrecht, pp. 1–22 (1988).

Johri, et al., "Genetic Approaches to Meristem Organization", In: *Maize for Biological Research,* W. F. Sheridan, (ed.), Plant Molecular Biology Association, pp. 301–310 (1982).

Abstracts, 35th Annual Maize Genetics Conference, *In Vitro Cellular and Devel. Biol.,* 28:(3)(1992).

""Bullets" Transform Plant Cells," *Agricell Report,* 9, 5, (Jul. 1987).

"BioTechnica Applies for Field Test of Genetically Engineered Corn," *Genetic Technology News,* 10(3), (Mar. 1990).

Catalog, *Handbook of Fine Chemicals,* Aldrich Chem. Co., p. 508 (1988).

"Chipping Away at Old Weed Enemies," Farm Science Outlook, *Prairie Farmer* 162, 34 (Feb. 20, 1990).

"Corn Transformers Multiply," *Bio/Technol.,* 8, 490 (Jun. 1990).

"Cornell U. Gene Gun Hits Biotech Bullseye," *Agriculture Technology,* p. 13.

"Dalapon," Merck Index, 11th edition, S. Budavae, (ed.), Merck and Co., pp. 405–406 (1989).

"Dekalb Researchers Produce Fertile Corn Plants with Foreign Genes," *ARI Newsletter* (Oct./Nov. 1990).

Dialog Search of Japanese Patent No. 61–134343 (1986).

EPO Notice Regarding Publication of Bibliographic Data for EPO 0485506 (1992).

"Gene Guns Succeed in Altering Corn," *Biotechnology News,* p. 2 (Apr. 1990).

"Genetic Enginering Advance Announced for Corn Plants," *Investor's Daily,* (Apr. 19, 1990).

"Genetically Engineered Corn: Breakthrough Brings Market Closer," *Genetic Technology News,* 8–11 (Oct. 1990).

"Herbicide–Resistant Corn" *CT Academy of Science and Engineering, Case Reports,* 5(4), 6 (1990).

International Search Report, PCT/US 90/04462, mailed Jan. 15, 1991.

International Search Report, PC/US 90/09699, mailed Aug. 16, 1995.

International Society for Plant Molecular Biology, Program and Abstracts, Molecular Biology of Plant Growth and Development, Tuscon, Arizona, Oct. 6–11 (1991).

"Keystone Crops," *Agricultural Genetics Report,* (Mar./Apr. 1990).

Patent Family Record for Australian Patent 87 80 893.

"Plant Science Research, Inc. Achieves Successful Transformation of Corn," *Genetic Engineering News,* 10(3), 3 (Mar. 1990).

"Shotgunning DNA into Cells," *Genetic Engineering News,* (Jul./Aug. 1987).

"Sticky Ends," *Genetic Engineering News,* 10(5), 1 (May 1990).

"Teams from USDA/Monsanto and DeKalb Genetically Engineer Corn," *Genetic Technology News,* 10(5) (May 1990).

"Two Teams Succeed in Putting Foreign Genes in Corn Plants," *Genetic Engineering Letter,* 10(8), 3 (Apr. 24, 1990).

"USDA Approves More Field Tests," *Genetic Technology News,* 11(7), 12 (Jul. 1991).

"USDA Approves Field Test for BioTechnica's Genetically Engineered Corn," *Genetic Technology News,* 10(7), 6 (Jul. 1990).

Adang, M. J., et al., "Characterized Full–Length and Truncated Plasmid Clones of the Crystal Protein of *Bacillus thuringiensis* subsp. *Kurstaki* HD–73 and Their Toxicity to *Manduca sexta,*" *Gene,* 36, 289–300 (1985).

Ahokas, H., "Transfection of Germinating Barley Seed Electrophoretically with Exogenous DNA," *Theor. Appl. Genet.,* 77, 469–472 (1989).

Ahokes, H. "Electrophoretic transfection of cereal grains with exogenous nucleic acid," Soc. Biochem. Biophys. Microbio. Fen., Biotieteen Paivat (Bioscience Days), Abstracts, Technical University of Helsinki, Espoo, p. 2 (1989).

Akella, V., et al., "Expression in Cowpea Seedings of Chimeric Transgenes after Electroporation into Seed- –Derived Embryos," *Plant Cell Rep.,* 12, 110–117 (1993).

Altenbach, S.B., et al., "Enhancement of the Methionine Content of Seed Proteins by the Expression of a Chimeric Gene Encoding a Methionine–Rich Protein in Transgenic Plants," *Plant. Mol. Biol.,* 13, 513–522 (1989).

Altenbach, S.B., et al., "Cloning and Sequence Analysis of a cDNA Encoding a Brazil Nut Protein Exceptionally Rich in Methionine," *Plant Mol. Biol.,* 8, 239–250 (1987).

Ampe, C., et al., "The Amino–Acid Sequence of the 2S Sulphur–Rich from Seed of Brazil Nut (*Bertholletia excelsa* H.B.K.)," *Eur. J. Biochem.,* 159, 597–604 (1986).

Armstrong, C. L., et al., "Establishment and Maintenance of Friable, Embryogenic Maize Callus and the Involvement of L–Proline," *Planta,* 164, 207–214 (1985).

Armstrong, C.L., et al., "Genetic and cytogenetic variation in plants regenerated from organogenic and friable, embryonic tissue cultures of maize," *Biological Abstracts,* vol. 85, Abstract No. 117662 (1988).

Aves, K., et al., Transformation of an Elite Maize Inbred Through Microprojectile Bombardment of Regenerable Embryonic Callus, *In Vitro Cell. Develop. Biol.,* 28A, p. 124A, Abstract No. P–1134 (1992).

Bao–Jian, L., et al., "Introduction of Foreign Genes into the Seed Embryo Cells of Rice by Electroinjection and the Regeneration of Transgenic Rice Plants," *Science in China,* 34, 925–931 (1991).

Barker, R.F., et al., "Nucleotide Sequence of the T–DNA Region from the *Agrobacterium tumefaciens* Octopone Ti Plasmid pTi15955," *Plant Mol. Biol.,* 2, 335–350 (1983).

Beerman, F., et al., "Tyrosinase as a Marker for Transgenic Mice," *Nuc. Acids, Res.,* 19, 958 (1991).

Belanger, F. C., et al., "Molecular Basis for Allelic Polymorphism of the Maize Globulin–1 Gene" *Genetics,* 129, 863–872 (1991).

Benner, M.S., et al., "Genetic Analysis of Methionine–Rich Storage Protein Accumulation in Maize," *Theor. Appl. Genet.,* 78, 761–767 (1989).

Bevan, M., et al., "A Chimaeric Antibiotic Resistance Gene as a Selectable Marker for Plant Cell Transformation," *Nature*, 304, 184–187 (1983).

Bevan, M., et al., "Structure and Transcription of the Nopaline Synthase Gene Region of T–DNA," *Nuc. Acids Res.*, 11, 369–385 (1983).

Binns, A N., "Agrobacterium–mediated gene delivery and the biology of host range limitations," *Physiologia Plantarum*, 79, 135–139 (1990).

Bishop, J. E., "Two Teams Plane Genes into Corn," *The Wall Street Journal*, B1 (Apr. 1990).

Bohnert, H. J., "Coping with Water Deficit—Application of Biochemical Principles," 1995 Plant Physiology Meeting, Abstract No. 20003 (1995).

Bohnert, H.J., et al., "Adaptations to Environmental Stresses," *The Plant Cell*, 7, 1099–1111 (1995).

Booy, G., et al., "Attempted Pollen–Mediated Transformation of Maize," *J. Plant Physiol.*, 135, 319–324 (1989).

Boulton, M. I., et al., "Specificity of Agrobacterium–mediated delivery of maize streak virus DNA to members of the Gramineae," *Plant Molecular Biology*, 12, 31–40 (1989).

Boyer, J. S., "Water Deficits and Photosynthesis," In: *Water Deficits and Plant Growth*, vol. IV, Kozlowski, T. T., (ed.), Academic Press, New York pp. 153–190 (1976).

Brill, W. J., "Agricultural Microbiology," *Scientific American*, 245(3), 199–215 (Sep. 1981).

Brunke, K. J., et al., "Insect Control with Genetically Engineered Crops," *Trends in Biotechnol.*, 9, 197–200 (1991).

Buchanan–Wollaston, V., et al., "Detoxification of the Herbicide Dalapon by Transformed Plants," *J. of Cell. Biochem.*, 13D, p. 330, Abstract No. M503 (1989).

Caliguri, M. G., et al., "Identification of Amino Acid Residues Involved in Feedback Regulation of the Anthranilate Synthase Complex from *Salmonella typhimurium*," *J. Biol. Chem.*, 266, 8328–8335 (1991).

Callis, J., et al., "Introns Increase Gene Expression in Cultures Maize Cells," *Genes and Development*, 1, 1183–1200 (1987).

Cao, J., et al., "Transformation of Rice and Maize Using the Biolistic Process," In:*Plant Gene Transfer*, Alan R. Liss, Inc., pp. 21–33 (1990).

Carpita, N. C., "The Biochemistry of "Growing" Cell Walls," In: *Physiology of Cell Expansion During Plant Growth*, Cosgrove, D. J., et al., (eds.) Am. Soc. Plant Physiol., pp. 28–100 (1987).

Chan, M.–T., et al., "Agrobacterium–Mediated Production of Transgenic Rice Plants Expressing a Chimeric α–Amylase Promoter/β–Glucuronidase Gene," *Plant Molecular Biology*, 22, 491–506 (1993).

Chandler, V. L., et al., "Two Regulatory Genes of the Maize Anthocyanin Pathway are Homologous: Isolation of B Utilizing R Genomic Sequences," *The Plant Cell*, 1, 1175–1183 (1989).

Chasan, R., "Transforming Maize Transformation," *The Plant Cell*, 4, 1463–1464 (1992).

Chourey, P. S., et al., "Callus Formation from Protoplasts of a Maize Cell Culture," *Theor. Appl. Genet.*, 59, 341–344 (1981).

Christou, P., et al., "Opine Synthesis in Wild–Type Plant Tissue," *Plant Physiol.*, 82, 218–221 (1986).

Christou, P., et al., "Soybean Genetic Engineering—Commercial Production of Transgenic Plants," *Trends Biotechnol.*, 8, 145–151 (1990).

Christou, P., et al., "Cotransformation Frequencies of Foreign Genes in Soybean Cell Cultures," *Theor. Appl. Genet.*, 79, 337–341 (1990).

Christou, P., et al., "Genetic Transformation of Crop Plants Using Microprojectile Bombardment," *The Plant Journal*, 2, 275–281 (1992).

Christou, P., et al., "Stable Transformation of Soybean Callus by DNA–Coated Gold Particles," *Plant Physiol.*, 87, 671–674 (1988).

Chu, C.–C., et al., "Establishment of an Efficient Medium for Anther Culture of Rice Through Comparative Experiments on the Nitrogen Sources," *Sci Sin. (Peking)*, 13, 659–668 (1975).

Clark, B., "Biotech Advance in Corn: Gunslinging Researchers Fire Marker Genes in to Corn," *AG Consultant*, 46(7), 12 (Jul. 1990).

Cocking, F., et al., "Gene Transfer in Cereals," *Science*, 236, 1259–1262 (1987).

Coe et al., "The Genetics of Corn" In: *Corn and Corn Improvement*, 2nd edition, Sprague, G. F., (ed.), American Soc. Agromony, Inc, Madison, WI, p. 138 (1977).

Comai, L., et al., "Expression in Plants of a Mutant aroA Gene from *Salmonella typhimurium* Confers Tolerance to Glyphosate," *Nature*, 317, 741–744 (Oct., 1985).

Creissen, G., et al., "Agrobacterium– and Microprojectile––Mediated Viral DNA Delivery into Barley Microspore Derived–Cultures," *Plant Cell Rep.*, 8, 680–683 (Apr. 1990).

Crossway, A., et al., "Integration of foreign DNA following microinjection of tobacco mesophyll protoplasts," *Mol. Gen. Genet.*, 202, 179–185 (1986).

D'Halluin, K., et al., "Transgenic Maize Plants by Tissue Electroporation," *The Plant Cell*, 4, 1495–1505 (1992).

Darvill, A., et al., "The Primary Cell Walls of Flowering Plants," In: *The Biochemistry of Plants*, vol. 1, pp. 91–162 (1980).

Dauce–LeReverand, B., et al., "Improvement of *Escherichia coli* Strains Overproducing Lysine Using Recombinant DNA Techniques," *Eur. J. Appl. Microbiol. Biotechnol.*, 15, 227–231 (1982).

DeBlock, M., et al., "Engineering herbicide resistance on plants by expression of a detoxifying enzyme," *EMBO J.*, 6, 2513–2518 (1987).

De Greef, W., et al., "Evaluation of herbicide resistance in transgenic crops under field conditions," *Bio/Technol.*, 7, 61–64 (1989).

Dekeyser, R. A., et al., "Evaluation of Selectable Markers for Rice Transformation," *Plant Physiol.*, 90, 217–223 (1989).

Dekeyser, R. A., et al., "Transient Gene Expression in Intact and Organized Rice Tissues," *The Plant Cell*, 2, 591–602, (1990).

DeWald et al., "Plant regeneration from inbred maize suspensions," VIIth International Congress on Plant Tissue and Cell Culture, p. 12, Abstract No. A1–36 (Jun. 24–29, 1990).

DeWet, J. M. J.,et al.; "Exogenous gene transfer in maize (*Zea mays*) using DNA–treated pollen;" In: *The experimental manipulation of ovule tissues.* Chapman, G.P., et al., (eds.), Longman, New York, pp. 197–209 (1985).

DeWet, J. R. et al., "Cloning of Firefly Luciferase cDNA and the Expression of Active Luciferase in *Escherichia coli*," *Proc. Nat. Acad. Sci. USA*, 82, 7870–7873 (1985).

Donn, G., et al., "Stable Transformation of Maize with a Chimaeric, Modified Phosphinothricin–Acetyltransferase Gene from *Streptomyces viridochromogenes*," Abstracts, VIIth International Congress Plant Tissue Cell Culture, p. 53, Abstract No. A2–38 (Jun. 24–29, 1990).

Dupuis, I., et al., "Gene Transfer to Maize Male Reproductive Structure by Particle Bombardment of Tassel Primordia," *Plant Cell Rep.*, 12, 607 (1993).

Ellis, J. G., et al., "Does the OCS–Element Occur as a Functional Component of the Promotors of Plant Genes?" *EMBO J.*, 6, 3203–3208 (1987).

Evans, D. A., et al., "Somaclonal Variation—Genetic Basis and Breeding Applications," *Trends Genet.*, 5, 46–50 (1989).

Fennel, A., et al., "Electroporation and Peg Delivery of DNA into Maize Microspores," *Plant Cell Reports*, 11, 567–570 (1992).

Finnegan, J., et al., "Transgene Inactivation: Plants Fight Back!" *Bio/Technol.*, 12, 883–888 (Sep., 1994).

Fitzpatrick, T., "Pleiotrophic Gene Found in Barley Plant," *Genetic Engineering News*, 13, 1 (1993).

Fransz, P., et al., "Cytodifferentiation during callus initiation and somatic embryogenesis in *Zea mays* L.," Ph.D. thesis, U. of Wageningen Press, The Netherlands (1988).

Freeling, J.C., et al., "Developmental Potentials of Maize Tissue Cultures," *Maydica*, XXI, 97–112 (Jul. 1977).

Freiberg, "More Researchers Discover Corn Transformation Technology," *AG Biotechnology News*, p. 26 (1990).

Fromm, M. E., et al., "Inheritance and Expression of Chimeric Genes in the Progeny of Transgenic Maize Plants," *Bio/Technol.*, 8, 833–839 (1990).

Fromm, M. E., et al., "Stable Transformation of Maize after Gene Transfer by Electroporation," *Nature*, 319, 791–793 (1986).

Fromm, M., et al., "Expression of Genes Transfected into Monocot and Dicot Plant Cells by Electroporation," *Proc. Nat. Acad. Sci. USA*, 82, 5824–5828 (1985).

Fry, S.C., "Introduction to the Growing Cell Wall," In: *The Growing Plant Cell Wall: Chemical and Metabolic Analysis*, Longman Scientific and Technical, New York, pp. 1–5, 102–109 (1988).

Geiser, M., et al., "The Hypervariable Region on the Genes Coding for Entomopathogenic Crystal Proteins of *Bacillus thuringiensis*: Nucleotide Sequence of the kurhd1 gene of subsp. kurstaki HD1," *Gene*, 48, 109–118 (1986).

Goff, S. A., et al., "Plant Regeneration of Anthocyanin Biosynthetic Genes Following Transfer of B Regulatory Genes into Maize Tissues," *EMBO J.*, 9, 2517–2522 (1990).

Gordon, Kamm, W. J., et al., "Stable Transformation of Embryonic Maize Cultures by Microprojectile Bombardment," *J. Cellular Biochem.*, 13D, p. 259, Abstract No. M122 (1989).

Gordon–Kamm, W.J., et al., "Transformation of Maize Cells and Regeneration of Fertile Transgenic Plants," *The Plant Cell*, 2, 603–618 (1990).

Gould, J., et al., "Transformation of the Graminae by *Agrobacterium tumefaciens*," Int. Soc. Plant Mol. Biol. 3rd Int. Congress, Abstract No. 1277 (1991).

Gould, O., et al., "Shoot Tip Culture as a Potential Transformation System," Abstracts, Beltwide cotton production research conferences, New Orleans, LA, p. 91 (1988).

Gould, J., et al., "Transformation of *Zea mays* L. Using *Agrobacterium tumefaciens* and the Shoot Apex," *Plant Physiol.*, 95, 426–434 (1991).

Graves, A., et al., "The transformation of *Zea mays* seedlings with *Agrobacterium tumefacians*," *Plant Mol. Biol.*, 7, 43–50 (1986).

Green, C., et al., "Plant Regeneration from Tissue Cultures of Maize," *Crop. Sci.*, 15, 417–421 (1975).

Green, C., et al., "Plant Regeneration in Tissue Cultures of Maize," In: *Maize for Biological Research*, Sheridan, W. F., (ed.) Plant Mol. Biol. Assoc., pp. 367–372 (1982).

Green, C., et al., "Somatic Cell Genetic Systems in Corn," In: *Advances in Gene Technology: Molecular Genetics of Plant and Animals*, Academic Press, Inc., pp. 147–157 (1983).

Grimsley, N., et al., "DNA Transfer from Agrobacterium to *Zea mays* or Brassica by Agroinfection is Dependent on Bacterial Virulence Functions," *Mol. Gen. Genet.*, 217, 309–316 (1989).

Gritz, L., et al., "Plasmid–Encoded Hygromycin B Resistance: The Sequence of Hygromycin B Phosphotransferase Gene and Its Expression in *Escherichia coli* and *Saccharomyces cerevisiae*," *Gene*, 25, 179–188 (1983).

Guerineau, F., et al., "Sulfonamide Resistance Gene for Plant Transformation," *Plant Molecular Biology*, 15, 127–136 (1990).

Guilley, H., et al., "Transcription of Cauliflower Mosaic Virus DNA: Detection of Promoter Sequences, and Characterization of Transcripts," *Cell*, 30, 763–773 (Oct. 1982).

Gunset, G., "Genetic Advance May Transform Corn," *Chicago Tribune* (Apr. 19, 1990).

Gunset, G., "Corn Farmers See Economic, Environmental Gold in Designer Genes," *Chicago Tribune* (Jan. 21, 1991).

Hallauer, A. R., et al., "Corn Breeding," In: *Corn and Corn Improvement*, 3rd edition, Sprague, G. F., et al., (eds.), Agronomy Soc. Amer., pp. 463–564 (1988).

Haughn, G. W., "Transformation with a Mutant Arabidopsis Acetolactate Synthase Gene Renders Tobacco Resistant to Sulfonylurea Herbicides," *Mol. Gen. Genet.*, 211, 266–271 (1988).

Hautpman, R. M., et al., "Evaluation of Selectable Markers for Obtaining Stable Transformants on the Gramineae," *Plant Physiol.*, 86, 602–606 (1988).

Hiel, Y., et al., "Efficient Transformation of Rice (*Oryza sativa* L.) Mediated by Agrobacterium and Sequence Analysis of the Boundaries of the T–DNA," *The Plant Journal*, 6, 271–282 (1994).

Hoffman, L. M., et al., "A Modified Storage Protein is Synthesized, Processed, and Degraded in the Seeds of Transgenic Plants," *Plant Mol. Biol.*, 11, 717–729 (1988).

Hoffman, L. M., et al., "Synthesis and Protein Body Deposition of Maize 15kD Zein in Transgenic Tobacco Seeds," *EMBO J.*, 6, 3213–3221 (1987).

Hofte, H., et al., "Insecticidal Crystal Proteins of *Bacillus thuringiensis*," *Microbiol. Rev.*, 53, 242–255 (1989).

Hong, B., et al., "Developmental and Organ–Specific Expression of an ABA– and Stress–Induced Protein in Barley," *Plant Mol. Biol.*, 18, 663–674 (1992).

Hooykaas, P. J. J., "Transformation of plant cell via Agrobacterium," *Plant Mol. Biol.*, 13, 327–336 (1989).

Horn, M., et al., "Transgenic Plants of Orchard Grass (*Dactylis glomerata* L.) from Protoplasts," *Chem. Abstracts*, 110, p. 208, Abstract No. 89869a (1989).

Horn, M., et al., "Transgenic Plants of Orchardgrass (*Dactylis glomerata* L.) from Protoplasts," *Plant Cell Reports*, 7, 469 (1988).

Howe, A., et al., "Development of Glyphosphate as a Selectable Marker for the Production of Fertile Transgenic Corn Plants," *In Vitro Cell. Develop. Biol.,* 28A, p. 124A, Abstract No. P–1136 (Jul.–Aug. 1992).

Huang, Y., et al., "Factors Influencing Stable Transformation of Maize Protoplasts by Electroporation," *Plant Cell, Tissue and Organ Culture,* 18, 281 (1989).

Imbrie–Milligan, C., et al., "Microcallus Growth from Maize Protoplasts," *Planta,* 171, 58–64 (1987).

Jahne, A., et al., "Regeneration of Fertile Plants from Protoplasts Derived from Embryogenic Cell Suspensions of Barley (*Hordeum vulgare* L.)," *Plant Cell Rep.,* 10, 1–6 (1991).

Jayne, S., et al., "Analysis of Elite Transgenic Maize Plants Produced by Microprojectile Bombardment," Program and Abstracts, Int. Soc. for Plant Mol. Biol., 3rd Int. Cong., Abstract No. 338 (Oct. 6–11, 1991).

Jefferson, R,. et al., "β–Glucuronidase from *Escherichia coli* as a Gene–Fusion Marker," *Proc. Nat Acad. Sci. USA,* 83, 8447–8451 (1986).

Jefferson, R., et al., "GUS Fusions: β–Glucuronidase as a Sensitive and Versatile Gene Fusion Marker in Higher Plants," *EMBO J.,* 6, 3901–3907 (1987).

Jefferson, R., "Assaying chimeric genes in plants: the GUS gene fusion system," *Plant Mol. Biol. Rep.,* 5, 387–405 (1987).

Jones, H., et al., "Recent Advances in Plant Electroporation," *Oxford Surveys of Plant Molecular and Cell Biol.,* 4, 347–357 (1987).

Jones, H., et al., "Transient Gene Expression in Electroporated Solanum Protoplasts," *Plant Mol. Biol.,* 13, 503–511 (1989).

Kaeppler, H. F., et al., "Silicon Carbide Fiber–Mediated DNA Delivery into Plant Cells," *Plant Cell Rep.,* 9, 415–418 (1990).

Kamo, K., et al., "Establishment and Characterization of Long–Term Embryonic Maize Callus and Cell Suspension Cultures," *Plant Sci.,* 45, 111–117 (1986).

Kamo, K, et al., "Regeneration of *Zea mays* L. from Embryogenic Callus," *Bot. Gaz.,* 146, 327–334 (1985).

Kao, K. N., et al., "Nutritional Requirements for Growth of *Vicia hajastana* Cells and Protoplasts at a Very Low Population Density in Liquid Media," *Planta,* 126, 105–110 (1978).

Kartha, K., et al., "Transient Expression of Chloramphenicol Acetyl Transferase (Cat) Gene in Barley Cell Cultures and Immature Embryos Through Microprojectile Bombardment," *Plant Cell Rep.,* 8, 429–432 (1989).

Kay, R., et al., "Duplication of CaMV 35S Promoter Sequences Creates a Strong Enhancer for Plant Genes," *Science,* 236, 1299–1302 (Jun. 5, 1987).

Kirihara, J., et al., "Differential Expression of a Gene for a Methionine–Rich Storage Protein in Maize," *Mol. Gen. Genet.,* 211, 477–484 (1988).

Kirihara, J., et al., "Isolation and Sequence of a Gene Encoding a Methionine–Rich 10–kD Zein Protein from Maize," *Gene,* 71, 359–370 (1988).

Klein, T., et al., "Transfer of Foreign Genes into Intact Maize Cells with High–Velocity Microprojectiles," *Proc. Nat. Acad. Sci. USA,* 85, 4305–4309 (1988).

Klein, T. M., et al., "Factor Influencing Gene Delivery into *Zea mays* Cells by High Velocity Microprojectiles," *Bio/Technol.,* 6, 559–563 (1988).

Klein, T. M., et al., "High–Velocity Microprojectiles for Delivering Nucleic Acids to Living Cells," *Nature,* 327, 70–73 (1987).

Klein, T., et al., "Genetic Transformation of Maize Cell by Particle Bombardment and the Influence of Methylation on Foreign Gene Expression," In: *Gene Manipulation in Plant Improvement II,* Gustafson, J. P., (ed.), Plenum Press, NY, pp. 265–266 (1990).

Klein, T., et al., "Genetic transformation of Maize Cells by Particle Bombardment," *Plant Physiol.,* 91, 440–444 (1989).

Klein, T., et al., "Regulation of Anthocyanin Biosynthetic Genes Introduced into Intact Maize Tissue by Microprojectiles," *Proc. Nat. Acad. Sci. USA,* 86, 6682–6685 (1989).

Kozak, M., "Compilation and Analysis of Sequence from the Translational Start Site in Eukaryotic mRNAs," *Nuc. Acids. Res.,* 12, 857–871 (1984).

Kozak, M., "Point Mutations Define a Sequence Flanking the AUG Initiator Codon that Modulates Translation by Eukaryotic Ribosomes," *Cell,* 44, 283–292 (1986).

Koziel, M. G., et al., "Field Performance of Elite Transgenic Maize Plants Expressing an Insecticidal Protein Derived from *Bacillus thuringenesis,*" *Bio/Technol.,* 11, 194–200 (1993).

Kreitlow, B., "Genetic Engineering 'Breakthrough' Disputed," Cedar Rapids Gazette (Apr. 20, 1990).

Kriz, A. L., et al., "Characterization of the Maize Globulin–2 Gene and Analysis of Two Null Alleles," *Biochemical Genetics,* 29, 241–254 (1991).

Kuhlemeier, C., et al., "Regulation of Gene Expression in Higher Plants," *Ann. Rev. Plant Physiol.,* 38, 234–239 (1987).

Landi, P., et al., "Genetic Analysis of Leaf ABA Concentration and Agronomic Traits in Maize Hybrids Grown Under Different Water Regimes," *Maydica,* 40, 179–186 (1995).

Langridge, et al., "Transformation of Cereals via Agrobacterium and the Pollen Pathway: A Critical Assessment," *The Plant J.,* 2, 613–638 (1992).

Laursen, C. M., et al., "Production of Fertile Transgenic Maize by Electorporation of Suspension Culture Cells," *Plant Mol. Biol.,* 24, 51–61 (1994).

Lazzeri, P., et al., "In Vitro Genetic Manipulation of Cereals and Grasses," *Ad. Cell Culture,* 6, 291–293 (1988).

Lee, J. S., et al., "Gene Transfer into Intact Cells of Tobacco by Electroporation," *Korean J. Gent.,* 11, 65–72 (1989).

Leemans, J., "Genetic Engineering for Fertility Control," Keystone Symposium on Crop Improvement via Biotechnology: An International Perspective, Abstract No. Y016 (Apr. 10–26, 1992).

Levitt, J., "Growth Regulators" In: *Introduction to Plant Physiology,* The C. V. Mosby Company, St. Louis, p. 241 (1969).

Li, X.–Q., et al., "GUS Expression in Rice Tissues Using Agrobacterium–Mediated Transformation," Program and Abstracts, Int. Soc. for Plant Mol. Biol., 3rd Int. Cong., Abstract No. 385 (Oct. 6–11, 1991).

Lindsey, K., et al., "Electroporation of Cells," *Physiologia Plantarum,* 79, 168–172 (1990).

Linsey, K., et al., "The Permeability of Electroporated Cells and Protoplasts of Sugar Beet," *Plant,* 172, 346–355 (1987).

Lindsey, K., et al., "Transient Gene Expression in Electroporated Protoplasts and Intact Cells of Sugar Beet," *Plant Mol. Biol.,* 10, 43–52 (1987).

Lindsey, K. et al., "Stable Transformation of Sugarbeet Protoplasts by Electroporation," *Plant Cell Rep.*, 8, 71–74 (1989).

Looker, D., "Dekalb Claims Success in Effort to Alter Genetic Makup of Corn," *Des Moines Register* (Apr. 19, 1990).

Lopes, M. A., et al., "Endosperm Origin, Development, and Function," *The Plant Cell*, 5, 1383–1399 (1993).

Lorz, H., et al., "Advances in Tissue Culture and Progress Towards Genetic Transformation of Cereals," *Plant Breeding*, 100, 1–25 (1988).

Lu, C., et al., "Somatic Embryogenesis in *Zea mays* L.," *Theor. Appl. Genet.*, 62, 109–112 (1982).

Lu, C., et al., "Improved Efficiency of Somatic Embryogenesis and Plant Regeneration on Tissue Cultures of Maize (*Zea mays* L.)," *Theor. Appl. Genet.*, 66, 285–289 (1983).

Ludwig, S., et al., "A Regulatory Gene as a Novel Visible Marker for Maize Transformation," *Science*, 247, 449–450 (1990).

Ludwig, S., et al., "High Frequency Callus Formation from Maize Protoplasts," *Theor. Appl. Genet.*, 71, 344–350 (1985).

Ludwig, S., et al., "Lc, a Member of the Maize R Gene Family Responsible for Tissue–Specific Anthocyanin Production, Encodes a Protein Similar to Transcriptional Activators and Contains the myc–Homology Region," *Proc. Nat. Acad. Sci. USA*, 86, 7092–7096 (1989).

Ludwig, S., et al., "Maize R Gene Family: Tissue–Specific Helix–Loop–Helix Proteins," *Cell*, 62, 849–851 (1990).

Lutcke, H., et al., "Selection of AUG Initiation Codons Differs in Plants and Animals," *EMBO J.*, 6, 43–48 (1987).

Maas, C., et al., "A Highly Optimized Monocot Expression Cassett: Application for Barley Transformation and Barley Virus Research," Program and Abstracts, Int. Soc. Plant Mol. Biol., Abstract No. 386 (Oct. 6–11, 1991).

Maddock, S. E., et al., "Expression in Maize Plants of Wheat Germ Agglutinin, a Novel Source of Insect Resistance," Program and Abstracts, Int. Soc. Plant Mol. Biol., 3rd Int. Cong., Abstract No. 372 (Oct. 6–11, 1991).

Masumura, T., et al., "cDNA Cloning of an mRNA Encoding a Sulfur–Rich 10 kDa Prolamin Polypeptide in Rice Seeds," *Plant Mol. Biol.*, 12, 123–130 (1989).

McCabe et al., "Stable Transformation of Soybean (*Glycine max*) by Particle Acceleration," *Bio/Technol.*, 6, 923–926 (1988).

McDaniel, C., et al., "Cell–Lineage Patterns in the Shoot Apical Meristem of the Germinating Maize Embryo," *Planta*, 175, 13–22 (1988).

Meadows, M., "Characterization of Cells and Protoplasts of the B73 Maize Cell Line," *Plant Sci. Lett.*, 28, 337–348 (1982/83).

Mendel, R., et al., "Delivery of Foreign Genes to Intact Barley Cell by High–Velocity Microprojectiles," *Theor. Appl. Genet.*, 78, 31–34 (1989).

Messing, J., "Corn Storage Protein: A Molecular Genetic Model," Division of Energy BioSciences—Summaries of FY 1990 Activities, p. 70, Abstract No. 135 (1990).

Milborrow, B. V., "Abscisic Acid and Other Hormones," In: *The Physiology and Biochemistry of Drought Resistance in Plants,* Paleg, L. G., et al., (eds.), Academic Press, New York, pp. 347–388 (1981).

Moffat, A. S., "Corn Transformed," *Science*, 249, 630 (Aug. 10, 1990).

Morikawa, et al., "Gene Transfer into Intact Plant Cells by Electroporation Through Cell Walls and Membranes," *Gene*, 41, 121 (1986).

Morocz, S. et al., "An Improved System to Obtain Fertile Regenerants via Maize Protoplasts Isolated From a Highly Embryonic Suspension Culture," *Theor. Appl. Genet.*, 80, 721–726 (1990).

Morocz, S., et al., "Two Approaches to Rendering *Zea mays* L. Applicable to Tissue Culture Manipulations," Abstracts, VIIth Int. Cong. on Plant Tissue and Cell Culture, Amsterdam A1–102, Abstract No. 209, p. 190 (1990).

Murakami, T., et al., "The Bialaphos Biosynthetic Genes of *Streptomyces hygroscopicus:* Molecular Cloning and Characterization of the Gene Cluster," *Mol. Gen. Genet.*, 205, 42–50 (1986).

Murashige, T., et al., A Revised Medium for Rapid Growth and Bio Assays with Tobacco Tissue Cultures, *Physiol. Plant.*, 15, 473–497 (1962).

Murphy, H. L., "New Dekalb–Pfizer Seed Chief to Harvest R & D Breakthroughs," *Crain's Business Weekly,* pp. 38–39 (1990).

Murray, E. E., et al., "Condon usage in plant genes," *Nuc. Acids Res.*, 17, 477–498 (1989).

Murray, L. E., et al., "Transgenic Corn Plants Expressing MDMV Strain B Coat Protein are Resistant to Mixed Infections of Maize Dwarf Mosaic Virus and Maize Chlorotic Mottle Virus," *Bio/Technol.*, 11, 1559–1564 (1993).

Nelson, R. S., "Virus Tolerance, Plant Growth, and Field Performance of Transgenic Tomato Plants Expressing Coat Protein from Tobacco Mosaic Virus," et al., *Bio/Technol.*, 6, 403–409 (1988).

Nelson, T., "New Horses for Monocot Gene Jockeys," *The Plant Cell,* 2, 589 (1990).

Neuffer, "Growing Maize for Genetic Purposes," Maize for Biological Research, Plant Mol. Biol. Assoc., (1988).

Niyogi, K. K., et al., "Suppressors of trp1 Fluorescence Identify a New Arabidopsis Gene, TRP4, Encoding the Anthranilate Synthase beta Gene," *The Plant Cell,* 5, 1011–1027 (1993).

Niyogi, K. K., et al., "Two Anthranilate Synthase Genes in Arabidopsis: Defense–Related Regulation of the Tryptophan Pathway," *The Plant Cell,* 4, 721–733 (1992).

Odell, J,. et al., "Identification of DNA Sequences Required for Activity of the Cauliflower Mosaic Virus 35S Promoter," *Nature,* 313, 810–811 (1985).

Office Action dated May 30, 1989, Goldman et al., USSN 06/880,271, filed Jun. 30, 1986.

Office Action dated Mar. 8, 1990, Goldman, USSN 06/880, 271, filed Jun. 30, 1986.

Ohta, Y., "High–Efficiency Genetic Transformation of Maize by a Mixture of Pollen and Exogenous DNA," *Proc. Nat. Acad. Sci. USA*. 83, 715–719 (1986).

Okta, Y., et al., "Gene Manifestation of Exogenous DNA Applied to Self–Propagating Stigma (Gene Action Revealed in the $M_1$ and $M_2$ Generations from Self–Pollination Applying Exogenous DNA)," *Jap. J. Breed.*, 30, 184–185 (1980).

Omirullen, S., et al., "Activity of a Chimeric Promoter with the Doubled CaMV 35S Enhancer in Protoplast–Derived Cells and Transgenic Plants in Maize," *Plant Mol. Biol.*, 21, 415–428 (1993).

Ozias–Akins, P., et al., "In vitro regeneration and genetic manipulation of grasses," *Physiol. Plant.*, 73, 565–569 (1988).

Ozias–Akins, P., et al., "Progress and Limitations in the Culture of Cereal Protoplasts," *Trends in Biotechnol.*, 2, 119–123 (1984).

Park, S. H., et al., "Selection of Maize Transformants form Shoot Apex Cultures Cocultivated with Agrobacterium Containing the Bar Gene," *In Vitro Cell. Develop. Biol.*, 29A, p. 85A, Abstract No. P–1102 (1993).

Parker, W. B., et al., "Selection and Characterization of Sethoxydim–Tolerant Maize Tissue Cultures," *Plant Physiol.*, 92, 1220–1225 (1990).

Pederson, K., et al., "Sequence Analysis and Characterization of a Maize Gene Encoding a High–Sulfur Zein Protein of $M_r$ 15,000," *J. Biol. Chem.*, 261, 6279–6284 (1986).

Perl, A., et al., "Bacterial Dihydrodipicolinate Synthase and Desensitized Aspartate Kinase: Two Novel Selectable Markers for Plant Transformation," *Bio/Technol.*, 11, 715–718 (1993).

Perlack, F. J., et al., "Modification of the Coding Sequence Enhances Plant Expression of Insect Control Protein Genes," *Proc. Nat. Acad. Sci. USA*, 88, 3324–3328 (1991).

Phillips, R. L., "Elevated Protein–Bound Methionine in Seeds of a Maize Line Resistant to Lysine Plus Threonine," *Cereal Chem.*, 62, 213–218 (1985).

Phillips, R. L., et al., "Cell/Tissue Culture and In Vitro Manipulation," In: *Corn and Corn Improvement*, 3rd edition, Sprague, G. F., et al., (eds.), Agronomy Soc. Amer., pp. 345–387 (1988).

Pioneer HiBred International, Inc., *Application Under 7 CFR 340*, Release of Genetically Engineered Corn Plants, Permit No. 92–174–02, No CBI, p. 8 (Nov. 3, 1992). Pioneer HiBred International, Inc., *Application Under 7 CFR 340*, Release of Genetically Engineered Corn Plants, Permit No. 92–330–01, CBI–Deleted, p. 13 (Apr. 13, 1993). Phillips, R. L., et al., "Elevated Protein–Bound Methionine in Seeds of a Maize Line Resistant to Lysine Plus Threonine," *Cereal Chem.*, 62, 213–218 (1985). Pioneer's Application for Release in the *Environment Under 7 CFR 340*, Corn Plants Genetically Engineered to Express Wheat Germ Agglutinin (WGA) Genes, in Order to Confer Resistance to the European Corn Borer (*Ostrinia nubilalis*) and Tolerance to Glufosinate Herbicides, 92–022–03, No CBI Copy, p. 11 (May 4, 1992).

Poehlman, J. "Breeding Corn (Maize)," In: *Breeding Field Crops*, 3rd edition, AVI Publishing Co., Westport CN, pp. 452, 469–471, 477–481 (1986).

Potrykus, I., et al., "Callus Formation from Cell Culture Protoplasts of Corn (*Zea mays* L.)," *Theor. Appl. Genet.*, 54, 209–214 (1979).

Potrykus, I., "Gene Transfer to Cereals: An Assessment," *Bio/Technol.*, 8, 535–542 (Jun. 1990).

Potrykus, I., "Gene Transfer to Cereals: An Assessment," *Trends Biotechonol.*, 7, 269–273 (Oct. 1989).

Potrykus, I., "Gene Transfer to Plants: Assessment and Perspectives," *Physiol. Plant.*, 79, 125–134 (1990).

Potrykus, I., et al., "Callus formation from stem protoplasts of corn (*Zea mays* L.)" *Mol. Gen. Genet.*, 156, 347–350 (1977).

Potter, et al., "Enhancer–Dependent Expression of Human κ Immunoglobulin Genes Introduced into Mouse Pre–B Lymphocytes by Electoporation," *Proc. Nat. Acad. Sci. USA*, 81, 7161 (1984).

Prioli, L. M., et al., "Plant Regeneration and Recovery of Fertile Plants from Protoplasts of Maize (*Zea mays* L.)," *Bio/Technol.* 7, 589–594 (Jun. 1989).

Puite, K. J., et al., "Electrofusion, a Simple and Reproducible Technique in Somatic Hybridization of *Nicotiana plumbaginifolia* mutants," *Plant Cell Rep.*, 4, 274–276 (1985).

Rasmusen, J. L., et al., "Biolistic Transformation of Tobacco and Maize Suspension Cells Using Bacterial Cells as Microprojectiles," *Plant Cell Rep.*, 13, 212–217 (1994).

Rhodes, C. A., et al., "Genetically Transformed Maize Plants from protoplasts," *Science*, 240, 204–207 (Apr. 8, 1988).

Rhodes, C. A., et al., "Plant Regeneration from Protoplasts Isolated from Embryogenic Maize Cell Cultures," *Bio/Technol.*, 6, 56–60 (Jan. 1988).

Rhodes, C. A., "Corn: From Protoplasts to Fertile Plants," *Bio/Technol.*, 7, 548 (Jun. 1989).

Richaud, F., et al., "Chromosomal Location and Nucleotide Sequence of the *Escherichia coli* dapA Gene," *Biol. Abstracts*, 82, p. AB–391, Abstract No. 3396 (1986).

Richaud, F., et al., "Chromosomal Location and Nucleotide Sequence of the *Escherichia coli* dapA Gene," *J. Bacteriol.*, 166, 297–300 (1986).

Robbins–Roth et al., "They Make it Happen in Biotech," *Bioworld*, pp. 30–36 (Nov./Dec. 1990).

Robertson, D. S., "Loss of Mu Mutator Activity when Active Mu Systems are Transferred to Inbred Lines," *Maize Genetics Coop. Newsletter*, 60, 10 (1986).

Ross, M.C., et al., "Transient and Stable Transgenic Cells and Calli of Tobacco and Maize Following Microprojectile Bombardment," *J. Cell. Biochem.*, 13D, p. 268, Abstract No. M149 (1989).

Sahi, S. V., et al., "Metabolites in Maize Which Affect Virulence Induction in *Agrobacterium tumefaciens*," *Plant Physiol.*, Supplement, p. 86, Abstract No. 514, (1989).

Sanford, J. C., "Biolistic Plant Transformation," *Physiol. Plant.*, 79, 206–209 (1990).

Sanford, J. C., "The Biolistic Process," *Trends Biotechnol.*, 6, 299–302 (1988).

Sanford, J.C., et al., "Attempted Pollen–Mediated Plant Transformation Employing Genomic Donor DNA," *Theor. Appl. Genet.*, 69, 571–574 (1985).

Sanford, J. C., et al., "Delivery of Substances into Cells and Tissues Using a Particle Bombardment Process," *Particulate Sci. Technol.*, 5, 27–37 (1987).

Sass, "Morphology: Development of the Caryopsis" In: *Corn and Corn Improvement*, 2nd edition, Sprauge, G. F., (ed.), American Soc. Agronomy, pp. 89, 98 (1977).

Schmidt, A., et al., "Media and environmental effects of phenolics production from tobacco cell cultures," *Chem. Abstracts*, 110, p. 514, Abstract No. 230156z (1989).

Shen. W,–H., et al., "Excision of a Transposible Element form a Viral Vector Introduced into Maize Plants by Agroinfection," *The Plant J.*, 2, 35–42 (1992).

Shen, W.–H., et al., "Amplification and expression of the β–glucuronidase gene in maize plants by vectors based on maize streak virus," *The Plant Journal*, 5, 227–236 (1994).

Shigekawa, K., et al., "Electroporation of Eukaryotes and Prokaryotes: A General Approach to the Intoduction of Macromolecules into Cells," *BioTechniques*, 6, 742–751 (1988).

Shillito, R. D., et al., "High Efficiency Direct Gene Transfer to Plants," *Bio/Technol.*, 3, 1099 (1985).

Shillito, R. D., et al., "Regeneration of Fertile Plants From Protoplasts of Elite Inbred Maize," *Bio/Technol.*, 7, 581–587 (Jun. 1989).

Shimamoto, K., et al., "Fertile Transgenic Rice Plants Regenerated from Transformed Protoplasts," *Nature*, 338, 274–278 (1989).

Shotwell, M. A., et al., "The Biochemistry of Plants—A Comprehensive Treatise," In: *The Biochemistry of Plants*, vol. 15, Marcus, A., (ed.), Academic Press, Inc., San Diego, pp. 297–345 (1989).

Smith, R., et al., "Shoot apex explant for transformation," *Plant Physiol.*, 86, p. 108, Abstract No. 646 (1988).

Soberon, X., et al., "Construction and Characterization of New Cloning Vehicles, IV. Deletion Derivatives of pBR322 and pBR325," *Gene*, 9, 287–305 (1980).

Songstad, D. D., et al., "Transient Expression of GUS and Anthocyanin Constructs in Intact Maize Immature Embryos Following Electroporation," *Plant Cell Tissue and Organ Culture*, 33, 195–201 (1993).

Spencer, T. M. et al., "Fertile Transgenic Maize," Abstracts, 7th Annual Meeting, Mid Atlantic Plant Mol. Biol. Soc., p. 30 (1990).

Spencer et al., "Bialaphos Selection of Stable Transformations from Maize Cell Culture," *Theor. Appl. Genet.*, 79, 625–631 (May 1990).

Spencer, T. M., et al., "Segregation of Transgenes in Maize," *Plant Mol. Biol.*, 18, 201–210 (1992).

Spencer, T.M., et al., "Selection of Stable Transformants from Maize Suspension Cultures using the Herbicide Bialaphos," Poster presentation, FASEB Plant Gene Expression Conference, Copper Mountain, Colorado (Aug. 8, 1989).

Sprauge et al., "Corn Breeding," In: *Corn and Corn Improvement*, Sprauge, G. F., (ed.), American Society of Agronomy, Inc, Madison, Wi, pp. 305, 320–323 (1977).

Steimel, D., "Corn Breeders Stalk Perfect Hybrid," *Rockford Register Star*, (Aug. 6, 1990).

Steimel, D., "New Gun Will Custom–Design Corn: Breeding Technique Expected by End of '90's Will Let Crop Grow Without Pesticides or Much Water," (Apr. 1990).

Sugiyama, M., et al., "Use of the Tyrosinase Gene from Streptomyces to Probe Promoter Sequences for *Escherichia coli*," *Plasmid*, 23, 237–241 (1990).

Suttie, J., et al., "Use of Different Selection Agents to Produce Maize Transformants of an Elite Geneotype Using Microprojectile Bombardment," Program and Abstracts, Int. Soc. Plant Mol. Biol., 3rd Int. Cong., Abstract No. 426 (Oct. 6–11, 1991).

Tarczynski, M. C., et al., "Expression of a Bacterial mtlD Gene in Transgenic Tobacco Leads to Production and Accumulation of Mannitol," *Proc. Nat. Acad. Sci. USA*, 89, 2600–2604 (1992).

Tarczynski, M. C., et al., "Stress Protection of Transgenic Tobacco by Production of the Osmolyte Mannitol," *Science*, 259, 508–510 (1993).

Thompson, C., et al., "Characterization of the Herbicide–Resistance Gene bar from *Streptomyces hygroscopicus*," *EMBO J.*, 6, 2519–2523 (1987).

Tomes, D. "Status of Corn Transformation," 26th Annual Corn Breeders School, Meeting Proceedings, U. Illinois, pp. 7–8 (Feb. 26–27, 1990).

Tomes, D. T., et al., "Transgenic Tobacco Plants and their Progeny Derived by Microprojectile Bombardment of Tobacco Leaves," *Plant Mol. Biol.*, 14, 261–268 (Feb. 1990).

Twell, D., et al., "Transient Expression of Chimeric Genes Delivered into Pollen by Microprojectile Bombardment," *Plant Physiol.*, 91, 1271–1274 (1989).

Ulian, E., et al., "Transformation of Plants via the Shoot Apex," *In Vitro Cell. Dev. Biol.*, 9, 951–954 (1988).

Usami, S., et al., "Absence in Monocotyledonous Plants of the Diffusible Plant Factors including T–DNA Circularization and vir Gene Expression in Agrobacterium," *Mol. Gen. Genet.*, 209, 221–226 (1987).

Vain, P., et al., "Osmotic Pretreament Enhances Particle Bombardment–Mediated Transient and Stable Transformation of Maize," *Plant Cell Rep.*, 12, 84–88 (1993).

Vasil, I. K., "Transgenic Cereals Becoming a Reality," *Bio/Technol.*, 8, 797 (Sep. 1990).

Vasil, I. K., et al., "Culture of Protoplasts Isolated from Embryogenic Cell Suspension Cultures of Sugarcane and Maize," *IAPTC Abstracts*, p. 443 (1986).

Vasil, V., et al., "Isolation and Maintenance of Embryogenic Cell Suspension Cultures of Gramineae," In: *Cell Culture and Somatic Cell Genetics of Plants*, vol I, Academic Press, pp. 152–158 (1984).

Vasil, V., et al., "Plant Regeneration from Friable Embryonic Callus and Cell Suspension Cultures of *Zea mays* L.," *J. Plant Physiol.*, 124, 399–408 (1986).

Walbot, V., et al., "Molecular genetics of corn," In: *Corn and Corn Improvement*, 3rd edition, Sprauge, G. F., et al., (eds.), American Soc. Agronomy, Madison, WI, pp. 389–430 (1988).

Waldron, C., et al., "Resistance to Hygromycin B," *Plant Mol. Biol.*, 5, 103–108 (1985).

Walters, D. A., et al., "Transformation and Inheritance of Hygromycin Phosphotransferase Gene in Maize Plants," *Plant Molecular Biol.*, 18, 189–200 (1992).

Wan, Y., et al., "Generation of Large Numbers of Independently Transformed Fertile Barley Plants," *Plant Physiol.*, 104, 37–48 (1994).

Wan, Y., et al., "Maize Transformation and Regeneration of Transgenic Plants by Microprojectile Bombardment of Type I Callus," Abstracts, 35th Annual Maize Genetics Conference, p. 5 (Mar. 18–21, 1993).

Wang, Y., et al., "Characterization of cis–Acting Elements Regulating Transcription from the Promoter of a Constitutively Active Rice Actin Gene," *Mol. Cell. Biol.*, 12, 3399–3406 (1992).

Wang, Y., et al., "Transient Expression of Foreign Genes in Rice, Wheat and Soybean Cells Following Particle Bombardment," *Plant Mol. Biol.*, 11, 433–439 (1988).

Weising, K., et al., "Foreign Genes in Plants: Transfer, Structure, Expression and Applications," *Ann. Rev. Genet.*, 22, 421–478 (1988).

White, J., et al., "A Cassett Containing the bar Gene of *Streptomyces hygroscopicus*: a Selectable Marker for Plant Transformation," *Nuc. Acid. Res.*, 18, 1062 (1989).

Whiteley, H.R., et al., The Molecular Biology of Parasporal Crystal Body Formation in *Bacillus thuringiensis*, *Ann. Rev. Microbiol.*, 40, 549–576 (1986).

Wong, E.Y., et al., "*Arabidopsis thaliana* Small Subunit Leader and Transit Peptide Enhance the Expression of *Bacillus thuringiensis* Proteins in Transgenic Plants," *Plant Mol. Biol.*, 20, 81–93 (1992).

Xue, Q., et al., "Genotypic Variation in Osmotic Adjustment Among Closely Related Wheat Lines," Agronomy Abstracts, p. 78 (1995).

Yang, H., et al., "Production of Kanamycin Resistant Rice Tissues Following DNA Uptake into Protoplasts," *Plant Cell Rep.*, 7, 421 (1988).

Yanisch–Perron, C., et al., "Improved M13 Phage Vectors and Host Strains: Nucleotide Sequences of M13mp18 and pUC19 Vectors," *Gene*, 33, 103–119 (1985).

Yugari, Y., et al., "Coordinated End–Product Inhibition in Lysine Synthesis in *Escherichia coli*," *Biochem. Biophys. Acta*, 62, 612–614 (1962).

Bernasconi, P., et al., "Functional Expression of *Arabidopsis thaliana* Anthranilate Synthase Subunit I in *Escherichia coli*", *Plant Physiol.*, 106, 353–358 (1994).

International Search Report, PCT/US 97/00983, mailed Jun. 12, 1997.

International Search Report, PCT/US 97/00978, mailed Jul. 22, 1997.

Andrews, D.L., et al., "Characterization of the Lipid Acyl Hydrolase Activity of the Major Potato (*Solanum tuberosum*) Tuber Protein, Patatin, by Cloning and Abundant Expression in a Baculovirus Vector", *Biochem. J.*, 252, 199–206 (1988).

Atanassova, R., et al., "A 126 bp Fragment of Plant Histone Gene Promoter Confers Preferential Expression in Meristems of Transgenic Arabidopsis", *The Plant J.*, 2, 291–300 (1992).

Bohlmann, J., et al., "Purification and cDNA Cloning of Anthranilate Synthase from *Ruta graveolens*: Modes of Expression and Properties of Native and Recombinant Enzymes", *The Plant J.*, 7, 491–501 (1995).

Botterman, J., et al., "Engineering Herbicide Resistance in Plants", *Trends in Genet.*, 4, 219–222 (Aug. 1988).

Brignon, P., et al., "Nuclease Sensitivity and Functional Analysis of a Maize Histone H3 Gene Promoter", *Plant Mol. Biol.*, 22, 1007–1015 (1993).

Datta, S.K., et al., "Genetically Engineered Fertile Indica–Rice Recovered from Protoplasts", *Bio/Technology*, 8, 736–740 (Aug. 1990).

Holmstrom, K.–O., et al., "Production of the *Escherichia coli* Betaine/Aldehyde Dehydrogenase, an Enzyme Required for the Synthesis of the Osmoprotectant Glycine Betaine, in Transgenic Plants", *The Plant J.*, 6, 749–758 (1994).

Hooykaas–Van Slogteren, G.M.S., et al., "Expression of Ti Plasmid Genes in Monocotyledonous Plants Infected with *Agrobacterium tumefaciens*", *Nature*, 311, 763–764 (Oct. 25, 1984).

Jaynes, J.M., et al., "Plant Protein Improvement by Genetic Engineering: Use of Synthetic Genes", *Trends Biotech.*, 4, 314–320 (Dec. 1986).

Kavi Kishor, P.B., et al., "Overexpression of Delta$^1$–Pyrroline–5–Carboxylate Sythetase Increases Proline Production and Confers Osmotolerance in Transgenic Plants", *Plant Physiol.*, 108, 1387–1394, (1995).

Li, J., et al., "The *Arabidopsis thaliana* trp5 Mutant Has a Feedback–Resistant Anthranilate Synthase and Elevated Soluble Tryptophan", *Plant Physiol.*, 110, 51–59, (1996).

Mariani, C., et al., "Engineered Male Sterility in Plants", *Symposia of the Society for Experimental Biology*, No. XLV, Proceedings of a Meeting Held at the University of Glasgow, Scotland, pp. 271–279 (1991).

McCue, K.F., et al., "Drought and Salt Tolerance: Towards Understanding and Application", *TIBTECH*, 8, 358–362 (Dec. 1990).

Ranch, J.P., et al., "Expression of 5–Methyltryptophan Resistance in Plants Regenerated from Resistant Cell Lines of *Datura innoxia*", *Plant Physiol.*, 71, 136–140 (1983).

Rathinasabapathi, B., et al., "Metabolic Engineering of Glycine Betaine Synthesis: Plant Betaine Aldehyde Dehydrogenases Lacking Typical Transit Peptides are Targeted to Tobacco Chloroplasts Where They Confer Betaine Aldehyde Resistance", *Planta*, 193, 155–162 (1994).

Saneoka, H., et al., "Salt Tolerance of Glycinebetaine–Deficient and–Containing Maize Lines", *Plant Physiol.*, 107, 631–638 (1995).

Shen, B., et al., "Partial Sequencing and Mapping of Clones from Two Maize cDNA Libraries", *EMBL Sequence Data Library*, Heidelberg, Germany (Oct. 1, 1994).

Shen, B., et al., "Partial Sequencing and Mapping of Clones from Two Maize cDNA Libraries", *Plant Mol. Biol.*, 26, 1085–1101 (1994).

Vasil, V., et al., "Regeneration of Plants from Embryogenic Suspension Culture Protoplasts of Wheat (*Triticum aestivum* L.)", *Bio/Technology*, 8, 429–434 (May 1990).

Xu, D., et al., "Expression of a Late Embryogenesis Abundant Protein Gene, HVA1, from Barley Confers Tolerance to Water Deficit and Salt Stress in Transgenic Rice", *Plant Physiol.*, 110, 249–257 (1996).

Armstrong, C.L., et al., "Genetic and Cytogenetic Variation in Plants Regenerated from Organogenic and Friable, Embryogenic Tissue Cultures in Maize", *Crop Science*, 28, 363–369 (1988).

Beauregard, M., et al., "Design, Expression, and Initial Characterization of MB1, a De Novo Protein Enriched in Essential Amino Acids", *Bio/Technology*, 13, 974–981 (Sep. 1995).

Casas, A.M., et al., "Transgenic Sorghum Plants via Microprojectile Bombardment", *Proc. Natl. Acad. Sci. USA*, 90, 11212–11216 (Dec. 1993).

Dure III, L., et al., "Common Amino Acid Sequence Domains Among the LEA Proteins of Higher Plants", *Plant Molecular Biology*, 12, 475–486 (1989).

Falco, S.C., et al., "Transgenic Canola and Soybean Seeds with Increased Lysine", *Bio/Technology*, 13, 577–582 (Jun. 1995).

Hong, B., et al., "Cloning and Characterization of cDNA Encoding a mRNA Rapidly–Induced by ABA in Barley Aleurone Layers", *Plant Molecular Biology*, 11, 495–506 (1988).

Lemaux, P.G., et al., "Selection of Stable Transformants from Maize Suspension Cultures Using the Herbicide Bialaphos", *J. Cell. Biochem.*, 14e, Abstract R230, 304 (Mar. 31, 1990).

Mundy, J., et al., "Abscisic Acid and Water–Stress Induce the Expression of a Novel Rice Gene", *The EMBO Journal*, 7, 2279–2286 (1988).

Piatkowski, D., et al., "Characterization of Five Abscisic Acid–Responsive cDNA Clones Isolated from the Desiccation–Tolerant Plant *Craterostigma plantagineum* and Their Relationship to Other Water–Stress Genes", *Plant Physiology*, 94, 1682–1688 (1990).

Somers, D.A., et al., "Fertile, Transgenic Oat Plants", *Bio/Technology*, 10, 1589–1594 (Dec. 1992).

Yamaguchi–Shinozaki, K., et al., "Molecular Cloning and Characterization of 9 cDNAs for Genes that are Responsive to Desiccation in *Arabidopsis thaliana*: Sequence Analysis of One cDNA Clone that Encodes a Putative Transmembrane Channel Protein", *Plant Cell Physiol.*, 33, 217–224 (1992).

Flavell, R., et al., "Prospects for Transforming Monocot Crop Plants", *Nature*, 307, 108–109 (Jan. 12, 1984).

Goodman, R.M., et al., "Gene Transfer in Crop Improvement", *Science,* 236, 48–54 (Apr. 3, 1987).
Jahne, A., et al., "Genetic Engineering of Cereal Crop Plants: A Review", *Euphytica,* 85, 35–44 (1995).
Paszkowski, J., et al., "Direct Gene Transfer to Plants", *The EMBO Journal,* 3, 2717–2722 (1984).
Poehlman, J.M., "Backcross Breeding", In: *Breeding Field Crops, 3rd Edition,* AVI Publishing Company, Inc., Westport, CT, 203–206 (1988).
Potrykus, I., et al., "Direct Gene Transfer to Cells of a Graminaceous Monocot", *Mol. Gen. Genet.,* 199, 183–188 (1985).
Pioneer Hi–Bred International, Inc., Application Under 7 C.F.R. 340, Release of Genetically Engineered Corn Plants, Permit No. 92–212–01, CBI–Deleted, p. 11 (Nov. 16, 1992).
Abe, K., et al., "Molecular Cloning of a Cysteine Proteinase Inhibitor of Rice (Oryzacystatin)", *The Journal of Biological Chemistry,* 262, 16793–16797 (Dec. 15, 1987).
Al–Feel, W., et al., "Cloning of the Yeast FAS3 Gene and Primary Structure of Yeast Acetyl–CoA Carboxylase", *Proc. Natl. Acad. Sci. USA,* 89, 4543–4538 (May 1992).
Anderson, J.M., et al., "The Encoded Primary Sequence of a Rice Seed ADP–glucose Pyrophosphorylase Subunit and Its Homology to the Bacterial Enzyme", *The Journal of Biological Chemistry,* 264, 12238–12242 (Jul. 25, 1989).
Arondel, V., et al. "Map–Based Cloning of a Gene Controlling Omega–3 Fatty Acid Desaturation in Arabidopsis", *Science,* 258, 1353–1355 (Nov. 20, 1992).
Bagga, S., et al., "Accumulation of 15–kilodalton Zein in Novel Protein Bodies in Transgenic Tobacco", *Plant Physiol.,* 107, 13–23 (1995).
Bartley, G.E., et al., "Molecular Cloning and Expression in Photosynthetic Bacteria of a Soybean cDNA Coding for Phytoene Desaturase, and Enzyme of the Carotenoid Biosynthesis Pathway", *Proc. Natl. Acad. Sci. USA,* 88, 6532–6536 (Aug. 1991).
Bol, J.F., et al., "Plant Pathogenesis–Related Proteins Induced by Virus Infection", *Annu. Rev. Phytopathol.,* 28, 113–138 (1990).
Bowler, C., et al., "Superoxide Dismutase and Stress Tolerance", *Annu. Rev. Plant Physiol. Plant Mol. Biol.,* 43, 83–116 (1992).
Castillo, A.M., et al., "Rapid Production of Fertile Transgenic Plants of Rye (*Secale cereale* L.)", *Bio/Technology,* 12, 1366–1371 (Dec. 1994).
Christou, P., et al., "Production of Transgenic Rice (*Oryza sativa* L.) Plants from Agronomically Important Indica and Japonica Varieties via Electric Discharge Particle Acceleration of Exogenous DNA into Immature Zygotic Embryos", *Bio/technology,* 9, 957–962 (Oct. 1991).
Chui, C.–F., et al., "A New Methionine–Rich Seed Storage Protein from Maize", *Plant Physiol.,* 107, 291 (1995).
Depicker, A.G., et al., "A Negative Selection Scheme for Tobacco Protoplast–Derived Cells Expressing the T–DNA Gene 2", *Plant Cell Reports,* 7, 63–66 (1988).
Domoney, C., et al., "Cloning and Characterization of Complementary DNA for Convicilin, a Major Seed Storage Protein in *Pisum sativum* L.", *Planta,* 159, 446–453 (1983).
Döge–Laser, W., et al., "The Metabolites of the Herbicide L–Phosphinothricin (Glufosinate)", *Plant Physiol.,* 105, 159–166 (1994).
Dunn, G.M., et al., "Inheritance of Cyclic Hydroxamates in *Zea mays* L.", *Can. J. Plant Sci.,* 61, 583–593 (Jul. 1981).

Fisher, D.K., et al., "Starch Branching Enzyme II from Maize Endosperm", *Plant Physiol.,* 102, 1045–1046 (1993).
Frame, B.R., et al., "Production of Fertile Transgenic Maize Plants by Silicon Carbide Whisker–Mediated Transformation", *The Plant Journal,* 6, 941–948 (1994).
Gepts, P., et al., "Enhanced Available Methionine Concentration Associated with Higher Phaseolin Levels in Common Bean Seeds", *Theor. Appl. Genet.,* 69, 47–53 (1984).
Guerrero, F.D., et al., "Turgor–Responsive Gene Transcription and RNA Levels Increase Rapidly When Pea Shots are Wilted. Sequence and Expression of Three Inducible Genes", *Plant Mol. Biol.,* 15, 11–26 (1990).
Gupta, A.S., et al., "Increased Resistance to Oxidative Stress in Transgenic Plants that Overexpress Chloroplastic Cu/Zn Superoxide Dismutase", *Proc. Natl. Acad. Sci. USA,* 90, 1629–1633 (Feb. 1993).
Häger, K.–P., et al., "Evolution of Seed Storage Protein Genes: Legumin Genes of *Ginkgo biloba*", *Journal of Molecular Evolution,* 41, 457–466 (1995).
Häger, K.–P., et al., "Seed Storage Proteins of Cupressaceae Are Homologous to Legumins from Angiosperms: Molecular Characterization of cDNAs from Incense Cedar (*Calocedrus decurrens* [Torr.] Florin)", *Plant Science,* 116, 85–96 (May 1996).
Hartman, C.L., et al., "Herbicide Resistant Turfgrass (*Agrostis palustris* Huds.) by Biolistic Transformation", *Bio/Technology,* 12, 919–923 (Sep. 1994).
Hu, N.–T., et al., "Primary Structure of a Genomic Zein Sequence of Maize", *The EMBO Journal,* 1, 1337–1342 (1982).
Jähne, A., et al., "Regeneration of Transgenic, Microspore––Derived, Fertile Barley", *Theor. Appl. Genet.,* 89, 525–533 (1994).
Jaworski, J.G., et al., "A Cerulenin Insensitive Short Chain 3–Ketoacyl–Acyl Carrier Protein Synthase in *Spinacia oleracea* Leaves", *Plant Physiol.,* 90, 41–44 (1989).
Josefsson, L.G., et al., "Structure of a Gene Encoding the 1.7 S Storage Protein, Napin, from *Brassica napus*", *The Journal of Biological Chemistry,* 262, 12196–12201 (Sep. 5, 1987).
Kaasen, I., et al., Molecular Cloning and Physical Mapping of the otsBA Genes, Which Encode the Osmoregulatory Trehalose Pathway of *Escherichia coli:* .
Evidence that Transcription is Activated by KatF (AppR), *Journal of Bacteriology,* 174, 889–898 (Feb. 1992).
Kim, C.S., et al., "Improvement of Nutritional Value and Functional Properties of Soybean Glycinin by Protein Engineering", *Protein Engineering,* 3, 725–731 (1990).
Knight, M.R., et al., "Transgenic Plant Aequorin Reports the Effects of Touch and Cold–Shock and Elicitors on Cytoplasmic Calcium", *Nature,* 352, 524–526 (Aug. 8, 1991).
Kogami, H., et al., "Molecular and Physiological Evaluation of Transgenic Tobacco Plants Expressing a Maize Phosphoenolpyruvate Carboxylase Gene Under the Control of the Cauliflower Mosaic Virus 35S Promoter", *Biol. Abstr.,* 98, Abstract. No. 147991, p. AB–596 (1994).
Kohno–Murase, J., et al., "Improvement in the Quality of Seed Storage Protein by Transformation of *Brassica napus* with an Antisense Gene for Cruciferin", *Theor. Appl. Genet.,* 91, 627–631 (1995).
Kononowicz, H., et al., "Subdomains of the Octopine Synthase Upstream Activating Element Direct Cell–Specific Expression in Transgenic Tobacco Plants", *The Plant Cell,* 4, 17–27 (Jan. 1992).

Lamppa, G., et al., "Analysis of Two Linked Genes Coding for the Acyl Carrier Protein (ACP) from *Arabidopsis thaliana* (Columbia)", *Plant Molecular Biology*, 16, 469–474 (1991).

Larkins, B.A., et al., "Modification of Maize–Seed Protein Quality", *Am. J. Clin. Nutr.*, 58, 264S–269S (1993).

Malan, C., et al., "Correlation Between CuZn Superoxide Dismutase and Gluthathione Reductase, and Environmental and Xenobiotic Stress Tolerance in Maize Inbreds", *Plant Science*, 69, 157–166 (1990).

Marks, M.D., et al., "Nucleotide Sequence Analysis of Zein mRNAs from Maize Endosperm", *The Journal of Biological Chemistry*, 260, 16451–16459 (Dec. 25, 1985).

Matthews, B.F., et al., "Nutritional Improvement of the Aspartate Family of Amino Acids in Edible Crop Plants", *Amino Acids*, 4, 21–34 (1993).

Mehta, A., et al., "A Step Towards Developing Transgenic Plants With High Nutritional Quality", *Proc. Indian Natl. Sci. Acad.*, B60, 375–380 (1994).

Montoliu, L., et al., "A Tandem of α–Tubulin Genes Preferentially Expressed in Radicular Tissues from *Zea mays*", *Plant Molecular Biology*, 14, 1–15 (1989).

Mundy, J., et al., "Selective Expression of a Probable Amylase/Protease Inhibitor in Barley Aleurone Cells: Comparison to the Barley Amylase/Subtilisin Inhibitor", *Planta*, 169, 51–63 (1986).

Nishida, I., et al., "The Gene and the RNA for the Precursor to the Plastid–Located Glycerol–3–phosphate Acyltransferase of *Arabidopsis thaliana*", *Plant Molecular Biology*, 21, 267–277 (1993).

O'Reilly, D.R., et al., "A Baculovirus Blocks Insect Molting by Producing Ecdysteroid UDP–Glucosyl Transferase", *Science*, 245, 1110–1112 (Sep. 8, 1989).

Rice, J.A., et al., "Expression of Synthetic High Lysine Seed Storage Proteins can Significantly Increase the Accumulated Levels of Lysine in Mature Seeds of Transgenic Crop Plants", *Journal of Cellular Biochemistry*, 18 Part A, Abstract No. X1–329, p. 107 (1994).

Shorrosh, B.S., et al., "Molecular Cloning, Characterization, and Elicitation of Acetyl–CoA Carboxylase from Alfalfa", *Proc. Natl. Acad. Sci. USA*, 91, 4323–4327 (May 1994).

Shotwell, M.A., et al., "Analysis of Seed Storage Protein Genes of Oats", *The Journal of Biological Chemistry*, 265, 9652–9658 (Jun. 15, 1990).

Smith, I.K., et al., "Properties and Functions of Glutathione Reductase in Plants", *Physiol. Plant.*, 77, 449–456 (1989).

Stalker, D.M., et al., "Herbicide Resistance in Transgenic Plants Expressing a Bacterial Detoxification Gene", *Science*, 242, 419–422 (Oct. 21, 1988).

Stark, D.M., et al., "Regulation of the Amount of Starch in Plant Tissues by ADP Glucose Pyrophosphorylase", *Science*, 258, 287–291 (Oct. 9, 1992).

Stiefel, V., et al., "Expression of a Maize Cell Wall Hydroxyproline–Rich Glycoprotein Gene in Early Leaf and Root Vascular Differentiation", *The Plant Cell*, 2, 785–793 (Aug. 1990).

Stougaard, J., "Susbtrate–Dependent Negative Selection in Plants Using a Bacterial Cytosine Deaminase Gene", *The Plant Journal*, 3, 755–761 (1993).

Vernon, D.M., et al., "A Novel Methyl Transferase Induced by Osmotic Stress in the Facultative Halophyte *Mesembryanthemum crystallinum*", *The EMBO Journal*, 11, 2077–2085 (1992).

Viotti, A., et al., "Each Zein Gene Class Can Produce Polypeptides of Different Sizes", *The EMBO Journal*, 4, 1103–1110 (1985).

Weeks, J.T., et al., "Rapid Production of Multiple Independent Lines of Fertile Transgenic Wheat (*Triticum aestivum*)", *Plant Physiol.*, 102, 1077–1084 (1993).

Werr, W., et al., "Structure of the Sucrose Synthase Gene on Chromosome 9 of *Zea mays* L." *The EMBO Journal*, 4, 1373–1380 (1985).

Wolter, F.P., et al., "Chilling Sensitivity of *Arabidopsis thaliana* with Genetically Engineered Membrane Lipids", *The EMBO Journal*, 11, 4658–4692 (1992).

Xiang, C., et al., "The Anti–nptII Gene—A Potential Negative Selectable Marker for Plants", *Plant Physiol.*, 102, 287–293 (1993).

Yang, N.-S., et al., "Maize Sucrose Synthase–1 Promoter Directs Phloem Cell–Specific Expression of Gus Gene in Transgenic Tobacco Plants", *Proc. Natl. Acad. Sci. USA*, 87, 4144–4148 (Jun. 1990).

Yenofsky, R.L., et al., "Isolation and Characterization of a Soybean (*Glycine max*) Lipoxygenase–3 Gene", *Mol. Gen. Genet.*, 211, 215–222 (1988).

Van den Broeck, G., et al., "Targeting of a Foreign Protein to Chloroplasts by Fusion to the Transit Peptide from the Small Subunit of Ribulose 1,5–bisphosphate Carboxylase", *Nature*, 313, 358–363, (Jan. 31, 1985).

Bernasconi, P. et al., "Functional Expression of *Arabidopsis thaliana* Anthranilate Synthase Subunit I in *Escherichia coli*", *Plant Physiol.*,106, 353–358 (1994).

\* cited by examiner

```
AAAAUCUGGA AAUGUAACUU CUUAUUUCUG GUUGGCCACA UACAUCAACC AUAUUAUUGA
GACCAACAAG CAACAUAGAA AGUGGAAUCC AGUAGCAACA ACAGAGCAAC AAUGGCGACC
AAGAUAUUUU CCCUCCUUAU GCUCCUUGCU CUUUCUGCAU GUGUUGCUAA CGCGACAAUU
UUCCCUCAAU GCUCACAAGC UCCUAUAGCU UCCCUCUUC CCCAUACCU UCCAUCAAUG
AUAGCUUCAG UAUGUGAAAA CCCAGCUCUU CAGCCCUAUA GGCUCCAACA AGCAAUCGCA
GCAAGCAACA UACCUUUAUC ACCCUGUGUG U

FIG. 3A

```
CGAGTGATTC TTTAAACCGA TTATTACACA AGTTAACCAC ACTAAAATTA ACATTGGTGA
GCTCACTAAG AAATTTGGCT AATAATGTGT TCAATTGGTG TGATTTTAAT TGTAACCACT

ATCGTGCCAT GATTTTTTC TAGTGCAAAA TAGCCAAACC AAGCAAAACA TATGTGGCTA
TAGCACGGTA CTAAAAAAAG ATCACGTTTT ATCGGTTTGG TTCGTTTTGT ATACACCGAT

TCGTTACACA TGTGTAAAGG TATTGCATCA CACCATGTC ACCCATGTAT TTGGACAATA
AGCAATGTGT ACACATTCC ATAACGTAGT GTGGTAACAG TGGGTACATA AACCTGTTAT

CCGAGAGGAA AAACCACTTA TTTATTGTAT TTTATCAAGT TTATCTTGCT TACGTATAAA
GGCTCTCCTT TTTGGTGAAT AAATAACATA AAATAGTTCA AATAGAACGA ATGCATATTT

TTATAACCCA ACAAAGTAAT CACTAAATGT CAAAAACCAAC TAGATACCAT GTCATCTCTA
AATATTGGGT TGTTTCATTA GTGATTTACA GTTTTGGTTG ATCTATGGTA CAGTAGAGAT

CCTTATCTTA CTAATATTCT TTTTGCAAAA TCGAAAATTA ATCTTGCACA AGCACAAGGA
GGAATAGAAT GATTATAAGA AAAACGTTTT AGCTTTTAAT TAGAACGTGT TCGTGTTCCT

CTGAGATGTG TATAAATATC TCTTAGATTA GTAGATAATA TATCGCACAT ATTATTGAGA
GACTCTACAC ATATTTATAG AGAATCTAAT CATCTATTAT ATAGCGTGTA TAATAACTCT

CCAACTAGCA ACATAGAAAG CACAATATTG TACCAATAAT GGCAGCCAAA ATATTTGCC
GGTTGATCGT TGTATCTTTC GTGTTATAAC ATGGTTATTA CCGTCGGTTT TATAAAACGG

TCATTATGCT CCTTGGTCTT TCTGCAAGTG CTGCTACGGC GAGCATTTTC CCGCAATGCT
AGTAATACGA GGAACCAGAA AGACGTTCAC GACGATGCCG CTCGTAAAAG GGCGTTACGA

CACAAGCTCC TATAGCTTCC CTTCTTCCCC CATACCTCTC ACCAGCGATG TCTTCAGTAT
GTGTTCGAGG ATATCGAAGG GAAGAAGGGG GTATGGAGAG TGGTCGCTAC AGAAGTCATA

GTGAAAATCC AATTCTTCTA CCCTACAGGA TCCAACAGGC AATCGCAGCA GGCATCTTAC
CACTTTTAGG TTAAGAAGAT GGGATGTCCT AGGTTGTCCG TTAGCGTCGT CCGTAGAATG

CTTTATCACC CTTGTTCCTC CAACAATCAT CAGCCCTATT ACAGCAGTTA CCTTTGGTGC
GAAATAGTGG GAACAAGGAG GTTGTTAGTA GTCGGGATAA TGTCGTCAAT GGAAACCACG
```

FIG. 3B

```
ATTTATTGGC ACAAAACATC AGGGCACAAC AACTACAACA ACTCGTGCTA GCAAACCTTG
TAAATAACCG TGTTTTGTAG TCCCGTGTTG TTGATGTTGT TGAGCACGAT CGTTTGGAAC

CTGCCTACTC TCAGCAACAG CAGTTACCTT TGGTGCATTT GTTGGCACAA AACATCAGGG
GACGGATGAG AGTCGTTGTC GTCAATGGAA ACCACGTAAA CAACCGTGTT TTGTAGTCCC

CACAACAACT ACAACAACTC GTGCTAGCAA ACCTTGCTGC CTACTCTCAG CAACAACAGT
GTGTTGTTGA TGTTGTTGAG CACGATCGTT TGGAACGACG GATGAGAGTC GTTGTTGTCA

TTCTGCCATT CAACCAACTA GCTGCATTGA ACTCTGCTGC TTATTTGCAG CAACAACAAC
AAGACGGTAA GTTGGTTGAT CGACGTAACT TGAGACGACG AATAAACGTC GTTGTTGTTG

TACTACCATT CAGCCAGCTA GCTGCTGCCT ACCCCCCGCA ATTTCTTCCA TTCAACCAAC
ATGATGGTAA GTCGGTCGAT CGACGACGGA TGGGGGGCGT TAAAGAAGGT AAGTTGGTTG

TGGCAGCATT GAACTCTCAT GCTTATGTAC AACAACAACA ACTACTACCA TTCAGCCAGC
ACCGTCGTAA CTTGAGAGTA CGAATACATG TTGTTGTTGT TGATGATGGT AAGTCGGTCG

TAGCTGCTGT GAGCCCTGCT GCCTTCTTGA CACAGCAACA TTTGTTGCCG TTCTACCTGC
ATCGACGACA CTCGGGACGA CGGAAGAACT GTGTCGTTGT AAACAACGGC AAGATGGACG

ACACTGCGCC TAACGTTGGC ACCCTCTTAC AACTGCAACA ATTGCTGCCA TTCGACCAAC
TGTGACGCGG ATTGCAACCG TGGGAGAATG TTGACGTTGT TAACGACGGT AAGCTGGTTG

TTGCTTTGAC AAACCCAGCA GTGTTCTACC AACAACCCAT CATTGGTGGT GCCCTCTTTT
AACGAAACTG TTTGGGTCGT CACAAGATGG TTGTTGGGTA GTAACCACCA CGGGAGAAAA

AGATTGCTTA TGAGTTATAG TTCAATAATA AAGTTTTTT TGCTGATATT TGTGGCTTCC
TCTAACGAAT ACTCAATATC AAGTTATTAT TTCAAAAAAA ACGACTATAA ACACCGAAGG

CAGAAATAAG AAAGTACATT TCTAGATTCT TATGTGCTTC TAGT
GTCTTTATTC TTTCATGTAA AGATCTAAGA ATACACGAAG ATCA
```

A.  PRIMER 1
    5' CCCGGGTAGATAATATATCGCAC 3'

PRIMER 2
    5' CCCGGGCTGCCATTATTGGTACAATATTGTGCTTTCTATG 3'

B.  PRIMER 1
    5' CCCGGGCAAACCTTGCATGCCTACTCTCAGC 3'

PRIMER 2
    5' CCCGGGTAGTAGTTGTTGTTGCATGCAAATAAGCAGC 3'

C.  PRIMER1
    5' CCCGGGTCTAGAGATTGCTTATGAGTTATAGTTCAATA
    ATAAAGTTTTTTGCTGATATTGTGGCTTCCCAG 3'

PRIMER 2
    5' CCCGGGTCTAGAAAATGTACTTTCTTA
    TTTCTGGGAAGCCACAAATATCAGC 3'

FIG. 4

METHOD FOR ALTERING THE NUTRITIONAL CONTENT OF PLANT SEED

CROSS-REFERENCE TO RELATED APPLICATIONS

This application is a continuation-in-part of U.S. application Ser. No. 08/112,245, filed Aug. 25, 1993, currently pending, the disclosure of which is incorporated by reference herein.

FIELD OF THE INVENTION

The invention relates generally to modification of the nutritional content of maize seed utilizing preselected DNA constructs. More specifically, the invention relates to the use of preselected DNA constructs to transform maize plants so as to alter the levels of proteins, such as seed storage proteins, e.g., the prolamines (zeins), in the seeds of transgenic maize plants. Thus, the invention provides a mechanism to replace nutritionally deficient proteins with nutritionally enhanced proteins, and/or to increase the levels of starch, in the seed of transgenic maize plants.

BACKGROUND OF THE INVENTION

In agriculturally important seed crops, the expression of storage protein genes directly affects the nutritional quality of the seed protein. In maize, the prolamine (zein) fraction of storage proteins comprises over 50% of the total protein in the mature seed. The zeins designated α-zein are especially abundant. The α-zein polypeptides contain extremely low levels of the essential amino acids lysine and tryptophan. Thus, maize seed protein is deficient in these amino acids because such a large proportion of the total seed storage protein is contributed by the α-zeins (Mertz et al., 1964).

The development of breeding steps to improve maize based on the manipulation of zein profile is hampered by the complexity of the zein proteins. The term "zein" encompasses a family of some 100 related proteins. Zeins can be divided into four structurally distinct types: α-zeins include proteins with molecular weights of 19,000 and 22,000 daltons; β-zeins include proteins with a molecular weight of 14,000 daltons; γ-zeins include proteins with molecular weights of 27,000 and 26,000 daltons; and δ-zeins include proteins having a molecular weight of 10,000 daltons. The α-zeins are the major zein proteins found in the endosperm of maize kernels. However, the complexity of zein proteins goes beyond these size classes. Protein sequence analyses indicates that there is microheterogenicity in zein amino acid sequences. This is in accord with isoelectric focusing analyses which show charge differences in zein proteins. Over 70 genes encoding the zein proteins have been identified (Rubenstein, 1982), and the zein genes appear to be located on at least three chromosomes. Thus, the zein proteins are encoded by a multigene family.

Based on sequence and hybridization data, the zein multigene family is divided into several subfamilies. Each subfamily is defined by sequence homology to a cDNA clone: A20, A30, B49, B59, or B36. Hybrid-select translation studies which employ B49 and B36 select mRNAs that code for predominantly heavy class (23 kD) α-zein proteins, while A20, A30, and B59 select for predominantly the light class (19 kD) α-zein proteins (Heidecker and Messing, 1986). A comparison of zein sequences in each of the subfamilies A20, A30 and B49 have identified four distinct functional domains (Messing et al., 1983). Region I corresponds to the signal peptide present in most, if not all, zeins. Regions II and IV correspond to the amino and carboxyl termini, respectively, of the mature zein protein. Region III corresponds to the coding region between Regions II and IV, including a region which has tandem repeats of a 20 amino acid sequence.

There are several mutations known to cause reductions in zein synthesis that lead to alterations in the amino acid content of the seed. For example, in the seeds of plants homozygous for the recessive mutation opaque-2, the zein content is reduced by approximately 50% (Tsai et al., 1978). The opaque-2 mutation primarily affects synthesis of the 19 and 22 kD α-zein proteins, causing a significant decrease in the level of the 19 kD zein fraction and reducing the accumulation of the 22 kD zein fraction to barely detectable levels (Jones et al., 1977). In this mutant, there is a concomitant increase in the proportion of more nutritionally balanced proteins, e.g., albumins, globulins and glutelins, deposited in the seed. The net result of the altered storage protein patterns is an increase in the essential amino acids lysine and tryptophan in the mutant seed (Misra et al., 1972).

Two other recessive mutations, floury-2 and sugary-1, result in increased levels of methionine in the seed. The increased methionine content in the seeds of floury-2 mutants is the result of a decrease in the zein/glutelin ratio, due to reductions in the levels of both the 19 and 22 kD α-zein fractions, and an apparent increase in the methionine content of the glutelin fraction (Hansel et al., 1973; Jones, 1978). In sugary-I mutants, there is a decrease in zein synthesis coupled with an increase in the methionine content of the zein and glutelin fractions (Paulis et al., 1978).

As demonstrated by the opaque-2, floury-2, and sugary-1 mutations, reductions in zein synthesis and/or changes in the relative proportions of the storage protein fractions can affect the overall amino acid composition of the seed. Unfortunately, poor agronomic characteristics (kernel softness, reduced yield, lowered resistance to disease) are associated with the opaque and floury mutations, preventing their ready application in commercial breeding.

Another way that genes can be down regulated in animals and plants involves the expression of antisense genes. A review of the use of antisense genes in manipulating gene expression in plants can be found in van der Krol et al. (1988a; 1988b). The inhibition of expression of several endogenous plant genes has been reported. For example, U.S. Pat. No. 5,107,065 discloses down regulation of polygalacturonase activity by expression of an antisense gene. Other plant genes down regulated using antisense genes include the genes encoding chalcone synthase and the small subunit of ribulose-1,5-biphosphate carboxylase (van der Krol et al., 1988c; Rodernel et al., 1988). However, to date there has been no description of attempts to use antisense technology to alter the nutritional content of seeds.

Down regulation of gene expression in a plant may also occur through expression of a particular transgene. This type of down regulation is referred to as co-suppression and involves coordinate silencing of a transgene and a second transgene or a homologous endogenous gene (Matzke and Matzke, 1995). For example, cosuppression of a herbicide resistance gene in tobacco (Brandle et al., 1995), polygalacturonidase in tomato (Flavell, 1994) and chalcone synthase in petunia (U.S. Pat. No. 5,034,323) have been demonstrated. Flavell (1994) suggested that multicopy genes, or gene families, must have evolved to avoid cosuppression in order for multiple copies of related genes to be expressed in a plant.

Thus, there is a need for a method to alter the nutritional content of seeds and produce kernels with good agronomic characteristics, including maintaining kernel hardness, yield, and disease resistance of the parent genotype. Furthermore, there is a need for a method to decrease expression of seed storage proteins of poor nutritional quality while increasing proteins with higher contents of nutritionally advantageous amino acids, such as methionine and lysine, and/or while increasing the starch content of seeds.

SUMMARY OF THE INVENTION

The invention provides methods which employ a genetically engineered, preselected DNA sequences or segments to alter the nutritional content of plant seeds. The expression of said preselected DNA sequence results in an altered protein and/or amino acid composition in the transgenic plant, plant tissue, plant part, or plant cell relative to the corresponding nontransformed, i.e., nontransgenic, plant, plant tissue, plant part, or plant cell. Preferably, the seeds of said transgenic plant have an increased amount, e.g., weight percent, of at least one amino acid essential to the diet of animals, relative to nontransformed, i.e., nontransgenic, seeds. An increase in the weight percent of at least one amino acid essential to the diet of animals, e.g., lysine, methionine, isoleucine, tryptophan, or threonine, in seeds increases the nutritional value of those seeds for animal, e.g., feeds for poultry and swine, or human consumption.

Thus, the invention provides a method which comprises stably transforming cells of a plant with an expression cassette. The expression cassette comprises a preselected DNA sequence which codes for an RNA molecule which is substantially identical (sense), or complementary (antisense), to all or a portion of a messenger RNA ("target" mRNA), i.e., an endogenous or "native" mRNA, which is present in an nontransformed plant cell. The target mRNA encodes a plant seed storage protein, preferably a protein which is deficient in at least one amino acid, and more preferably deficient in an amino acid which is essential to the diet of animals.

The resultant transformed cells are used to regenerate fertile transgenic plants which in turn yield transgenic seeds, wherein the preselected DNA sequence is expressed in the transgenic seeds in an amount effective to substantially reduce or decrease the amount, weight percent or level of a seed storage protein relative to the amount, weight percent or level of said seed storage protein present in the corresponding nontransgenic seeds, e.g., seeds of a nontransformed R0 control plant or corresponding nontransformed seeds isolated from the transgenic plant. The seed storage protein is one which is deficient in at least one amino acid essential to the diet of an animal. Preferably, the decrease in the amount of the seed storage protein results in an increase in the weight percent of seed storage proteins comprising higher percentages of nutritionally advantageous amino acids. The preselected DNA sequence preferably codes for an RNA molecule substantially complementary to all or a portion of a mRNA coding for a 19 kD or 22 kD α-zein protein. A reduction in seed storage proteins, e.g., the α-zeins, may be accompanied by a decrease in the degree of kernel hardness. Hardness of the kernel may be enhanced in these cases by modification of the kernel phenotype as described for the opaque-2 mutation (Lopes and Larkins, 1991) or by genetically modifying plants to increase the levels of certain endosperm proteins such as the 27 kD γ-zein.

The genetically engineered DNA sequences of the invention are "preselected" in that the coding regions contained therein have been isolated in vitro, and identified at least functionally. Thus, a "preselected" DNA is a DNA sequence or segment that has been isolated from a cell, purified, and amplified. The choice of the preselected DNA sequence will be based on the amino acid composition of the polypeptide encoded by the sense strand of a preselected DNA sequence, and preferably, the ability of the polypeptide to accumulate in seeds. Preferably, the number of said coding regions has also been ascertained. Also preferably, the isolated DNA molecule is "recombinant" in that it contains preselected DNA sequences from different sources which, preferably, have been linked to yield chimeric expression cassettes. The preselected DNA sequences are preferably about 2-3 kb.

The invention further provides a method to increase the starch content of a plant, plant part, plant tissue or plant cell. The method comprises stably transforming cells of a plant with an expression cassette. The expression cassette comprises a preselected DNA sequence coding for an RNA molecule substantially identical, or complementary, to all or a portion of at least one mRNA coding for a plant seed storage protein. Preferably, the preselected DNA sequence is operably linked to a promoter functional in a plant and/or seed. Transformed cells are used to regenerate fertile transgenic plants and seeds. The preselected DNA sequence is preferably expressed in the transgenic seeds in an amount effective to decrease the weight percent of seed storage protein in the transgenic seed over the weight percent of seed storage protein present in the corresponding nontransgenic seed. The preselected DNA sequence is also preferably expressed in the transgenic seeds in an amount effective to increase the weight percent of starch in the transgenic seed over the weight percent of starch present in the corresponding nontransgenic seed. An increase in the weight percent of the starch of seeds improves the food value of the seed, or its value as a source of starch for use in processed food products or in various industrial applications. Moreover, an increase in starch content in transgneic seeds can result in an increase in the starch recovered from those seeds.

Also provided is a method to inhibit a family or subfamily of seed storage proteins. Seed storage proteins such as the zein proteins of maize are encoded in a multigene family. Portions of the amino acid sequence of, and DNA sequences encoding, seed storage proteins in a given family share amino acid, and DNA, sequence homology, respectively (termed "family"-specific sequences). Other portions of the amino acid sequence of, and DNA sequences encoding, a zein seed storage protein in a subfamily share amino acid, and DNA, sequence homology, respectively, with one another (termed "subfamily"-specific sequences). A preselected DNA sequence corresponding to family-, or subfamily-, specific sequences can be employed to inhibit the production of a family or subfamily of zein proteins. An expression cassette is provided which comprises a preselected DNA sequence encoding an RNA molecule which is substantially identical, or complementary, to all or a portion of a mRNA that is substantially homologous in sequence among members of a family or subfamily of zein proteins. The expression cassette which comprises the preselected DNA sequence is then introduced into plant cells, which are regenerated to yield transgenic plants and seeds. The transgenic seeds are characterized by substantial inhibition of a preselected family or subfamily of seed storage protein. In a preferred embodiment, the preselected DNA sequence encodes an RNA molecule which is substantially complementary to all or a portion of a mRNA coding for a 20 amino acid sequence which is present in multiple, tandem copies in the A20 subfamily of the α-zein proteins.

Another embodiment of the invention comprises plant cells, plant tissue, plant parts or plants stably transformed with at least two preselected DNA sequences. The first preselected DNA sequence encodes an RNA molecule substantially identical, or complementary, to all or a portion of a mRNA encoding a seed storage protein, e.g., an endogenous seed storage protein, preferably one which is relatively deficient in at least one amino acid essential to the diet of animals compared to other seed storage proteins. The second preselected DNA sequence encodes a polypeptide of desired amino acid composition, i.e., a polypeptide comprising at least one amino acid essential to the diet of animals. The polypeptide, preferably, has physical properties which minimize disruption of seed cellular structure and therefore grain quality. It is preferred that each preselected DNA sequence is operably linked to a promoter functional in a plant and/or seed.

Following transformation, transformed plant cells having the first and second preselected DNA sequences stably, i.e., chromosomally, integrated into their genome are selected and used to regenerate fertile transgenic plants and seeds. The transgenic seeds are characterized by the expression of the first DNA sequence in an amount effective to substantially reduce or decrease the amount, weight percent, or level, of the undesirable seed storage protein, or an amino acid present in said protein, over the amount, weight percent, or level, of that seed storage protein, or the amino acid present in that protein, which is present in nontransgenic seeds. The transgenic seeds are also preferably characterized by the expression of the second DNA sequence as a plant protein in an amount effective to yield an increase in the amount, weight percent or level of at least one amino acid essential to the diet of animals over the amount, weight percent or level of that amino acid present in nontransgenic seeds.

In a preferred embodiment, the expression of the first preselected DNA sequence in transgenic maize seed inhibits the weight percent of 19 kD or 22 kD α-zein. In another preferred embodiment, the expression of the second preselected DNA sequence in transgenic seed results in an increase in the weight percent of a 10 kD δ-zein protein. In yet another preferred embodiment, the expression of the second preselected DNA sequence in transgenic seed results in an increase in the weight percent of a 27 kD zein protein. In yet another preferred embodiment, the second preselected DNA encodes a synthetic polypeptide, such as MB1 (Beauregard et al., 1995). MB1 is a stable synthetic polypeptide highly enriched in amino acids essential for animal nutrition (e.g., methionine, threonine, lysine, and leucine) which also adopts an α-helical conformation. The synthetic polypeptide MB1 shares some properties of maize zein proteins, e.g., MB1 is alcohol soluble and contains multiple α-helical domains. However, other polypeptides, synthetic and naturally occurring, with preselected desired amino acid compositions, and genes coding therefor, could be employed in the practice of the invention. As used herein, the term "polypeptide" includes protein.

The invention also provides a method to increase the amount, weight percent or level of a polypeptide in a plant. The method comprises stably transforming plants, plant cells, plant tissue or plant parts with a first preselected DNA sequence which encodes a seed storage protein and a second preselected DNA sequence which encodes at least a portion of a preselected, desired polypeptide. The polypeptide may be encoded by the genome of the nontransformed plant or plant cell ("endogenous" or "native"), or, alternatively may not be native to, i.e., present in, the genome of the nontransformed "wild type" plant or plant cell (termed "heterologous," "non-native" or "foreign"). Preferably, the second preselected DNA sequence encodes a bacterial enzyme, e.g., AK, DHDPS, EPSPS, a bacterial toxin, e.g., the crystal toxin from Bt, a seed storage protein, e.g., Z27, or a non-maize seed storage protein, such as nut and legume seed storage proteins. See, for example, U.S. Pat. No. 4,769,061; U.S. Pat. No. 4,971,908; PCT/US90/04462; PCT/WO89/11789; and Altenbach et al. (1989).

Transformed plant cells having the first and second preselected DNA sequences stably, i.e., chromosomally, integrated therein are selected and used to regenerate fertile transgenic plants and seeds. Transgenic seeds of the invention are characterized by substantial inhibition of the expression of at least one seed storage protein. The second preselected DNA sequence is expressed in said transgenic seeds in an amount effective to increase the weight percent of at least one amino acid present in polypeptide encoded by the second preselected DNA sequence relative to the weight percent of that amino acid in nontransgenic seeds. Alternatively, the second preselected DNA sequence is expressed in transgenic seed in an amount effective to increase the amount, weight percent or level of the polypeptide relative to the amount, weight percent or level of the polypeptide present in a seed transformed with the second preselected DNA sequence alone.

The invention also provides preselected DNA sequences and expression cassettes useful in the methods described above, as well as fertile transgenic plants and/or seeds produced thereby. Preferred fertile transgenic plants and seeds of the invention exhibit an increase in the weight percent of at least one amino acid essential to the diet of animals and/or an increase in the starch content. The fertile transgenic plants and seeds are used to generate true breeding plants so that lines of plants can be developed which transmit the increase in amino acid or starch content in a dominant fashion while still maintaining the functional agronomic characteristics of elite inbred lines. Other embodiments of the invention include plant cells, plant parts, plant tissue and microorganisms transformed with the preselected DNA sequences.

BRIEF DESCRIPTION OF THE FIGURES

FIG. 2 is the RNA sequence of A20 (SEQ ID NO:1).

FIG. 3 is the DNA sequence of Z4 (SEQ ID NO:2).

FIG. 4 shows oligonucleotide primers which target the cap site (A) (SEQ ID NO:9 and SEQ ID NO:10), domain IIIB (B) (SEQ ID NO:11 and SEQ ID NO:12), and the poly(A) region (C) (SEQ ID NO:13 and SEQ ID NO:15) of the Z4 gene.

DETAILED DESCRIPTION OF THE INVENTION

Definitions

Figure 1:
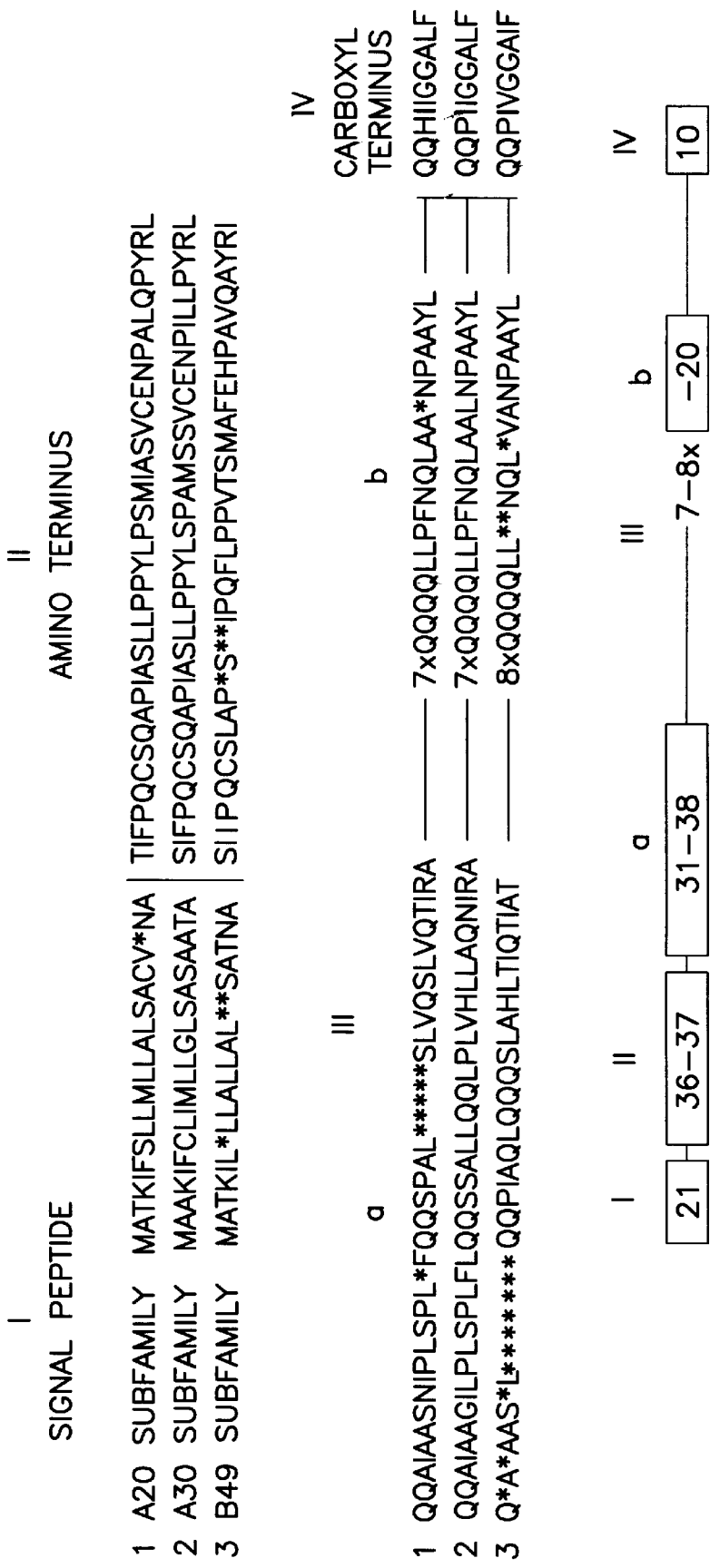
FIG. 1 is a schematic depicting the functional domains of zein proteins. A consensus amino acid sequence for each of the zein subfamilies is shown. Domains I–IV are shown. Shown in Region IIIb is a consensus of the repetitive portion of the zein proteins. Asterisks indicate a lack of consensus at that position. Dots represent gaps inserted to align the sequences.

As used herein, "substantially identical" or "substantially homologous" in sequence means that two nucleic acid, or amino acid, sequences have at least about 65%, preferably about 70%, more preferably about 90%, and even more preferably about 98%, sequence identity, or homology, to each other. An RNA molecule encoded by a first preselected DNA sequence of the invention has sufficient sequence identity or homology to cause co-suppression of the expression of the homologous endogenous gene or expression of a second preselected DNA sequence which has substantial identity to the first preselected DNA sequence.

As used herein, "substantially complementary" means that two nucleic acid sequences have at least about 65%, preferably about 70%, more preferably about 90%, and even more preferably about 98%, sequence complementarity to each other. A substantially complementary RNA molecule is one that has sufficient sequence complementarity to the mRNA encoding a seed storage protein to result in a reduction or inhibition of the translation of the mRNA.

As used herein, "substantial reduction," or "substantial decrease" means that a transgenic plant, plant part, plant cell or plant tissue has a reduced or decreased amount, level or weight percent of a particular amino acid, or polypeptide, relative to the amount, level or weight percent of that amino acid, or polypeptide, in the corresponding nontransgenic plant, plant part, plant cell or plant tissue. Preferably, the decreased amount, level or weight percent of that amino acid, or polypeptide, in the transgenic plant, plant part, plant tissue or plant cell is about 10–100% and more preferably about 70%–100%, and even more preferably about 80–100%, relative to the amount, level or weight percent of that amino acid, or polypeptide, in the corresponding non-transgenic plant, plant part, plant cell or plant tissue.

As used herein, "increased" or "elevated" levels, amounts or weight percents of a polypeptide or amino acid in a transformed (transgenic) plant cell, plant tissue, plant part, or plant, are greater than the levels, amounts or weight percents of that polypeptide or amino acid in the corresponding untransformed plant cell, plant part, plant tissue, or plant. An increase in the weight percent of an amino acid is an increase of about 1–50%, preferably about 5–40%, and more preferably about 10–30%, in the weight percent of the amino acid in a transgenic plant, plant part, plant tissue, or plant cell relative to the weight percent of that amino acid in a corresponding nontransgenic plant, plant part, plant tissue, or plant cell. An increase in the amount of a polypeptide in a transgenic plant, plant part, plant tissue or plant cell is preferably at least about 2–100 fold, more preferably at least about 3–80 fold, and even more preferably at least about 5–30 fold, relative to the amount of that polypeptide in the corresponding nontransgenic plant, plant part, plant tissue or plant cell.

For example, the average lysine content in maize seed is about 0.24–0.26%, the average methionine content in maize seed is about 0.17–0.19%, and the average tryptophan content in maize seed is about 0.08–0.10% (Dale, 1996). Thus, the expression of a preselected DNA sequence of the invention in seeds results in an increase in content of methionine, tryptophan or lysine in those seeds. The amino acid composition of a polypeptide can be determined by methods well known to the art (Jarrett et al., 1986; Jones et al., 1983; AACC, 1995).

As used herein, "genetically modified" or "transgenic" means a plant cell, plant part, plant tissue or plant which comprises a preselected DNA segment which is introduced into the genome of a plant cell, plant part, plant tissue or plant by transformation. The term "wild type" refers to an untransformed plant cell, plant part, plant tissue or plant, i.e., one where the genome has not been altered by the presence of the preselected DNA segment.

As used herein, "plant" refers to either a whole plant, a plant tissue, a plant part, such as pollen or an embryo, a plant cell, or a group of plant cells. The class of plants which can be used in the method of the invention is generally as broad as the class of seed-bearing higher plants amenable to transformation techniques, including both monocotyledonous and dicotyledonous plants. Seeds derived from plants regenerated from transfonned plant cells, plant parts or plant tissues, or progeny derived from the regenerated transformed plants, may be used directly as feed or food, or can be altered by further processing. In the practice of the present invention, the most preferred plant seed is that of corn or *Zea mays*. The transformation of the plants in accordance with the invention may be carried out in essentially any of the various ways known to those skilled in the art of plant molecular biology. These include, but are not limited to, microprojectile bombardment, microinjection, electroporation of protoplasts or cells comprising partial cell walls, and Agrobacterium-mediated DNA transfer.

As used herein, the term "a seed storage protein deficient in at least one amino acid that is essential to the diet of an animal" means that the protein has a lower than average weight percent of at least one amino acid which is essential to the diet of an animal. Amino acids which are essential to the diet of animals include arginine, histidine, isoleucine, Icucine, lysine, methionine, phenylalanine, threonine, tryptophan and valine. Preferred amino acids which are essential in the diet of animals include methionine, threonine, lysine, isoleucine, tryptophan, and mixtures thereof. A plant seed storage protein can contain one or more of these essential amino acids. For example, the average weight percent of lysine in a maize seed is about about 0.24–0.26%. Thus, a seed storage protein, such as an α-zein, which does not comprise lysine, is deficient in lysine. The average weight percent of a particular amino acid is determined by methods well known to the art.

As used herein, "isolated" means either physically isolated from the cell or synthesized in vitro in the basis of the sequence of an isolated DNA segment.

As used herein, a "native" gene means a DNA sequence or segment that has not been manipulated in vitro, i.e., has not been isolated, purified, and amplified.

I. DNA Molecules of the Invention
A. Isolation of Preselected Sense and Antisense DNA Sequences
1. α-Zein Seed Storage Proteins A genetically engineered, isolated purified DNA molecule useful in the invention can comprise a preselected DNA sequence encoding an RNA molecule substantially homologous, or complementary, to all or a portion thereof of a mRNA coding for a plant seed storage protein, e.g., one of the α-zein proteins. As used herein, a "seed storage protein" is a protein which is one of the major proteins in mature seeds of plants such as maize, and comprises a signal peptide sequence at the amino terminal end of the pre-form of the protein, and which comprises a tandem repeat of amino acid sequences in the mature form of the protein.

Plant seed storage proteins or zein proteins include, but are not limited to, zein proteins, such as α-zeins, e.g., proteins of 19,000 and 22,000 daltons; β-zein proteins, e.g., proteins with a molecular weight of 14,000 daltons; γ-zein proteins, e.g., proteins with molecular weights of 27,000 and 16,000 daltons; and δ-zein proteins, i.c., proteins with a molecular weight of 10,000 daltons. Certain seed storage proteins are deficient in at least one amino acid essential to the diet of animals. For example, the 19 kD and 22 kD α-zein proteins contain low levels of the amino acids lysine and tryptophan which are essential to the diet of animals.

In an alternative embodiment, the preselected DNA sequence is expressed as a RNA molecule that is substantially complementary to, or identical to, respectively, all or a portion of a family-, or subfamily-, of seed storage protein specific mRNA. The RNA molecule, or corresponding DNA sequence, has about 65%, or more preferably 90%, nucleic acid sequence homology or complementarity with other RNA, or DNA, respectively, sequences which encode seed storage proteins of the same family or subfamily. The expression of a preselected antisense DNA sequence substantially inhibits translation of the complementary mRNA, while the expression of a preselected sense DNA sequence results in cosuppression of the expression of endogenous DNA sequences encoding the homologous seed storage proteins. A preferred preselected DNA molecule encodes an RNA molecule which is complementary to the DNA sequence which encodes the tandem repeat region of 20 amino acids of the same family or subfamily of seed storage proteins.

The preselected sense or antisense DNA sequence can encode an RNA molecule preferably having about 15 nucleotides to 2,000 nucleotides and more preferably about 50–1,000 nucleotides. The DNA sequence can be derived from the 5' terminus or the 3' terminus and can include all or only a portion of the coding and/or noncoding regions. It will be understood by those of skill in the art that a sense or antisense DNA sequence should provide an RNA sequence having at least about 15 nucleotides in order to provide for substantial inhibition of the expression of the mRNA coding for the seed storage protein.

The preselected DNA sequences of the invention are obtained by cloning a DNA molecule, sequence or segment which encodes, and can be expressed as a mRNA of, a seed storage protein. Portions of the preselected DNA sequence can also include noncoding nucleotides located at either the 5' or 3' ends of the sense coding sequence. A preselected DNA sequence which encodes an RNA sequence that is substantially complementary to a mRNA sequence encoding a seed storage protein is typically a "sense" DNA sequence cloned in the opposite orientation (i.e., 3' to 5' rather than 5' to 3'). A sense DNA sequence encoding a seed storage protein can be cloned using standard methods as described in Sambrook et al. (1989), and U.S. Pat. No. 5,508,468.

A subfragment of a preselected DNA sequence which encodes a full-length seed storage protein can be generated using restriction enzymes. The subfragment is preferably selected based upon the known functional domains of seed storage proteins. A seed storage protein has at least four different functional domains: a signal peptide domain, a domain which includes the amino terminal portion of the mature protein which is located downstream of the signal peptide, a domain which includes tandem repeats of a 20 amino acid sequence which is located downstream of the amino terminus of the mature protein, and a domain which includes the carboxy terminus of the protein. The size and location of these functional domains in the α-zein proteins are shown in FIG. 1 and can be determined for other seed storage proteins by comparing the amino acid sequence of other seed storage proteins to the amino acid sequence of the α-zein proteins.

Suitable examples of preselected DNA sequences that can provide all or a portion of a sense or antisense seed storage protein, e.g., α-zein, DNA sequence include cDNA clones A20, A30, B49, B59, B36, Z4, and Z15 prepared as described by Messing et al. (1983). Preferred cDNA clones are an A20 clone, which encodes a 19 kD α-zein protein, and a Z4 clone, which encodes a 22 kD δ-zein protein. Portions of the Z4 and the A20 DNA sequences can be generated with restriction endonucleases.

It is also contemplated that preselected DNA sequences homologous or complementary to any portion of the A20 or Z4 RNA, in vectors appropriate for expression in plants, may be used to substantially decrease the production of seed storage proteins. Examples of such DNA sequences are sequences which may be homologous or complementary to the 5' region of the DNA or RNA sequence such as the 3' region of the promoter and the cap site (FIG. 4A), or the 3' region of the gene such as the AATAAA-like polyadenylation signal, upstream of the poly(A) tail (FIG. 4C). It is further contemplated that a preselected DNA sequence homologous or complementary to a conserved domain common to more than one gene in a gene family or subfamily, such as domain IIIB or one or more of the other domains shown in FIG. 1, may also be useful to substantially inhibit the expression of members of the gene family or subfamily (FIG. 4B). It is further contemplated that the preselected DNA sequence may encode an RNA molecule which is substantially identical to all or a portion of a mRNA encoding a seed storage protein, e.g., a preselected DNA sequence encoding a RNA molecule substantially identical to the mRNA encoding 10 kD zein, 27 kD zein, or MB1.

In a preferred embodiment, a sense DNA sequence encoding a 19 kD α-zein protein and/or a sense DNA sequence encoding a 22 kD α-zein protein is prepared from a cDNA library generated from endosperm tissue as described in Hu et al. (1982) and Geraghty et al. (1982), which are hereby incorporated by reference. The cDNA clones encoding a 19 kD α-zein protein and/or a 22 kD α-zein protein can be characterized by standard methods such as DNA hybridization or detection of gene expression by immunotechniques including Western blot analysis. The presence of the coding sequence of the 19 kD or 22 kD α-zein protein can be confirmed by DNA sequencing.

2. Other Preselected DNA Sequences

Another preselected DNA sequence useful in the method of the invention encodes a polypeptide, including a plant protein, comprising at least one amino acid essential to the diet of animals operably linked to a promoter functional in a plant and/or seeds. The expression of the preselected DNA sequence, coding for the polypeptide comprising at least one amino acid essential to the diet of animals, in a plant cell provides for an increase in expression of the polypeptide so that the weight percent of the amino acid residue is substantially increased in the plant regenerated from the transformed plant cell, or seed derived from said plant, over the amount normally present in the corresponding untransformed plant or seed. Preferably, the preselected DNA sequence is co-transformed into plant cells with a second preselected antisense or sense DNA sequence, the expression of which results in the inhibition of expression of a seed storage protein relatively deficient in an amino acid essential in the diet of animals.

The preselected DNA sequence coding for a polypeptide comprising at least one amino acid essential in the diet of animals may be a polypeptide expressed in a plant seed, such as a 10 kD zein protein. Other polypeptides that contain one or more amino acid residues essential in the diet of animals include the synthetic polypeptide MB1 (Beauregard et al., 1995). It is contemplated that any gene encoding a naturally occurring polypeptide, or a synthetic polypeptide, that contains at least one amino acid essential in the diet of an animal may be used in the present invention. The Z10 and MB1 proteins are illustrative of a naturally occurring protein and a synthetic polypeptide, respectively, although one of skill in the art will realize that many other proteins are useful in the practice of the present invention.

The preselected DNA sequences encoding these polypeptides can be obtained by standard methods, as described by Sambrook et al., cited supra. For example, a cDNA clone encoding a 10 kD zein protein can be obtained from maize endosperm tissue, as described by Kirihara et al. (1988). The DNA sequence is then preferably combined with a promoter that is functional in plant cells or seeds. The preferred promoter is a promoter functional during plant seed development, such as the Z27 or Z10 promoter.

The gene encoding the synthetic polypeptide MB1 is obtained from Mary A. Hefford (Center for Food and Animal Research, Agriculture and Agri-Food Canada). The preselected DNA sequence encoding a synthetic polypeptide such as MB1 is operably linked to a signal sequence derived from a seed storage protein. For example, the MB1 DNA sequence can be operably linked to the 15 kD zein signal peptide sequence.

It is also contemplated that a preselected DNA sequence encodes a desirable seed storage protein. Thus, the expression of a first preselected DNA sequence can inhibit the expression of an undesirable seed storage protein, while the expression of a second preselected DNA sequence can encode a desirable gene product, e.g., a desirable seed storage protein. For example, it is envisioned that the expression of the first preselected DNA sequence, which comprises partial gene DNA sequences, may be advantageous for the suppression of the expression of undesirable seed storage proteins, if those partial DNA sequences target DNA or RNA sequences not present in the second preselected DNA sequence which encodes a desirable polypeptide, e.g., 10 kD zein or MB1, in order to avoid suppression of expression of the desirable polypeptide.

B. Optional Sequences for Expression Cassettes

1. Promoters

Preferably, the preselected DNA sequence of the invention is operably linked to a promoter, which provides for expression of the preselected DNA sequence. The promoter is preferably a promoter functional in plants and/or seeds, and more preferably a promoter functional during plant seed development. A preselected DNA sequence is operably linked to the promoter when it is located downstream from the promoter, to form an expression cassette.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the $P_{tac}$ promoter can be induced to varying levels of gene expression depending on the level of isothiopropylgalactoside added to the transformed bacterial cells. Promoters can also provide for tissue specific or developmental regulation. An isolated promoter sequence that is a strong promoter for heterologous DNAs is advantageous because it provides for a sufficient level of gene expression to allow for easy detection and selection of transformed cells and provides for a high level of gene expression when desired.

Preferred expression cassettes will generally include, but are not limited to, a plant promoter such as the CaMV 35S promoter (Odell et al., 1985), or others such as CaMV 19S (Lawton et al., 1987), nos (Ebert et al., 1987), Adh1 (Walker et al., 1987), sucrose synthase (Yang et al., 1990), α-tubulin, ubiquitin, actin (Wang et al., 1992), cab (Sullivan et al., 1989), PEPCase (Hudspeth et al., 1989) or those associated with the R gene complex (Chandler et al., 1989). Further suitable promoters include cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., 1971) and the actin promoter from rice (McElroy et al., 1990); seed specific promoters, such as the phaseolin promoter from beans, may also be used (Sengupta-Gopalan, 1985). The especially preferred promoter is functional during plant seed development, such as the Z10 or Z27 promoters. Other promoters useful in the practice of the invention are known to those of skill in the art.

Alternatively, novel tissue-specific promoter sequences may be employed in the practice of the present invention. cDNA clones from a particular tissue are isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

A preselected DNA sequence can be combined with the promoter by standard methods as described in Sambrook et al., cited supra, to yield an expression cassette. Briefly, a plasmid containing a promoter such as the 35S CaMV promoter can be constructed as described in Jefferson (1987) or obtained from Clontech Lab in Palo Alto, Calif. (e.g., pBI121 or pBI221). Typically, these plasmids are constructed to have multiple cloning sites having specificity for different restriction enzymes downstream from the promoter. The preselected DNA sequence can be subcloned downstream from the promoter using restriction enzymes and positioned to ensure that the DNA is inserted in proper orientation with respect to the promoter so that the DNA can be expressed as sense or antisense RNA. Once the preselected DNA sequence is operably linked to a promoter, the expression cassette so formed can be subcloned into a plasmid or other vector.

Once the preselected sense DNA sequence is obtained, all or a portion of the DNA sequence can be subcloned into an expression vector (see below) in the opposite orientation (i.e., 3' to 5'). Similarly, all or a portion of the preselected DNA sequence can be subcloned in sense orientation (i.e., 5' to 3'). The preselected DNA sequence is subcloned downstream from a promoter to form an expression cassette.

In a preferred embodiment, a cDNA clone encoding a Z4 22 kD α-zein protein is isolated from maize endosperm tissue. Using restriction endonucleases, the entire coding sequence for the Z4 gene is subcloned in the 3' to 5' orientation into an intermediate vector to form an antisense DNA sequence. The promoter region from a 10 kD zein protein, designated the Z10 promoter, is subcloned upstream from the antisense DNA sequence which includes the entire coding sequence for the Z4 gene to form an expression cassette. This expression cassette can then be subcloned into a vector suitable for transformation of plant cells. In another preferred embodiment of the present invention, the promoter region from 27 kD zein protein, designated the Z27 promoter, is subcloned upstream from the antisense DNA sequence.

In another preferred embodiment of the present invention, using restriction endonucleases, the entire coding sequence of the A20 gene encoding a 19 kD α-zein protein is subcloned in the 3' to 5' orientation into an intermediate vector to form an antisense DNA sequence. The Z10 promoter, or alternatively the Z27 promoter, is cloned upstream from the A20 antisense DNA sequence. Partial Z4 or A20 DNA sequences can also be cloned in an antisense 3' to 5' orientation downstream of the Z10 or Z27 promoter. Furthermore, it is contemplated that expression cassettes may be constructed which comprise the Z10 or Z27 promoter upstream of a partial or entire Z4 or A20 DNA sequences wherein said DNA sequences are subcloned downstream of the promoter in a 5' to 3' sense orientation.

2. Targeting Sequences

Additionally, expression cassettes can be constructed and employed to target the product of the preselected DNA sequence or segment to an intracellular compartment within plant cells or to direct a protein to the extracellular environment. This can generally be achieved by joining a DNA sequence encoding a transit or signal peptide sequence to the coding sequence of the preselected DNA sequence. The resultant transit, or signal, peptide will transport the protein to a particular intracellular, or extracellular destination, respectively, and can then be post-translationally removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3. 3' Sequences

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. Preferred 3' elements are derived from those from the nopaline synthase gene of *Agrobacterium tumefaciens* (Bevan et al., 1983), the terminator for the T7 transcript from the octopine synthase gene of *Agrobacterium tumefaciens*, and the 3' end of the protease inhibitor I or II genes from potato or tomato, although other 3' elements known to those of skill in the art can also be employed. These 3' nontranslated regulatory sequences can be obtained as described in An (1987) or are already present in plasmids available from commercial sources such as Clontech, Palo Alto, Calif. The 3' nontranslated regulatory sequences can be operably linked to the 3' terminus of the preselected DNA sequence by standard methods.

4. Selectable and Screenable Marker Sequences

In order to improve the ability to identify transformants, one may desire to employ a selectable or screenable marker gene as, or in addition to, the expressible preselected DNA sequence or segment. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, and which polypeptide includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of the maize HPRG (Stiefel et al., 1990) is preferred as this molecule is well characterized in terms of molecular biology, expression, and protein structure. However, any one of a variety of extensins and/or glycine-rich wall proteins (Keller et al., 1989) could be modified by the addition of an antigenic site to create a screenable marker.

Elements of the present disclosure are exemplified in detail through the use of particular marker genes. However in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant cell, e.g., a monocot cell.

Possible selectable markers for use in connection with the present invention include, but are not limited to, a neo gene (Potrykus et al., 1985) which codes for kanamycin resistance and can be selected for using kanamycin, G418, and the like; a bar gene which codes for bialaphos resistance; a gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker et al., 1988); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., 1988); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571, 1987).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein). The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death. The success in using this selective system in conjunction with monocots was particularly surprising because of the major difficulties which have been reported in transformation of cereals (Potrykus, 1989).

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., 1986), which allows for bioluminescence detection; or an aequorin gene (Prasher et al., 1985), which may be employed in calcium-sensitive bioluminescence detection, or a green fluorescent protein gene (Niedz et al., 1995).

Genes from the maize R gene complex are contemplated to be particularly useful as screenable markers. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of aize can be utilized if the Cl and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

5. Other Optional Sequences

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An, cited supra, and is available from Dr. An. This binary Ti vector can be replicated in prokaryotic bacteria such as *E. coli* and Agrobacterium. The Agrobacterium plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

C. In Vitro Screening of Expression Cassettes

Once the expression cassette is constructed and subcloned into a suitable plasmid, it can be screened for the ability to substantially inhibit the translation of a mRNA coding for a seed storage protein by standard methods such as hybrid arrested translation. For example, for hybrid selection or arrested translation, a preselected antisense DNA sequence is subcloned into an SP6/T7 containing plasmids (as supplied by ProMega Corp.). For transformation of plants cells, suitable vectors include plasmids such as described herein. Typically, hybrid arrest translation is an in vitro assay which measures the inhibition of translation of a mRNA encoding a particular seed storage protein. This screening method can also be used to select and identify preselected antisense DNA sequences that inhibit translation of a family or subfamily of zein protein genes. As a control, the corresponding sense expression cassette is introduced into plants and the phenotype assayed.

II. DNA Delivery of the DNA Molecules into Host Cells

The present invention generally includes steps directed to introducing a preselected DNA sequence, such as a preselected cDNA, into a recipient cell to create a transformed cell. The frequency of occurrence of cells taking up exogenous (foreign) DNA is believed to be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

The invention is directed to any plant species wherein the seed contains storage proteins that contain relatively low levels, or none, of at least one essential amino acid. Cells of the plant tissue source are preferably embryogenic cells or cell-lines that can regenerate fertile transgenic plants and/or seeds. The cells can be derived from either monocotyledons or dicotyledons. Suitable examples of plant species include wheat, rice, Arabidopsis, tobacco, maize, soybean, and the like. The preferred cell type is a monocotyledon cell such as a maize cell, which may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. No. 5,384,253 and U.S. Pat. No. 5,472,869, incorporated herein by reference; Dekeyser et al., 1990); direct DNA transfer to plant cells by PEG precipitation (Hayashimoto et al., 1990); direct DNA transfer to plant cells by microprojectile bombardment (McCabe et al., 1988; Gordon-Kamm et al., 1990; U.S. Pat. No. 5,489,520; U.S. Pat. No. 5,538,877; and U.S. Pat. No. 5,538,880, incorporated herein by reference) and DNA transfer to plant cells via infection with Agrobacterium. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

The preferred method for dicot transformation is via infection of plant cells with *Agrobacterium tumefaciens* using the leaf-disk protocol (Horsch et al., 1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. No. 5,384,253; and U.S. Pat. No. 5,472, 869). For example, embryogenic cell lines derived from immature *Zea mays* embryos can be transformed by accelerated particle treatment as described by Gordon-Kamm et al. (1990) or U.S. Pat. No. 5,489,520; U.S. Pat. No. 5,538, 877 and U.S. Pat. No. 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128 (incorporated herein by reference).

The transformation is carried out under conditions directed to the plant tissue of choice. The plant cells or tissue are exposed to the DNA carrying the preselected DNA sequences for an effective period of time. This may range from a less-than-one-second pulse of electricity for electroporation to a 2–3 day co-cultivation in the presence of plasmid-bearing Agrobacterium cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

A. Electroporation

Where one wishes to introduce DNA by means of electroporation, it is contemplated that the method of Krzyzek et al. (U.S. Pat. No. 5,384,253, incorporated herein by reference) will be particularly advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

B. Microprojectile Bombardment

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucoronidase or bar gene engineered for expression in maize. Bacteria were inactivated by ethanol dehydration prior to bombardment. A low level of transient expression of the β-glucoronidase gene was observed 24–48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al., 1988), the formation of partially degraded cells, or the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., 1990). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Results from such small scale optimization studies are disclosed herein and the execution of other routine adjustments will be known to those of skill in the art in light of the present disclosure.

III. Production and Characterization of Stable Transgenic Maize

After effecting delivery of a preselected DNA sequence to recipient cells by any of the methods discussed above, the next steps of the invention generally concern identifying the transformed cells for further culturing and plant regeneration. As mentioned above, in order to improve the ability to identify transformants, one may desire to employ a selectable or screenable marker gene as, or in addition to, the expressible preselected DNA sequence. In this case, one would then generally assay the potentially transformed cell population by exposing the cells to a selective agent or agents, or one would screen the cells for the desired marker gene trait.

A. Selection

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0–28 days on nonselective medium and subsequently transferred to medium containing from about 1–3 mg/l bialaphos or about 1–3 mM glyphosate, as appropriate. While ranges of about 1–3 mg/l bialaphos or about 1–3 mM glyphosate will typically be preferred, it is proposed that ranges of at least about 0.1–50 mg/l bialaphos or at least about 0.1–50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays L.* was selected with sub-lethal levels of bialaphos. Slowly growing tissue was subsequently screened for expression of the luciferase gene and transformants were identified. In this example, neither selection nor screening conditions employed were sufficient in and of themselves to identify transformants. Therefore it is proposed that combinations of selection and screening will enable one to identify transformants in a wider variety of cell and tissue types.

B. Regeneration and Seed Production

Cells that survive the exposure to the selective agent, or cells that have been scored positive in a screening assay, may be cultured in media that supports regeneration of plants. In an exemplary embodiment, MS and N6 media have been modified (see Table 1 of U.S. application Ser. No. 08/594,861, the disclosure of which is incorporated by reference herein) by including further substances such as growth regulators. A preferred growth regulator for such purposes is dicamba or 2,4-D. However, other growth regulators may be employed, including NAA, NAA+2,4-D or perhaps even picloram. Media improvement in these and like ways was found to facilitate the growth of cells at specific developmental stages. Tissue is preferably maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are transferred every two weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber at about 85% relative humidity, about 600 ppm $CO_2$, and at about 25–250 microeinsteins $m^{-2} \cdot s^{-1}$ of light. Plants are preferably matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con®s. Regenerating plants are preferably grown at about 19° to 28° C. After the regenerating plants have reached the stage of shoot and root development, they may be transferred to a greenhouse for further growth and testing.

Mature plants are then obtained from cell lines that are known to express the trait. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred maize plants in order to introgress the preselected DNA sequence into the genome of the inbred maize plants. This process is referred to as backcross conversion. When a sufficient number of crosses to the recurrent inbred parent have been completed in order to produce a product of the backcross conversion process that is substantially isogenic with the recurrent inbred parent except for the presence of the introduced preselected DNA sequence, the plant is self-pollinated at least once in order to produce a homozygous backcross converted inbred containing the preselected DNA sequence. Progeny of these plants are true breeding and the weight percentage of a particular amino acid in a plant part, e.g., the seeds, or the amount of starch in these progeny are compared to the weight percentage of that amino acid or amount of starch in the recurrent parent inbred, in the field under a range of environmental conditions (see below). The determination of the weight percentage of an amino acid or amount of starch are well known in the art.

Alternatively, seed from transformed monocot plants regenerated from transformed tissue cultures is grown in the field and self-pollinated to generate true breeding plants.

Seed from the fertile transgenic plants is then evaluated for the presence and/or expression of the sense or antisense DNA sequence. Transgenic seed tissue can be analyzed for a substantial inhibition in the production of the seed storage protein using standard methods such as SDS polyacrylamide gel electrophoresis. A substantial inhibition of the production of the seed storage protein is a decrease in the weight percent of the seed storage protein, preferably of about 70–100% and more preferably about 80–100% over that normally present in a nontransformed seed. The weight percent of a seed storage protein or an amino acid is based upon the amount of that protein or amino acid present per total weight of all proteins or amino acids in the seed. The seed can also be evaluated for an increase in the weight percent of at least one amino acid essential in the diet of animals by standard methods. An increase in the weight percent of the target amino acid is preferably about 50–300%, and more preferably about 100–200%, over that normally present in the untransformed seed. While not in any way meant to limit the invention, the decrease in the expression in the target seed storage protein is generally accompanied by an increase in other proteins having amino acids essential in the diet of animals.

Once a transgenic seed expressing the sense or antisense DNA sequence and having an increase in the weight percent of the amino acid essential in the diet of animals is identified, the seed can be used to develop true breeding plants. The true breeding plants are used to develop a line of plants with an increase in the weight percent of an amino acid essential in the diet of animals as a dominant trait while still maintaining other desirable functional agronomic traits. Adding the trait of increasing the weight percent of an amino acid essential in the diet of animals to agronomically elite lines can be accomplished by back-crossing with this trait and with those without the trait and studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not expressing the trait of an increased weight percent of the target amino acid. The resulting progeny are then crossed back to the parent not expressing the trait. The progeny from this cross will also segregate so that some of the progeny carry the trait and some do not. This back-crossing is repeated until the inbred line with the desirable functional agronomic traits, but without the trait of an increase in the weight percent of an amino acid essential in the diet of animals, which is expressed in a dominant fashion.

Subsequent to back-crossing, the new transgenic plants are evaluated for an increase in the weight percent of an amino acid essential in the diet of animals as well as for a battery of functional agronomic characteristics. These other functional agronomic characteristics include kernel hardness, yield, resistance to disease and insect pests, drought resistance, and herbicide resistance.

Plants that may be improved by these methods include but are not limited to processed plants (canola, potatoes, tomatoes, lupins, sunflower and cottonseed), forage plants (alfalfa, clover and fescue), and the grains (maize, wheat, barley, oats, rice, sorghum, millet and rye). The plants or plant parts may be used directly as feed or food or the amino acid(s) may be extracted for use as a feed or food additive.

C. Determination of Stably Transformed Plant Tissues

To confirm the presence of the preselected DNA sequence in the regenerating plants, or seeds or progeny derived from the regenerated plant, a variety of assays may be performed. Such assays include, for example, "molecular biological" assays well known to those of skill in the art, such as Southern and Northern blotting and PCR; "biochemical" assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA sequences or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

IV. Increasing the Weight Percent of at Least One Amino Acid Essential to the Diet of Animals.

The present invention is directed to increasing the amount of an amino acid essential to the diet of animals in a transgenic plant or seed over that normally present in the corresponding nontransformed (nontransgenic) plant or its seed. Plant cells are stably transformed with a preselected DNA sequence that encodes a RNA molecule having substantial identity (sense), or complementarity (antisense), to a mRNA coding for a seed storage protein, preferably a seed storage protein which is deficient in at least one amino acid essential in the diet of animals. The transformed cells are used to regenerate fertile transgenic plants and seeds. The antisense, or sense, RNA sequence is expressed in the seeds in an amount effective to inhibit the production of the seed storage protein. The decrease in the seed storage protein deficient in the essential amino acid results in an increase in the weight percent of other amino acids, preferably essential amino acids, present in other proteins in the transgenic seed over that normally present in the nontransformed seed.

In a preferred embodiment, a maize cell line is transformed with an expression vector comprising a preselected DNA sequence coding for a RNA molecule substantially identical, or complementary, to all or a portion of a mRNA coding for a 19 kD or 22 kD α-zein protein operably linked to a promoter for a 10 kD zein protein. Another preferred embodiment includes linking the preselected DNA sequence to the Z27 promoter. The expression vector preferably further comprises at least one selectable marker gene. The maize cell line is transformed by biolistic transformation and transformants are initially selected by growth in the presence of an agent which is present at levels which inhibit the growth of the corresponding nontransformed cells. Transformants are further characterized for the presence or expression of the preselected DNA sequence by polymerase chain reaction (PCR) or reverse transcriptase (RT-PCR) analysis. Transformed maize cell lines having the preselected DNA sequence are used to regenerate fertile transgenic plants by the method as described in PCT publication WO 95/06128. The fertile transgenic plants are self-pollinated or crossed to a second plant variety, and the transgenic seeds are characterized for the inhibition of production of a 19 kD or 22 kD α-zein protein by quantitative Western blot, or SDS-PAGE, and for an increase in the weight percent of an amino acid essential to the diet of animals, such as lysine.

In an alternative embodiment, the present invention is directed to increasing the weight percent of an amino acid essential in the diet of animals in a plant or seed by stably transforming the cells of a plant tissue source with at least two different preselected DNA sequences. The first preselected DNA sequence comprises a preselected DNA sequence coding a RNA molecule substantially identical, or complementary, to a mRNA for a seed storage protein, preferably a seed storage protein which is deficient in at least one amino acid essential to the diet of animals. The second preselected DNA sequence encodes a polypeptide comprising at least one amino acid essential to the diet of animals. The expression cassettes comprising one or both of the preselected DNA sequences can optionally comprise a selectable marker gene and, optionally, a reporter gene. Each preselected DNA sequence may comprise a different selectable marker gene so that transformants containing both preselected DNA sequences can be readily selected.

The cells of plant tissue source, as well as the methods of transformation described previously, can be employed in co-transformation. Co-transformation can be conducted sequentially, that is, the cells of plant tissue source can be transformed with the first preselected DNA sequence and transformants selected. The transformants can then be transformed with the second preselected DNA sequence and transformants having both preselected DNA sequences can be selected. Typically, the initial selection is based upon the trait expressed by the selectable marker gene or genes. Co-transformation can also be conducted in one step, that is, the cells of the plant tissue source can be transformed with both preselected DNA sequences at once, e.g., by electroporation or biolistic transformation. Alternatively, two plants can be crossed. The genome of one of the plants comprises the first preselected DNA sequence and the genome of the other plant in the cross comprises the second preselected DNA sequence.

Transfornants containing both preselected DNA sequences are further characterized for the presence and/or expression of the first preselected DNA sequence and the second preselected DNA sequence by standard methods, such as PCR or RT-PCR, Southern blot hybridization, SDS-PAGE and quantitative Western blot. Transformants having both introduced sequences are used to generate fertile transgenic plants and seeds therefrom as described previously.

The transgenic seeds are then characterized for the presence and/or expression of both preselected DNA sequences. Expression of the first preselected DNA sequence can be detected and quantitated by examining the seeds for a substantial inhibition of the production of a seed storage protein deficient in an amino acid essential in the diet of animals. Expression of the second preselected DNA sequence can be detected and quantitated by quantitative Western blot for the plant protein comprising at least one amino acid essential in the diet of animals and/or by an increase in the weight percent of an amino acid essential in the diet of animals, such as lysine or methionine, as compared to an untransformed seed.

In a preferred embodiment, a maize cell line is co-transformed with a first preselected DNA sequence coding for a RNA molecule substantially identical, or complementary, to all or a portion of a mRNA coding for a 19 kD or 22 kD α-zein protein, and a second preselected DNA sequence coding for a 10 kD zein protein. The 19 kD or 22 kD α-zein protein is preferably deficient in at least one amino acid essential in the diet of animals, such as lysine, methionine or tryptophan. The 10 kD zein protein preferably comprises at least one amino acid essential in the diet of animals, such as methionine. The isolated, purified DNA molecule comprising the first preselected DNA sequence also preferably comprises a selectable marker gene or a reporter gene, such as GUS. The second preselected DNA sequence may contain a second selectable marker gene, such as glyphosate resistant EPSPS.

In a further embodiment of the present invention, maize is cotransformed with a first preselected sense DNA sequence coding for a RNA molecule which is identical, or complementary, to the 19 kD or 22 kD α-zein mRNA and a second preselected DNA sequence encoding the synthetic protein MB1. Alternatively, the second preselected DNA sequence encodes a 27 kD zein protein. Thus, it is contemplated that genes encoding other synthetic or naturally occurring proteins comprising at least one amino acid essential in the diet of animals may be substituted for MB1. Even more preferably, maize is cotransformed with a first preselected sense DNA sequence coding for a RNA molecule which is identical, or complementary, to the 19 kD or 22 kD α-zein mRNA, a second preselected DNA sequence encoding the synthetic protein MB1, and a third preselected DNA sequence encoding a 27 kD zein protein.

Transformants having both preselected DNA sequences are used to generate fertile transgenic plants and seeds. The transgenic seeds are characterized by a substantial inhibition of the production of a 19 kD or 22 kD α-zein protein, determined, for example, by quantitative Western blot, and by an increase in the weight percent of an amino acid essential in the diet of animals, such as methionine or lysine. The transgenic seeds and plants can be used to develop true breeding plants so that the trait of an increase of the weight percent of an amino acid essential in the diet of animals can be expressed as a dominant trait while still maintaining functional agronomic qualities, as described hereinabove.

V. Method to Increase Starch Content of a Plant Seed

The invention also provides for an increase in the weight percent of starch in a plant and/or seed. The method comprises stably transforming the cells of a plant tissue with a first preselected DNA sequence coding for an RNA molecule substantially homologous or complementary to all or a portion of a mRNA coding for at least one seed storage protein. While not in any way meant to limit the invention, it is believed that a decrease in the expression of seed storage protein in the seed results in an increase in the weight percent of the starch in the seed. The preselected DNA sequence is preferably operably linked to a promoter functional in a plant and/or seed. Transformed cells are used to regenerate fertile transgenic plants and/or seeds. The transgenic seeds are characterized for expression of the preselected DNA sequence by examining the seed for a substantial inhibition of the production of at least one seed storage protein and for an increase in the weight percent of starch over that normally present in an untransformed seed.

The first preselected DNA sequence can be derived from a DNA sequence encoding at least one plant seed storage protein. Plant seed storage proteins include the zein proteins of maize such as the α-, β-, γ-, or δ-zein proteins. While not in any way meant to limit the invention, it is believed that a decrease in the expression of seed storage protein in the seed results in an increase in the weight percent of the starch in the seed. Preferably, the presence of the first preselected DNA sequence results in a substantial inhibition of at least one seed storage protein, and more preferably results in the inhibition of the α-zein proteins. The preparation of said first DNA sequence as well as its linkage to suitable promoters can be accomplished as described hereinabove. Cells of plant tissue can be transformed as described above, and transformants selected. Transformants are used to generate fertile transgenic plants and seeds.

Transgenic seeds are characterized by an increase in the weight percent of starch in the seed over that present in the untransfonmed seed. The weight percent of the starch content in the seed can be determined by enzymatic hydrolysis and glucose determination. The weight percent of starch is calculated by comparing the weight of the starch in the seed compared to the total weight of the seed. An increase in the weight percent of the starch in the transgenic seed is preferably about 1 to 10%, and more preferably about 3 to 8%, and even more preferably about 5 to 7%, over that in the non-transformed seed.

Transgenic seeds with an increase in the weight percent of starch can be used to develop true breeding plants expressing this trait in a dominant fashion while still maintaining functional agronomic traits as described previously.

Reduction of α-zein levels in corn kernels may also increase the degree of starch recovery from operations such as wet-milling of grain as α-zeins constitute the major portion of the proteinaceous matrix which surrounds starch granules in the kernel (Lopes and Larkins, 1993). A reduction in the amount of these hydrophobic proteins could facilitate recovery of starch grains. This is of particular significance for specialty starches, such as that obtained from high-amylose corn or waxy corn, because those starches are of much higher value than that obtained from No. 2 yellow dent corn. An increase in starch yield, i.e., the percent of starch present in the kernel which may be recovered by wet milling, is preferably about 1% to 20%, more preferably about 3% to 15%, and even more preferably about 6% to 12%, greater in grain from plants containing the preselected DNA sequence over grain from plants which do not contain the preselected DNA sequence.

VI. A Method for Inhibiting the Expression of a Family or Subfamily of Seed Storage Proteins.

The invention also provides a method for inhibiting the expression of a family, or subfamily, of seed storage proteins. Seed storage proteins such as the maize zein proteins are encoded by multi-gene families. The multi-gene families corresponding to zein proteins have different molecular weights: α-zein proteins include proteins with molecular weights of 19 kD and 22 kD; β-zein proteins include proteins with a molecular weight of 14 kD; γ-zein proteins include proteins with molecular weights of about 27 kD and 16 kD; and δ-zein proteins include proteins with molecular weights of about 10 kD. Each family can have several subfamilies. For example, the subfamilies for α-zein proteins are determined on the basis of sequence homology to cDNA clones A20, A30, B49, B59, or B36 as described by Messing et al., cited supra., or the Z4 cDNA clone encoding the 22 kD α-zein. Typically, members of the same subfamily share about 90% to 100% amino acid sequence homology and members of different subfamilies share about 60% to 80% amino acid sequence homology.

The examination of the amino acid sequence for the α-zein subfamilies has identified four functional subdomains and regions of shared amino acid homology in these functional subdomains as shown in FIG. 1. These regions of amino acid sequence homology can be used to analyze amino acid sequences from other subfamilies and families of zein proteins for homology. In addition, these regions can be used to select DNA sequences that encode a RNA molecule that can inhibit production of a family or a subfamily of the zein proteins. An antisense RNA sequence than can inhibit production of a family or subfamily of zein proteins is preferably a sequence that is substantially complementary to a portion of a mRNA sequence that is substantially homologous between all members of the subfamily or family of the zein proteins. Alternatively, it is contemplated that preselected sense DNA sequences may be used to suppress the synthesis of a family or a subfamily of zein.

For example, as shown in FIG. 1, the A20, A30, and B49 subfamilies share amino acid sequence homology in the signal peptide region and amino terminal region of the proteins. An antisense DNA sequence encoding these regions of the zein protein can encode a RNA molecule that can inhibit expression for a family of zein proteins. The antisense DNA sequence encoding these regions can be selected based on the amino acid sequence homology in these regions and can be used to inhibit expression of more than one subfamily of a family of the zein proteins.

The domain containing the tandem repeats of 20 amino acids has the greatest variability in amino acid sequence and size. There are insertions and deletions in this region when the sequence of different subfamilies are compared. A preselected antisense DNA sequence encoding this region of the α-zein protein can be employed to express a RNA molecule that can inhibit the expression of a subfamily of zein proteins. The preselected antisense DNA sequence from this region of the zein protein is substantially homologous within a subfamily but is not substantially homologous between subfamilies.

The preselected antisense DNA sequence is obtained by restriction endonuclease digestion of a cDNA or genomic clone coding for a seed storage protein. The preselected antisense DNA sequence is linked to a promoter to form an antisense expression cassette to determine the capacity of the antisense DNA sequence to inhibit translation of a family or subfamily of seed storage proteins. A standard assay such as hybrid arrested translation may be employed. The preselected antisense DNA sequence results in substantial inhibition of translation of cDNA clones from several families such as A20, Z4, A30, and/or B49. The preselected antisense DNA sequence can inhibit a family of zein proteins. The preselected antisense DNA sequence substantially inhibits translation of cDNA clones or genomic clones within a subfamily and the preselected antisense DNA sequence can be used to inhibit expression of a subfamily of zein proteins. The preselected antisense DNA sequence is used to stably transform plant cells as described hereinabove. Sense DNA sequences may also be used. Fertile transgenic plants and seeds are generated from the transformed cells.

The transgenic seeds are characterized for expression of the preselected antisense DNA sequence by evaluating inhibition of production of two or more members of a family or subfamily of zein proteins by using techniques such as quantitative Western blot.

In a preferred embodiment, the preferred antisense DNA sequence coding for a RNA molecule substantially complementary to a mRNA coding for the tandem repeat region of domain 3 of an α-zein protein in A20 subfamily is combined with a Z10 promoter. The expression cassette comprising the preselected antisense DNA sequence can also comprise one or more selectable marker genes. The preselected antisense DNA sequence is stably transformed into a maize cell line and transformants are selected. Transformed cells are used to generate fertile transgenic plants and seeds. The transgenic seeds are evaluated for expression of the preselected antisense DNA sequence by confining substantial inhibition in the production of the A20 subfamily of α-zein proteins by quantitative Western blot.

VII. Method for Increasing the Production of a Preselected Polypeptide in Seeds

The invention further provides for an increase in the expression of a particular polypeptide in plants and/or seeds. The method involves stably transforming cells with a first preselected DNA sequence to suppress synthesis of a seed storage protein deficient in an essential amino acid and a second preselected DNA sequence coding for a polypeptide, such as an enzyme or a seed storage protein. While not in any way meant to limit the invention, it is believed that a substantial inhibition of production of at least one seed storage protein is accompanied by an increase in the capacity of the plant cell and/or seed to produce other proteins. Transformed cells having both first and second preselected DNA sequences are obtained and used to generate fertile transgenic plants and/or seeds.

The first preselected DNA sequence encodes an antisense or sense RNA for at least one seed storage protein. The first preselected DNA sequence is combined with a promoter functional in plant and/or seed to form an expression cassette. Optionally and preferably, the expression cassette also comprises a selectable marker gene and, optionally, a reporter gene.

The second preselected DNA sequence, which encodes a polypeptide, is operably linked to a promoter functional in plant and/or seed. Preferably, the promoter is functional during plant and seed development. The second preselected DNA sequence encodes a polypeptide that provides the plant or seed with a desirable functional characteristic, such as increased disease or pest resistance, drought resistance, increased amino acid biosynthesis, increased nutritional value, increased kernel hardness, and the like.

The preselected DNA sequences can be operably linked to the promoter by standard methods provided in Sambrook et al., cited supra., and as described previously. Optionally and preferably, the expression cassette which comprises the second preselected DNA sequence also comprises a selectable marker gene different from the selectable marker gene present in the expression cassette comprising the first preselected DNA sequence.

Transformation of plant cells is conducted by any one of the methods described previously. The plant cells can be transformed with the first and/or second preselected DNA sequences sequentially or simultaneously. When the plant cells are sequentially transformed, transformants comprising the first preselected sequence are obtained based upon the presence of a selectable marker gene. These transformed cells are then transformed with the second preselected DNA sequence and transformants are obtained based upon the presence of each of the selectable marker genes present on the expression cassette comprising the first preselected DNA sequence and present on the expression cassette comprising the second preselected DNA sequence. Transformants containing both the first and second preselected DNA sequences are used to regenerate fertile transgenic plants and/or seeds.

The transgenic seeds are characterized by expression of the first and second preselected DNA sequences. Expression of the first preselected DNA sequence is evaluated by measuring a substantial inhibition in the production of at least one seed storage protein. Expression of the second preselected DNA sequence is evaluated by detecting the preselected polypeptide using standard phenotypic or genotypic methods, such as quantitative Western blot. An increase in the expression of a polypeptide can be determined by comparing the weight percent of the protein produced in plants or seeds transformed with the second preselected DNA sequence. The expression of the polypeptide is preferably increased about 2- to 100-fold, and more preferably about 5- to 30-fold, over that in a plant and/or seed only transformed with the second preselected DNA sequence.

The invention will be further described by the following examples.

EXAMPLE 1

Construction of Plasmid Containing Antisense DNA Constructs

Antisense expression cassettes were obtained by using sequences from cDNA clones encoding zein proteins. The cDNA clones were prepared by standard methods, described previously by Geraghty et al. (1982) and Hu et al. (1982), which are hereby incorporated by reference. The cDNA clone A20 encodes an α-zein protein of the 19 kD size class of the Z1A subfamily of zein genes. Another cDNA clone designated Z4 encodes an α-zein of the 22 kD size class of the Z1B family of genes. The Z1A and Z1B subfamilies and their characteristics are shown in Table I.

subfamilies as it contains 9–10 tandem repeats of sequence encoding a 20 amino acid sequence. The number of repeats present in Domain III determines the size of the α-zein protein (19 kD or 22 kD). Typically, individual members within a subfamily share 90–100% sequence homology and while the sequence homology between subfamilies ranges from about 65–85%.

All antisense plasmids for in vitro system analysis were constructed by standard recombinant techniques as detailed below, using the transcriptional vectors pSP72 and pSP73 (Promega, Madison, Wis.). These transcription vectors are 2.46 kb circular plasmids, containing 103 bp of polylinker sequence inserted between convergent T7 and SP6 transcriptional promoters. The two transcription vectors differ in the orientation of the polylinker with respect to the promoters. Antisense plasmids, complementary to all or portions of the cDNA clones A20 and Z4, were constructed as described below.

The RNA sequence for A20 (SEQ ID NO:1) and the DNA sequence for Z4 (SEQ ID NO:2) zein are shown in FIGS. 2 and 3, respectively. The relevant A20 and Z4 genes and gene fragments used in antisense constructs are shown in Table II.

TABLE II

| Antisense Construct Designation | Restriction Enzymes | Insert Size |
|---|---|---|
| SP20 ent | BalI/EcoRI | 711 |
| SP20R3' | BalI/PstI | 488 |
| SP20R | PstI/PstI | 262 |
| SP20P | BalI/EcoRI | 863 |
| SP20P5' | AccI/EcoRI | 458 |

TABLE I

Prolamin Fraction of Maize (Alcohol Soluble) Zein Multigene Family

| | z1 (non-reducing conditions) | | | | z2 (reducing conditions) | | |
|---|---|---|---|---|---|---|---|
| Subfamily | z1A | z1B | z1C | z1D | z2A (ASC) | z2B | z2C |
| Representing cDNA clone | A20 | A30 | B49 | B59 | B36 | Z15A | — |
| Mr × 100 | mostly 19 | mostly 19 some 22 | mostly 22 some 19 | mostly 19 | 27 | 15 | 10 |
| Locus | 4L, 7S, 10L | 4L, 7S | 4L | ? | ? | ? | ? |
| Predominant amino acid | glutamine | glutamine | glutamine | glutamine | proline | cysteine | methionine |
| Timing of expression | ca 12 dap | ca 12 dap | ca 18 dap | ca 12 dap | ca 18 dap | ca 18 dap | ca 18 dap |
| Transaction mutants (o6+++.f12+.Mc+) | o2+.o7+++ De*-B30+ | o2+.o7++ De*-B30+ | o2+++.o7++ De*-B30+++ | o2+.o7++ De*-B30+ | o2+.o7+ De*-B30+ | o2+.o7++ De*-B30+ | o2++.o7++ De*-B30+ |
| No. of genes | <25 | <20 | <15 | <5 | 2 | 2 | ? |

+reduced synthesis
++increasingly reduced synthesis
+++strongly reduced synthesis Antisense expression cassettes comprising the complete cDNA sequence for clones A20 and Z4, as well as portions of those sequences, were generated. The portions of each sequence were selected by examining the sequence of the 19 kD and 22 kD α-zein proteins. As shown in FIG. 1, the primary sequence of the polypeptides can be divided into four domains, as described by Messing et al. (1983). Domain I contains the highly conserved 21 amino acid signal peptide that is cleaved during cotranslational transport of zein proteins into the lumen of the endoplasmic reticulum. Domains II and IV are the N-terminal and C-terninal regions, respectively, of the mature zein proteins. Domain III represents the major source of sequence homology between TABLE II-continued

| Antisense Construct Designation | Restriction Enzymes | Insert Size |
|---|---|---|
| SPZ4ent | SacI/BamHI | 960 |
| SPZ4R3' | XbaI/BamHI | 713 |
| SPZ4R5' | BamHI/DdeI | 246 |
| SPZ10ent | EcoRI | 640 |

All restriction and modification enzymes and buffers were obtained from New England Biolabs, Inc. (Beverly, Mass.), unless otherwise noted, and used according to the manufacturer's specifications. All insert fragments were gel isolated and purified by the Geneclean method (BIO 101, Vista, Calif.), and all vectors were treated with calf intestinal phosphatase (Boehringer-Mannheim Corporation, Indianapolis, Ind.), then gel isolated on low melting point agarose before addition to the ligation reactions.

Antisense constructs encoding all or a portion of the cDNA clones from A20 and Z4 were prepared as follows:
SP20ENT: The parent plasmid pUC12/A20, containing the entire mature coding and 3' nontranslated sequence (nts) from the A20 cDNA clone (the RNA sequence of A20 is shown in FIG. 2), was digested at the EcoRI site (nt 175) and the BalI site (nt 886) to generate a 711 nt fragment containing the entire sequence except for 55 bp of 3' nts. The fragment was ligated into pSP72 which had been digested with EcoRI and PvuII, resulting in 3' to 5' antisense orientation of the gene with respect to the SP6 promoter.
SP20R3': A 488 bp fragment, containing the sequence encoding the mid-repeat region through the 3' nts A20 from the Pst 1 site at nt 298 to the Ball site at nt 886, was isolated from the parent plasmid p1020R3' prepared as in Example 2. The fragment was obtained by digesting p1020R3' with KpnI and HindIll, and after isolation the fragment was ligated into pSP72 that had been digested with these enzymes also. The gene fragment was therefore oriented 5' to 3 ' with respect to the SP6 promoter.
SP20R: A 262 bp fragment, from nt 398 to nt 660 was obtained by digesting pUC12/A20 with PstI. The purified fragment was ligated into pSP72 digested with PstI to make pSP20R, containing the sequence encoding the mid-repeat region of A20 in the 3' to 5' orientation with respect to the SP6 promoter.
SP20P: The 5' end of the A20 transcription unit was reconstructed by PCR amplification of a fragment containing 5' nts and encoding the signal peptide through the mid-repeat region, since the 5' nts and signal peptide sequence was not contained in the pUC12/A20 clone. The primers used in the amplification are designated A20P5'.2 (SEQ ID NO:3) and A20P3' (SEQ ID NO:4). The fragment was amplified from genomic DNA isolated from leaf tissue from the maize inbred line A654, and contained 458 bp of A20 cDNA sequence, from nt 58 to nt 490.

The conditions for PCR are detailed below; all reactions were carried out in a Biosycler™ oven (Bios Corporation). Each reaction contained 10 µl of 10× PCR reaction buffer, 10 µl of 20 mM $MgCl_2$, 10 µl of 2 mM dNTPs, 10 µl of each primer (stock 2.5 ml) and 0.5 µl (2.5 U) of Taq polymerase (Perkin-Elmer Cetus), for a total of 100.5 µl/reaction. An annealing temperature of 56° C. was used, and a total of 30 cycles were performed, including the first three cycles with extended incubation at the 94° C. denaturing temperature. Parameters for the first three amplification cycles were as follows: 60 seconds at 94° C., 30 seconds at the annealing temperature of 56° C., and 30 seconds at the synthesis temperature of 72° C. For the remaining 27 cycles, the parameters were as follows: after bringing the reactions to 94° C., 15 seconds at this temperature, then 15 seconds at 56° C., followed by 15 seconds at 72° C.

The 458 bp product was designed to add a 5' EcoR1 site, and included an endogenous 3' AccI site. After digestion with these enzymes, the amplified fragment was ligated into pSP20ENT also digested with these enzymes, replacing a 320 bp fragment containing the shorter 5' end fragment of A20 from pSP20ENT. After reconstruction, the gene was approximately 860 bp long, and contained approximately 55 nt of 5' nts, the sequence encoding the signal peptide, and the entire coding sequence as well as 3' nts. The reconstructed gene is oriented 3' to 5' with respect to the SP6 promoter.
SP20P5': The 5' end of the A20 gene, after PCR amplification and digestion with EcoRI and AccI as described above, was cloned into pSP72 to generate pSP20P5'. This construct contains 458 nt of A20 sequence, including 55 nt of 5' nontranslated sequence and 403 nt of coding sequence, which includes approximately the N terminal half of the coding sequence. The inserted sequence is oriented from 3' to 5' with respect to the SP6 promoter.
SPZ4ENT: Essentially, the entire Z4 transcription unit is contained in this clone, with a total insert size of 960 nt. The gene was reconstructed from two Z4 subclones, pSPZ4R3' and pSPZ45', which are described below. The parent vector was pSPZ4R3', containing 713 nt of mid-repeat to 3' nts sequence, from nt 630 to nt 1341 of the Z4 sequence (the DNA sequence of Z4 is shown in FIG. 3). The 5' end of the Z4 sequence was released by digestion with SacI (which cleaves the polylinker sequence outside the inserted gene) and BamHI, and the insert containing the 5' sequence from pSPZ45', obtained by SacI (which also cleaves the polylinker sequence) an dBamHI digestion, was ligated to the linearized pSPZ4R3', resulting in reconstitution of the intact Z4 transcription unit.
SPZ4R3': A 713 nt insert fragment, containing the mid-repeat region to the 3' noncoding sequence, was isolated after digestion with BamHI (nt 630) and XbaI (nt 1341). The fragment was ligated into pSP72 digested with the same enzymes, resulting in orientation of the gene fragment in 3' to 5' direction with respect to the SP6 promoter.
SPZ45': A 247 nt fragment containing 76 nt of 5' noncoding sequence, the signal peptide sequence, and approximately 100 nt of mature protein coding sequence was cloned into pSP72. After digestion with DdeI, the DNA was Klenow treated to create blunt ends, then digested with BamHI to release the desired fragment. The fragment was ligated into pSP72 digested with EcoRV and BamHI, resulting in 3' to 5' orientation of the gene fragment with respect to the SP6 promoter.
SPZ10ENT: A 670 nt fragment containing the entire Z10 transcriptional unit was isolated from the 10 kD zein cDNA clone p10Z-1 by digestion with EcoRI (the sequence of the 10 kD zein gene can be found in Kirihara et al., 1988). After digestion of pSP72 with EcoRI also, the insert was ligated with the vector to produce pSPZ10ENT, a circular plasmid of 3.16 kb. Clones were obtained containing both orientations, and the clone used in the hybrid arrest studies contained the 10 kD transcription unit oriented 3' to 5' with respect to the SP6 promoter.

EXAMPLE 2

Construction of Plasmids Containing an Antisense DNA Sequence for Use in Maize Transformation A set of antisense plasmids was constructed for expression in maize, using entire or portions of the Z4 and A20 sequence as detailed in Example 1, above. The antisense constructs were combined with a promoter functional in plant endosperm tissue to form a DNA sequence that can be expressed in a plant seed.

Vector Construction

The plasmids p10B and p10X were constructed from pZ10nos3'. The construct pZ10nos3' contains 1137 bp of the Z10 promoter from a gene encoding a 10 kD zein promoter upstream of a short polylinker, which is adjacent to the nos poly A 3' element. The vectors p10X and p10B were created by digestion of pZ10nos3' with BamHI, Klenow treatment to blunt the BamHI site, then ligation with a polylinker insert, resulting in clones containing both orientations of the polylinker with respect to the Z10 promoter. The polylinker fragment was obtained by digesting pSP73 with BglIII and XhoI, followed by Klenow treatment then ligation with the prepared pZ10nos3' vector. The p10X version contains the polylinker oriented with the XhoI site proximal to the Z10 promoter, while the p10B version contains the polylinker oriented with the BglIII site proximal to the Z10 promoter. Both plasmids are circular plasmids of approximately 4.65 kb. Antisense DNA expression constructs, prepared as described in Example I were combined with a promoter functional in a plant seed utilizing the p10B and p10X plasmids, as described below.

1020ENT: A 725 nt insert fragment containing the mature A20 coding and 3' noncoding sequence (see Example 1, SP20ENT section), and including some polylinker sequence, was obtained by digestion of SP20ENT with ClaI (cuts in the polylinker sequence) and XhoI. The vector, p10X, was prepared by digestion with ClaI and XhoI also, then the insert and vector were ligated, generating p1020ENT, which contains the A20 sequence inserted 3' to 5' with respect to the Z10 promoter.

1020R3': A 488 nt insert fragment, containing the mid-repeat to the 3' noncoding sequence of A20, was isolated from the clone pUC12/A20. The insert contains sequence from the PstI site at nt 398 and continues to the BalI site at nt 886. The insert was obtained by digestion of pUC12/A20 with Hind III which cuts outside the A20 sequence, then partial digestion with PstI (digestion only at the nt 398 PstI site), followed by gel isolation of the desired fragment of 740 nt. After purification, the HindIII/PstI fragment was digested with BalI, which removed approximately 252 nt from the 3' end to generate a 488 nt fragment with PstI/BalI ends. This fragment was ligated into p10B which had been cut with SmaI and PstI, resulting in insertion of the A20R3' fragment in the 3' to 5' orientation with respect to the Z10promoter.

1020R: A 262 nt insert fragment, containing the mid-repeat region from A20 (as in SP20R from Example 1), was obtained by digestion of pUC12/A20 with PstI. The vector p10X was also digested with PstI and, after ligation, clones were obtained with both orientations of the fragment with respect to the Z10 promoter. An asymmetrical AccI site within the insert was used to select clones containing the fragment in the desired antisense orientation.

pDPG380: The 863 nt insert fragment containing the reconstructed A20 gene (as described for pSP20P above) was obtained by digesting pSP20P with XhoI and BglII (both of which cut in the polylinker), then ligating the fragment into p10X that had been digested with XhoI and BamHI. This resulted in a 3' to 5' orientation of the reconstructed A20 gene with respect to the Z10 promoter.

pDPG340: A 875 nt fragment, containing the entire Z4 gene as described above for pSPZ4ENT, was obtained by digestion of pSPZ4ENT with HindIII, Klenow treatment, then digestion with SalI. These enzymes cut in the polylinker sequence outside the gene in pSPZ4ENT. The vector, p10X, was digested with NcoI, Klenow treated, then digested with XhoI before ligation with the insert fragment. The resulting clone contained the gene in 3' to 5' orientation with respect to the Z10 promoter.

10Z4R3': An insert of approximately 750 nt, consisting of the Z4 mid-repeat through the 3' noncoding (as described in Example 1 for pSPZ4R3') was obtained by digesting pSPZ4R3' with SacI and SalI, which cut in the polylinker sequence. The vector , p10X, was digested with SalI and XhoI, and since XhoI and SalI create compatible ends, this resulted in directional cloning of the Z4R insert in the 3' to 5' orientation with respect to the Z10 promoter.

10Z45': An intermediate vector 119Z45', containing the Z45' sequence insert (see SPZ45' construction, Example 1) was first constricted using the pUC119 backbone (Sambrook et al., 1989).

The final construct, 10Z45RN, was constructed by moving the Z45' insert from 119Z45' into the p10B vector. First, 119Z45' was digested with BamHI and PstI, releasing a 270 bp fragment. The vector, p10B, was prepared by digestion with BamHI and PstI, and then the vector and insert were ligated to produce p10Z45', containing the Z45' insert in the antisense orientation with respect to the Z10 promoter.

pDPG530 and pDPG531: pDRG530 and pDRG531 were made by cutting a fragment of approximately 960 bp from SPZ4Ent and filling in the ends. The vector was a Z27promoter::Nos 3' region construct in pBSK(-) which contained a unique NcoI site between the promoter and terminator. Both the vector and insert were blunt-ended and ligated. Clones were identified with the sense orientation of the Z4 DNA sequence (pDPG531) and the antisense orientation of the Z4 DNA sequence (pDPG530).

EXAMPLE 3

In Vitro Method for Screening Antisense Containing DNA Sequences

Once an expression cassette comprising a preselected antisense DNA construct and a promoter functional in a plant seed was prepared, as described in Example 2, the expression cassette was screened for the ability to arrest translation of the genes encoding the 19 kD (A20) and 22 kD (Z4) α-zein proteins. The expression cassettes comprising the antisense DNA sequences were screened by standard hybrid arrested translation, as described below.

Template production. All reagents for in vitro transcription were obtained from Promega (Madison, Wis.), using their SP6/T7 transcription protocol. Slight modifications were made to the Promega protocol. Plasmids were digested with appropriate enzymes in order to linearize the templates, preventing transcription beyond the end of the inserted gene. Templates were digested with XhoI for SP6 transcription, and with BglII for T7 transcription, unless otherwise noted.

Twenty micrograms of DNA were digested in a total volume of 100 µl. After analyzing aliquots for complete digestion, digests were extracted with phenol/chloroform and chloroform, then precipitated with 0.1 volumes 3M sodium acetate, 2.5 volumes ethanol. After washing with 70% ethanol, pellets were resuspended in 10 µl of sterile, RNase-free water.

Transcription reactions. After thawing all reagents at room temperature, master transcription mixes were prepared, excluding template DNA. This resulted in greater yield uniformity of the reactions. For each reaction, the following components were added to 5 µl of template DNA at 1 µg/µl in RNase-free water. 20 µl of 54 transcription buffer, 10 µl at 0.1 M DTT, 2.5 µl of recombinant RNasin (an RNAse inhibitor supplied at 40 U/µl ), 20 µl of 10 mM rNTP mix, 2.5 µl of SP6 or T7 (20 U/µl), and 45 µl of RNase-free water. Reactions were incubated at 37° C. for two hours before template removal. Templates were removed by digestion with RQ1 DNase (1 U/µl), 5.0 µl of enzyme was added to the transcription reactions, which were then incubated at 37° C. for 15 minutes before extraction and precipitation of the transcript. Extraction, precipitation and washes were performed as described above for template preparation.

Transcript yield was determined by absorbance readings at 260 nm, and intactness of the preparations was determined by gel analysis, either native or denaturing. Although native gels occasionally showed bands of anomalous mobility, generally transcript preparations exhibited a roughly linear relationship between the expected transcript size and their mobility on native gels.

Annealing of Transcripts for Hybrid Formation. Before translation, transcripts were allowed to anneal under controlled temperature and salt conditions, using constant molar ratios of sense to antisense transcript. Conditions for annealing were as follows: 10 mM Tris, pH 7.5, 100 mM NaCl, RNA(s), and RNase-free water to bring the total volume to 20 µl. The amount of RNA added was based on a 4:1 molar ratio of antisense to sense transcript, with 4 µg of sense transcript in each reaction, and a variable µg amount of antisense transcript added to maintain the 4:1 molar ratio.

Before annealing, all transcripts were heated to 65° C., then kept at 0° C. to reduce potential formation of intramolecular secondary structures which would reduce the efficiency of duplex formation. After annealing for 45 minutes at 45° C., the reaction was split in half, so that 10 µl of the reaction could be translated in vitro, and the remaining 10 µl was analyzed on 1.2% agarose gels to determine the extent of hybrid formation in each sample. Although some anomalies in mobility were seen that were probably due to intramolecular interaction, this method was generally useful for analyzing the extent of duplex formation between two transcripts, and correlated well with the hybrid translation results.

In Vitro Translation of Annealing Reactions and Analysis of Translation Products.

Translation of both Z4ENT and A20 ENT transcripts was performed using wheat germ lysate and rabbit reticulocyte lysate systems (Promega). Although both systems produced detectable protein when the products of translation were analyzed by SDS-PAGE and autoradiography, the rabbit reticulocyte system translated both the Z4ENT and A20ENT transcripts more efficiently than the wheat germ system.

Translation of the annealed samples was performed in vitro, using a nuclease-treated rabbit reticulocyte lysate system (Promega), and $^{35}$S methionine was used to label the translation products (Amersham). The reactions were performed essentially according to the Promega protocol with modifications as described below.

To analyze translation products, reactions were run on SDS-PAGE, using a 4% stacking gel and 15% separation gel, with 0.75 or 1.5 mm spacers. Gels were run on a Hoefer apparatus, at 35 mA with constant current, for 3 to 3.5 hours. Samples were prepared for electrophoresis by adding 10 µl of each reaction to 40 µl of 1× sample buffer, then boiling for 7 minutes before spinning for 30 seconds in a microfuge. After removal of the stacking gel, gels were incubated for 30 minutes with shaking in a solution of 1 M sodium salicylate to enhance detection of the radioisotope. Gels were then rinsed briefly in water and dried on a slab drying under vacuum, at 65° C. for 2 hours. The dried gels were exposed to film overnight, using intensifying screens (Lightning Plus, Dupont Cronex) at −70° C. After developing, the gels were scanned using an LKB 2202 Ultroscan laser densitometer, and the data was compiled and analyzed using the Maxima software for chromatographic analysis (Waters Co.).

The results of in vitro translation of linearized plasmids containing the complete copies of the Z4 and A20 genes in the sense orientation show that the in vitro translation systems could be used to monitor the effects of antisense constructs on translation of the zein genes. Both translation systems produced proteins of the expected 19 kD weight species corresponding to the mature A20 gene product. Interestingly, however, while the rabbit reticulocyte system translated the Z4ENT transcript into the 22 kD preprotein, the wheat lysate system processed the Z4 preprotein, removing the signal peptide to produce the mature zein, resulting in a protein of approximately the same size as the 19 kD. In both systems, translation of the A20ENT transcript was at least 2–5× more efficient than translation of the Z4ENT transcript, probably due to the lack of a signal peptide in the A20ENT protein or differences in accessibility of the start codon between the two transcripts, since the A20ENT transcript did not contain 5' noncoding sequence.

Capping of the Z4ENT and A20ENT transcripts was performed as a possible means of increasing translation efficiency, using both cotranscriptional and posttranscriptional procedures. No increase in translation efficiency was observed with either method.

Hybrid arrest translations were performed using Z4ENT sense transcripts and Z4ENT antisense transcripts to establish annealing and translation conditions. A titration experiment was performed to determine the ratio of antisense:sense transcripts needed to completely abolish Z4 synthesis. Amounts of antisense transcript were added to 1, 2, and 5-fold excess over the amount of sense transcript and allowed to anneal under controlled conditions. Results of this experiment are shown in Table III. Subsequent experiments, using a 4:1 ratio of antisense:sense in the annealing reactions, were found to eliminate Z4 synthesis also, and so this ratio was used for later experiments.

TABLE III

Effect of Increasing the Ratio of Antisense to Sense Transcript on Z4 Synthesis

| Transcripts | Ratio | % Reduction in Z4 Synthesis | |
| --- | --- | --- | --- |
| | | Range | Mean |
| Z4ENTs | na | na | na |
| Z4ENTas/Z4ENTs | 1:1 | 55–63 | 59 |
| Z4ENTas/Z4ENTs | 2:1 | 84–85 | 85 |
| Z4ENTas/Z4ENTs | 5:1 | 100 | 100 |

Experiments were also done to determine whether the radiation dose/film exposure plot was sufficiently linear to allow quantitation of protein using laser densitometer readings of the film. To test this, the amount of extract loaded per lane was varied over a 25-fold range. Results indicated that the dose/response plot was acceptable over a 10-fold range only. Densitometry of the autoradiograms indicated that an overnight exposure of gels to film produced a meaningful dose-response curve, but that longer exposures did not.

Having established a basic protocol using the complete, perfectly complementary Z4ENT sense and antisense transcripts, a series of experiments was initiated to compare these results with the effect of antisense transcripts made from constructs containing only a portion of the Z4 transcriptional unit, as well as with antisense transcripts made from constructs containing all or portions of the A20 transcriptional unit. Data was compiled from several hybrid arrest of translation experiments, all performed using a 4:1 molar ratio of antisense:sense transcript, and all incorporating the Z4ENT sense transcript with no antisense transcript added as a negative control (representing 100% synthesis of Z4, or 0% reduction in Z4 synthesis), and the Z4ENT transcript with the Z4ENT antisense transcript added as a positive control (representing 100% reduction in Z4 synthesis). A lambda transcript and a polylinker transcript were used as controls. The results are shown in Table IV.

The results are shown in Table IV.

TABLE IV

Hybrid Arrested Translation Compiled Densitometer Data for Reduction in Z4 Protein Synthesis

| Antisense Transcript | Mean Reduction (%) | Number of Experiments Performed |
|---|---|---|
| Z4ENT | 100 | 5 |
| Z45' | 80 | 3 |
| Z4R3' | 75 | 3 |
| A20ENT | 81 | 3 |
| A20R | 59 | 2 |
| Z10E | 42 | 2 |
| lambda transcript | 32 | 1 |
| polylinker transcript | 0 | 2 |

General conclusions about the results can be drawn by summing the entire data set to generate a single rough consensus for efficiency of the antisense transcripts in effecting shutdown of Z4 synthesis, which are as follows:

Z4ENT>Z45'>A20ENT>Z4R3'>A20R>>Z10ENT>lambda>polylinker

This data indicates that the entire complementary transcript, as expected, is most efficient at reducing translation, and that antisense transcripts annealing to the translation initiation sequence are generally more efficient than transcripts annealing to the downstream coding region.

EXAMPLE 4

Production of Reagent Antibodies for Analysis of Maize Transformants

In order to screen for effects of antisense gene expression on zein expression levels in transformed cell lines and plants, polyclonal antibodies reactive with both the targeted α-zeins and with total zeins were produced. Antigens were extracted and purified as described below before inoculation into rabbits and subsequent antiserum characterization.

A. Antigen purification

Total zeins were obtained by extraction of the maize inbred line BSSS53. In this procedure, 4 grams of dry kernels were ground to a fine powder in a Braun coffee mill, defatted by incubation with 15 ml/g of acetone, with stirring, for 90 minutes at room temperature. The defatted meal was then filtered through a Buchner funnel and allowed to dry. Two extractions with 10 ml/g of 0.5 M NaCl were then performed; the mixture was stirred at room temperature for 30 minutes before filtering as above. Finally, two extractions were performed on the meal with 10 ml/g each of 70% ethanol % BME, for 60 minutes each, at room temperature with stirring. The ethanol extracts, totaling 80 ml, were pooled and filtered through a 0.45 micron filter before reducing the volume in a rotary evaporator (Rotovapor R110, Buchi Corp.). Evaporation was performed at 65° C., and after approximately 45 minutes the volume was reduced to 20 ml of solution, which had a cloudy appearance. This solution was diluted to 40 ml with sterile deionized water before freezing and lyophilization. A dry weight of 329 mg was obtained, and a 1 mg sample was weighed out, resuspended in 1 ml of 70% ethanol, and protein content was quantitated by the Peterson assay (Peterson, 1979). The zeins were found to comprise 45% of the sample dry weight, and so approximately 140 mg of zein was obtained. Samples containing a range of 2.5 to 25 $\mu$g of protein were analyzed for purity and presence of the expected zein profile by SDS-PAGE and silver or Coomassie blue staining of the gels (Sambrook et al., 1989). The preparation displayed the expected protein profile, with the 27 kD, 19/22 kD, 16 kD, 15 kD, and 10 kD zeins all present in the expected proportions. This preparation was, therefore, used as the antigen in raising of polyclonal sera against total zeins.

The α-zeins (19/22 kD zeins) were extracted from the maize inbred line A654 seed as follows: 6 grams of dry kernels were ground and processed as above for total zeins, from which approximately 500 mg of lyophilized sample was obtained. After determining protein content, the zeins were found to comprise 80% of the dry weight of the sample. To purify the α-zeins from the rest of the zeins, the sample was subjected to preparative SDS-PAGE: 10 mg of sample was weighed out, resuspended in 500 $\mu$l of sample buffer/5% BME, then boiled for 10 minutes to eliminate aggregates before spinning for 30 seconds in the microfuge. Aliquots of 55 $\mu$l/lane were run on a 3 mm thick gel, with a 4% stacker and a 15% separation gel. Extra long plates (25 cm long by 14 cm wide) were used to improve resolution. After running at 50 mA constant current for 3 hours, the gel was run at 15 mA overnight. Proteins were visualized by staining with cold 0.25 M TCA for approximately 10 minutes. Bands in the 19/22 kD range were then excised and washed in SDS gel running buffer until the gel pieces appeared clear. This buffer was saved, gel pieces were transferred to 2000 m.w. cutoff dialysis tubing. An additional 25 mg of starting material was processed in this fashion also, and all gel slices were pooled before dialysis. The dialysis tubing was sealed with clips, and placed in a Biorad mini-sub gel apparatus with the clips oriented perpendicularly with respect to the direction of electrophoresis. SDS running buffer was added to the level of the tubing, and elution was performed at 10 mA overnight. The electrodes were reversed briefly, then the buffer inside the dialysis bag was pooled with the reserved buffer from the initial gel slice washes and dialyzed against 1 liter of deionized water, changing the water five times over several hours. The dialysate was lyophilized, the protein was quantitated, and then examined for purity by SDS-PAGE and silver staining. No contaminating protein species were visible, and so the purified antigen was used to inoculate rabbits for polyclonal antibody production. The total amount of purified α-zein obtained from this procedure was 10.9 mg, resulting in a yield of 31% for the procedure.

B. Antigen preparation and injection

A total of six New Zealand white rabbits were used for antibody production. Three were injected with purified α-zeins, and the remaining three were injected with purified total zeins as described below. Two of the six rabbits were treated using the traditional Freund's complete and incomplete adjuvant, and the remaining four were treated with a synthetic adjuvant, as described below.

Both α- and total zeins were weighed, resuspended, and heated to 65° C. to completely solubilize the zeins; 0.5 mg of purified α-zein or 1.0 mg of total zein was resuspended in 60 $\mu$l of 70% ethanol for each rabbit to be injected. Rabbits 1–3 received total zein as the antigen, and rabbits 4–6 received purified α-zein antigen. For rabbits 1 and 4 (designated 1F and 4F hereinafter), 440 $\mu$l of PBS/Tween (phosphate buffered saline/2% Tween 80, Sigma) was added to the zein solution, then 500 $\mu$l of Freund's complete adjuvant (Sigma) was added and the tubes were vortexed vigorously. The remaining four samples were made up as follows: to the 60 $\mu$l of purified or total zein solution, 50 $\mu$l of AVRIDINE (a synthetic adjuvant from Kodak) made up in 100% ethanol to 140 mg/ml, 760 $\mu$l of Intralipid 10% fat emulsion (Travenol), and 300 $\mu$l of PBS/Tween were added. After vortexing, the samples were sonicated in a cup sonicator for 2–30 second bursts (Ultrasonics, Inc.) to ensure complete emulsion before injection.

Samples were administered in 100 µl aliquots injected at multiple sites across the back of the animals. Boosts were administered every three weeks, following the procedure above for formulating injection mixes except that Freund's incomplete adjuvant replaced the complete adjuvant for rabbits 1F and 4F. A total of three boosts were administered, in addition to the primary injection. Small volume (less than 5 ml) bleeds were performed to obtain sera for monitoring antibody titer and specificity during the process. Specificity and titer of the antisera were analyzed by running total zeins on SDS-PAGE/Western blots, as described below. Once titers were found to be sufficient (reactive at a 1:1000 sera dilution), several consecutive large (50 ml) bleeds were performed.

C. Analysis of Antisera

To determine antisera immunoreactivity and titer, total zein was assayed by SDS-PAGE/Western, with antisera dilutions from 1:50 to 1:1000 tested. The basic procedure was as follows: 500 ng of total zein/lane was dissolved in 10 µl of sample buffer/2% BME, boiled 7.5 minutes, then loaded on a 15% minigel (Mini Protean II, BioRad) with molecular weight markers (BRL) in alternate lanes, and run at 200 V for 45 minutes. The stacking gel was removed, and the gel was equilibrated in transfer buffer (0.025 M TrisCl, 0.194 M glycine, 20% methanol) for 10 minutes before being overlaid with a prepared membrane (Millipore Immobilon-P). Preparation of the membrane was performed by rinsing with methanol, according to the manufacturer's recommendations, before equilibrating in transfer buffer. Proteins were transferred at 27 V for 40 minutes n a Genie electroblotter (idea Scientific). After transfer, membranes were rinsed and blocked in 3% BSA/PBS for one hour at 37° C. on a shaker platform. Membranes were divided into strips by cutting at lanes containing molecular weight markers, and incubated with 10 ml of test antisera of the appropriate dilution overnight at 4° C., as well as with control polyclonal antisera directed against total zein. After removal of the primary antisera, membrane strips were washed in 1×PBS, for 5×10 minute washes, before incubation with the secondary antibody. The secondary antibody consisted of goat-anti-rabbit alkaline phosphatase-conjugated antibody (Kirkegaard-Perry Laboratories), diluted 1:1000 in 3% BSA/PBS. After incubating for 1 hour at room temperature with shaking, strips were washed as above, and strips were incubated in 4-chloro-napthol substrate solution (KPL) until color development was complete, approximately 2–5 minutes. Reactions were stopped by rinsing the strips in deionized water.

The results showed that sera from all six rabbits displayed the expected immunoreactivity profiles. Specifically, sera from rabbits 1F, 2, and 3 immunolabelled only the 19/22 kD zeins, and not the other zeins (indicating that the quality of the gel purified antigen was at least as good as predicted by silver staining of SDS-PAGE, since antibody production would actually be a more sensitive measurement of contamination with other protein species). In addition, the sera from rabbits 4F, 5, and 6 exhibited reactivity with all of the zeins in approximate proportion to the relative amounts of protein present in the profile, showing slight to moderate labeling of the 27 kD zein, very strong labeling of the abundant 19/22 kD zeins, moderate labeling of the 16 and 14 kD zeins, and slight labeling of the less abundant 10 kD zein.

The titer of the antisera was also characterized by performing immunolabelling of blots with dilutions ranging from 1:50 to 1:1000 (for later bleeds). Although the lower dilutions of antisera immunolabelled the same zeins as the corresponding sera at higher dilutions, background staining of the membrane increased at sera dilutions of less than 1:500. Since the expected immunoreactivity profiles (as discussed above) were obtained at the 1:1000 dilution, this dilution was used for further analyses. Testing of the scra at dilutions of 1:2000 and higher might be indicated if sera conservation is desired, since dilutions of more than 1:1000 were not tested in these experiments.

The total amounts of sera obtained from the animals were as follows: 40 ml each of sera from rabbits 1, 4, and 6, and 80 ml each of scra from rabbits 2, 3, and 5. The latter rabbits were chosen for further bleeds because the immunoreactivity profiles appeared to be slightly more specific to the α-zeins in the case of sera from rabbits 2 and 3 than was serum from rabbit 1F (which may have shown a very slight reactivity with the 10 kD zein), and slightly more reactive with the 10 kD zein in the case of sera from rabbits 5 and 6 than was sera from rabbit 4F.

EXAMPLE 5

Transformation of Maize with Z10 Promoter-Antisense Constructs

Embryogenic maize type II cultures were initiated from immature embryos isolated from developing seed derived from a cross of the genotypes B73 and A188 as described in PCT publication WO 95/06128 and U.S. application Ser. No. 08/112,245. Type II cultures were microprojectile bombarded with a combination of plasmid vectors pDPG340 (Z10 promoter-Z4 antisense DNA sequence, described above) or pDPG380 (Z10 promoter-A20 antisense DNA sequence, described above) and pDPG363 comprising a plant expression cassette containing the Cauliflower Mosaic Virus 35S promoter operably linked in 5' to 3' order to intron 1 from the maize alcohol dehydrogenase I gene, the bar gene isolated from *Streptomyces hygroscopicus*, and the 3' terminator and polyadenylation sequences from the nopaline synthase gene of *Agrobacterium tumefaciens*. Transformed cell lines were selected for resistance to the herbicide bialaphos conferred by expression of the bar gene as described in U.S. Pat. No. 5,489,520, U.S. Pat. No. 5,550, 318, and PCT publication WO 95/006128. Transformation of maize is further described in U.S. Pat. No. 5,538,877, U.S. Pat. No. 5,538,880, and PCT publication WO 95/06128, the disclosures of which are incorporated by reference herein. The identification of transformed cell lines can be accomplished by employing selectable or screenable markers, as described hereinabove.

The presence of the antisense DNA sequence in transformants was verified by polymerase chain reaction (PCR). The sequence of the 5' PCR primer was TCTAGGAAGCAAG-GACACCACC (SEQ ID NO:5). The sequence of the 3' PCR primer was GCAAGACCGGCAACAGGATTCA (SEQ ID NO:6). The PCR reaction produced a DNA fragment of size about 1.0 kilobases in transformants containing pDPG380 and a DNA fragment of about size 1.1 kilobases in pDPG340 transformants.

Transformed callus lines containing antisense DNA sequences operably linked to a Z10 promoter were used to generate plants and seeds. Generally plants are regenerated as follows. Cells that survive the exposure to the selective agent, or cells that have been scored positive in a screening assay, were cultured in media that supports regeneration of plants. In an exemplary embodiment, the inventors modified MS and N6 media (see Table 1 of U.S. application Ser. No. 08/594,861, the disclosure of which is incorporated by reference herein) by including further substances such as growth regulators. A preferred growth regulator for such purposes is dicamba or 2,4-D. However, other growth regulators may be employed, including NAA, NAA+2,4-D or picloram. Media improvement in these and like ways was found to facilitate the growth of cells at specific developmental stages. Tissue was preferably maintained on a basic media with growth regulators until sufficient tissue was available to begin plant regeneration efforts, or following repeated rounds of manual selection, until the morphology of the tissue is suitable for regeneration, at least two weeks, then transferred to media conducive to maturation of embryoids. Cultures were transferred every two weeks on this medium. Shoot development will signal the time to transfer to medium lacking growth regulators.

The transformed cells, identified by selection or screening and cultured in an appropriate medium that supports regeneration, were then allowed to mature into plants. Developing plantlets were transferred to soilless plant growth mix, and hardened, e.g., in an environmentally controlled chamber at about 85% relative humidity, 600 ppm $CO_2$, and 25–250 microeinsteins $m^{-2}$ $s^{-1}$ of light. Plants were preferably matured either in a growth chamber or greenhouse. Plants were regenerated from about 6 weeks to 10 months after a transformant is identified, depending on the initial tissue. During regeneration, cells were grown on solid media in tissue culture vessels. Illustrative embodiments of such vessels were petri dishes and Plant Con®s. Regenerating plants were preferably grown at about 19° to 28° C. After the regenerating plants reached the stage of shoot and root development, they were transferred to a greenhouse for further growth and testing.

By providing fertile, transgenic offspring, one can subsequently, through a series of breeding manipulations, move a selected gene from one corn line into an entirely different corn line without the need for further recombinant manipulation. Movement of genes between corn lines is a basic tenet of the corn breeding industry, involving simply back crossing the corn line having the desired gene (trait). Introduced transgenes are valuable in that they behave genetically as any other corn gene and can be manipulated by breeding techniques in a manner identical to any other corn gene. Transformants containing Z10 promoter antisense constructs (pDPG340 and/or pDPG380) were crossed to various maize inbred lines, including elite inbred lines designated AW, CN, CV, and DD.

Figure 5:
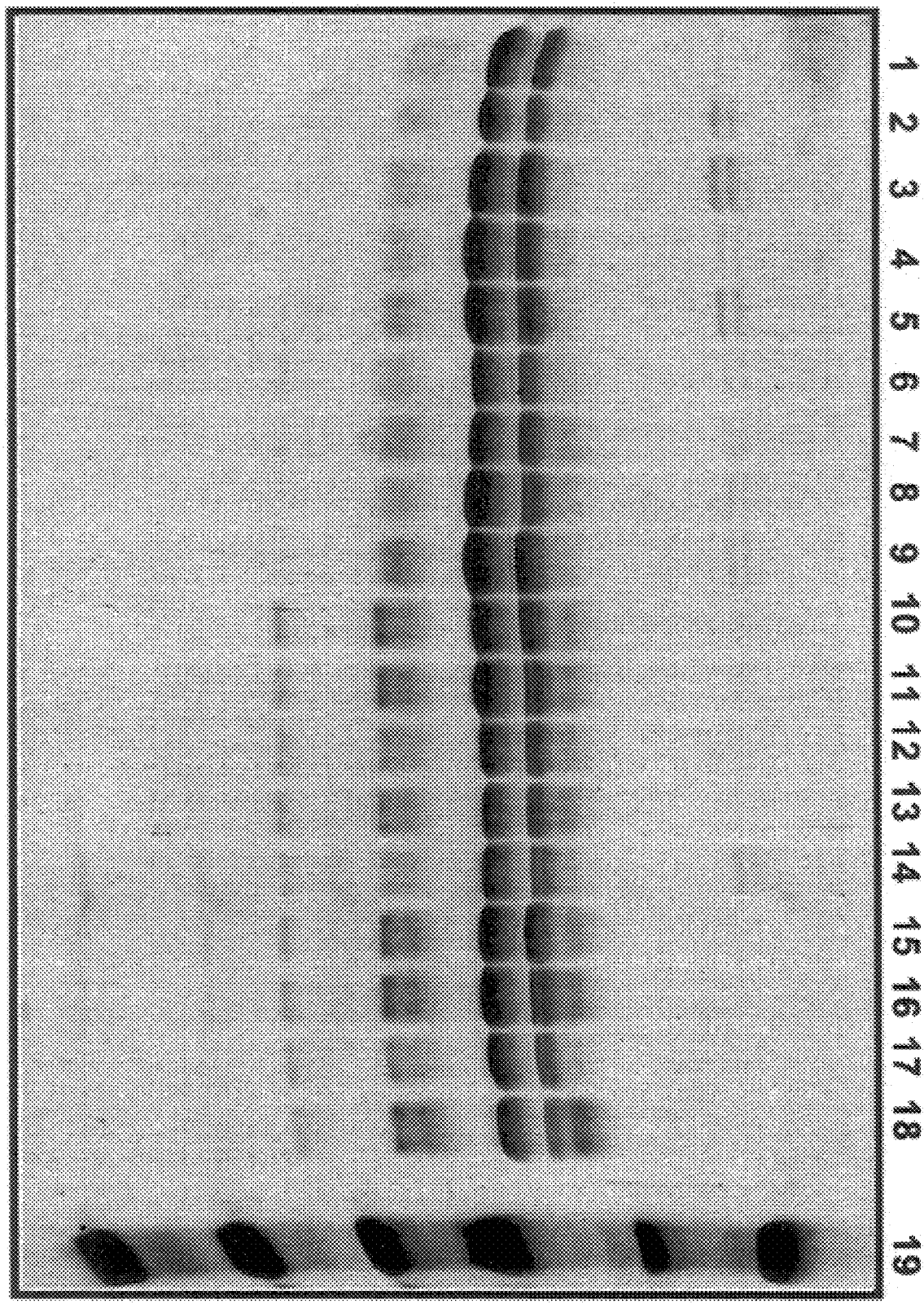
FIG. 5 shows SDS-PAGE analysis of zein extracts from individual kernels of segregating populations resulting from R1 crosses of a hemizygous transformant (GW01) carrying pDPG340 and pDPG380 to nontransforned inbreds, and R2 self-pollinations. Lanes 1–8 contain zein extracts from R2 kernels crossed to CN in the R1 generation and self-pollinated in the second generation. Lane 9 contains zein extract from untransformed CN. Lanes 10–17 contain zein extracts from R2 kernels crossed to AW in the first generation and self-pollinated in the second generation. Lane 18 contains zein extract from untransformed AW. Lane 19 contains molecular weight markers.

Zein proteins were extracted from mature kernels from a maize plant transformed with plasmids pDPG340 and pDPG380 and crossed to inbreds AW or CN, according to Tsai (1980), as follows. Fifty milligrams of ground kernel was suspended in 0.5 ml 70% ethanol, 1% β-mercaptoethanol and extracted at room temperature for 30 minutes to overnight. The sample was vortexed, centrifuged at 12,000 rpm for 5 minutes. Fifty microliters of the supernatant containing zein proteins was removed and dried. Zein proteins were resuspended in 50 μl SDS polyacrylamide gel loading buffer containing 1% β-mercaptoethanol. Protein was separated on SDS polyacrylamide gels and stained with Coomassie blue. No qualitative differences were observed in the amounts of 19 kD and 22 kD α-zein proteins (FIG. 5). Furthermore, overall protein expression in the kernel appears to be the similar in antisense transformants and untransformed maize lines.

Analysis of the amino acid composition of Z10-antisense DNA transformants was undertaken. Amino acids were extracted from mature kernels as described in Jarrett et al., 1986; Jones et al., 1983; AACC, 1995). Results are summarized inTable V. Data was analyzed by t-tests and differences noted between transformed and untransformed kernels that were significant at the $p<0.05$ level of significance. Transformed and untransformed kernels are from the same ear. The level of leucine only was statistically significantly decreased in transformant DD021. The level of lysine was statistically significantly increased and the level of leucine statistically significantly decreased in transformants DD015 and DD018. These results are expected if expression of α-zeins is depressed in antisense transformants and expression of other proteins in the endosperm are increased. α-Zein proteins are rich in leucine residues and therefore one would expect that in the presence of reduced expression of α-zein proteins, the level of leucine would decrease in the kernel. Similarly, non-zein proteins contain more lysine than zein proteins and therefore increased expression of non-zein proteins results in increased lysine levels in the kernel. Therefore, the amino acid composition data relating to Z10-antisense transformants is consistent with a slight reduction in α-zein expression and increased expression of non-zein proteins, resulting in decreased levels of leucine and increased levels of lysine in the seed. Similar increases in lysine and decreases in leucine levels are observed in the maize opaque-2 mutants in which zein synthesis is depressed and synthesis of non-zein proteins is increased. Opaque-2 mutants, however, exhibit, other phenotypic differences from wild type maize (Di Fonzo et al., 1988; Bass et al., 1992).

TABLE V

| Trans-formant | Lysine[a, b] | | Leucine[a, b] | |
| --- | --- | --- | --- | --- |
| | Transformed | Untransformed | Transformed | Untransformed |
| DD015 | 1.96* | 1.75 | 11.68* | 13.97 |
| | 2.13 | 1.90 | 11.69* | 14.50 |
| DD021 | 2.40 | 2.09 | 15.90* | 17.90 |
| | 2.13 | 2.03 | 16.97 | 17.75 |
| DD038 | 1.96 | 2.00 | 12.66 | 13.89 |
| | 1.82 | 1.96 | 15.87 | 15.73 |
| DD018 | 2.74* | 2.43 | 17.57 | 19.13 |
| | 2.30* | 2.15 | 13.19* | 15.52 |

[a]All amino acid concentrations are expressed as milligrams amino acid per gram of seed.
[b]Asterisk denotes that amino acid concentration is statistically significantly different from the amino acid concentration in an untransformed kernel. T-tests were performed to compare amino acid concentrations in isogenic transformed and untransformed kernels. Statistically significant differences are those for which $p -< 0.05$.

EXAMPLE 6

Transformation of Maize with Z27 Promoter-Antisense Expression Cassettes

Maize plants of the genotype A188×B73 were crossed to Hi-II maize plants (Armstrong et al., 1991). Immature embryos (1.2–2.0 mm in length) were excised from surface-sterilized, greenhouse-grown ears of Hi-II 11–12 days post-pollination. The Hi-II genotype was developed from an A188×B73 cross for high frequency development of type II callus from immature embryos (Armstrong et al., 1991). Approximately 30 embryos per petri dish were plated axis side down on a modified N6 medium containing 1 mg/l 2,4-D, 100 mg/l casein hydrolysate, 6 mM L-proline, 0.5 g/l 2-(N-morpholino)ethanesulfonic acid (MES), 0.75 g/l $MgCl_2$, and 2% sucrose solidified with 2 g/l Gelgro, pH 5.8 (#735 medium) Embryos were cultured in the dark for two to four days at 24° C.

Approximately four hours prior to bombardment, embryos were transferred to the above culture medium with the sucrose concentration increased from 3% to 12%. When embryos were transferred to the high osmoticum medium they were arranged in concentric circles on the plate, starting 2 cm from the center of the dish, positioned such that their coleorhizal end was orientated toward the center of the dish. Usually two concentric circles were formed with 25–35 embryos per plate.

Gold particles were prepared containing 10 μg pDPG165 (described in U.S. Pat. No. 5,489,520), and 10 μg of pDPG530.

The plates containing embryos were placed on the third shelf from the bottom, 5 cm below the stopping screen in the bombardment chamber. The 1100 psi rupture discs were used. Each plate of embryos was bombarded once. Embryos were allowed to recover overnight on high osmotic strength medium prior to initiation of selection.

Embryos were allowed to recover on high osmoticum medium (735, 12% sucrose) overnight (16–24 hours) and were then transferred to selection medium containing 1 mg/l bialaphos (#739, 735 plus 1 mg/l bialaphos or #750, 735 plus 0.2M mannitol and 1 mg/l bialaphos). Embryos were maintained in the dark at 24 C. After three to four week on the initial selection plates about 90% of the embryos had formed Type II callus and were transferred to selective medium containing 3 mg/l bialaphos (#758). Bialaphos resistant tissue was subcultured about every two weeks onto fresh selection medium (#758). Transformants were confirmed using PCR analysis to detect presence of plasmid pDPG530. PCR primers used to confirm presence of the Z27-antisense expression cassette in transformed tissue were as follows: 5'GCA CTT CTC CAT CAC CAC CAC 3' (SEQ ID NO:6) and 5'TAT CCC CTT TCC AAC TTT CAG 3' (SEQ ID NO:7). PCR amplification of pDPG530 and pDPG531 transformants produced a DNA product of about 500 base pairs.

Transformants were regenerated as generally described in PCT publication WO 95/06128. Transformed embryogenic callus was transferred to regeneration culture medium (MS culture medium (Murashige and Skoog, 1962), containing 0.91 mg/L L-asparagine, 1.4 g/L L-proline, 20 g/L D-sorbitol, 0.04 mg/L naphthalene acetic acid (NAA) and 3 mg/L 6-benzylaminopurine). Cells were grown for about four weeks on this culture medium with a transfer to fresh medium at about 2 weeks. Transformants were subsequently transferred to MSO culture medium (MS medium with no phytohormones added). Regenerated plants were transferred to soil as described previously in this application. Plants were crossed to maize inbred lines designated AW, CV, and DJ. Seed containing the Z27-antisense expression cassette were opaque in phenotype similar to kernels of opaque-2 mutant kernels. Furthermore, seed resulting from crosses of hemizygous Z-27-antisense transformants to untransformed inbreds resulted in seed segregating for the opaque phenotype in correlation with the presence of the Z-27 antisense expression cassette DNA sequence.

Figure 6:
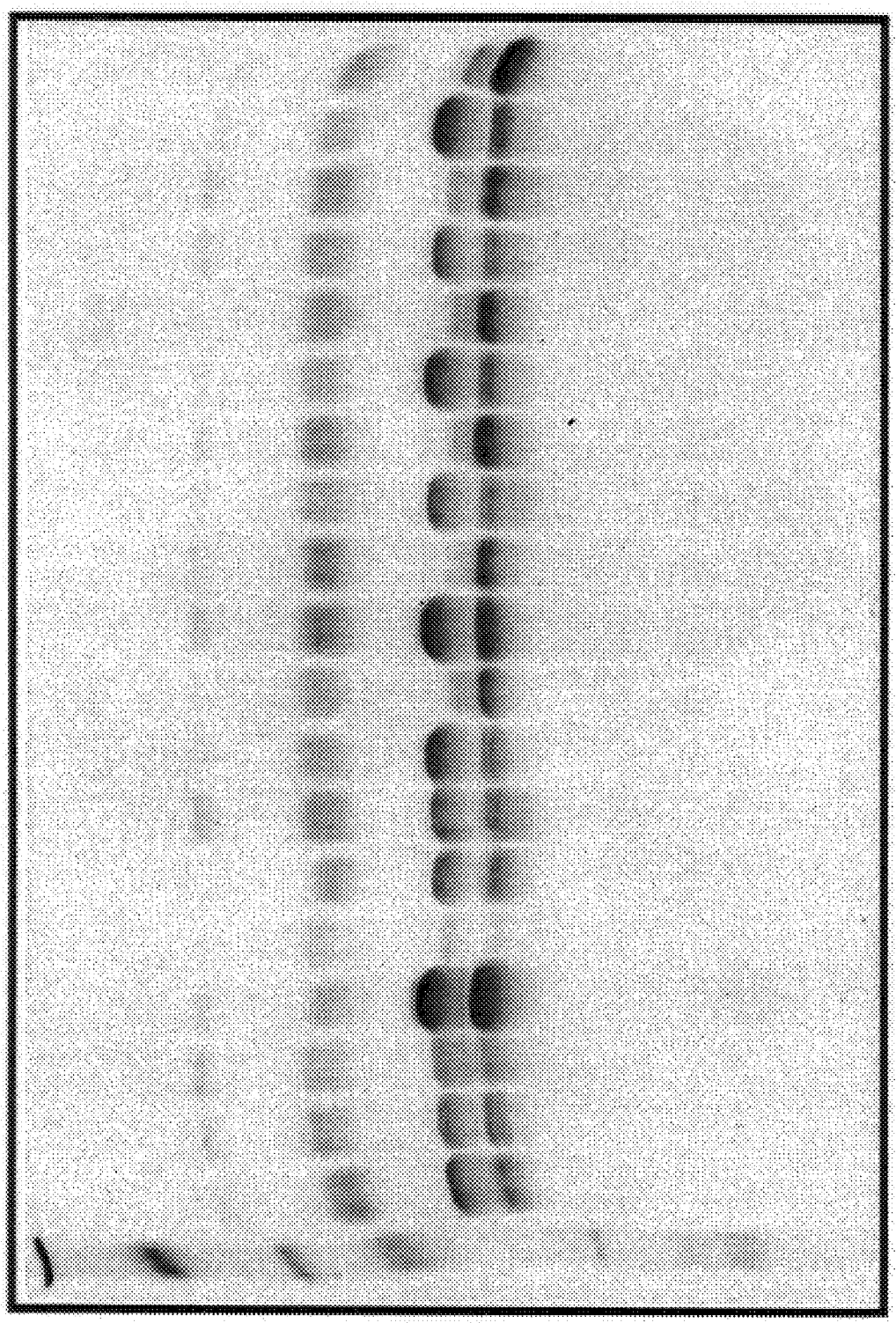
FIG. 6 shows SDS-PAGE analysis of zein extracts of vitreous or opaque kernels from segregating populations resulting from crosses of hemizygous pDPG530 transformants to untransformed inbreds AW and CV. KP014×AW (lanes 1–2); AW×KP014 (lanes 3–4); KP015×AW (lanes 5–6); AW×KP015 (lanes 7–8); CV×KP015 (lanes 9–10); AW×KP015 (lanes 11–12). Lanes 13–19 are AW, CV, ILP, IHP, AK835 opaque, AK835 normal, and W64A opaque, respectively. Lane 20 contains molecular weight markers.
Figure 7:
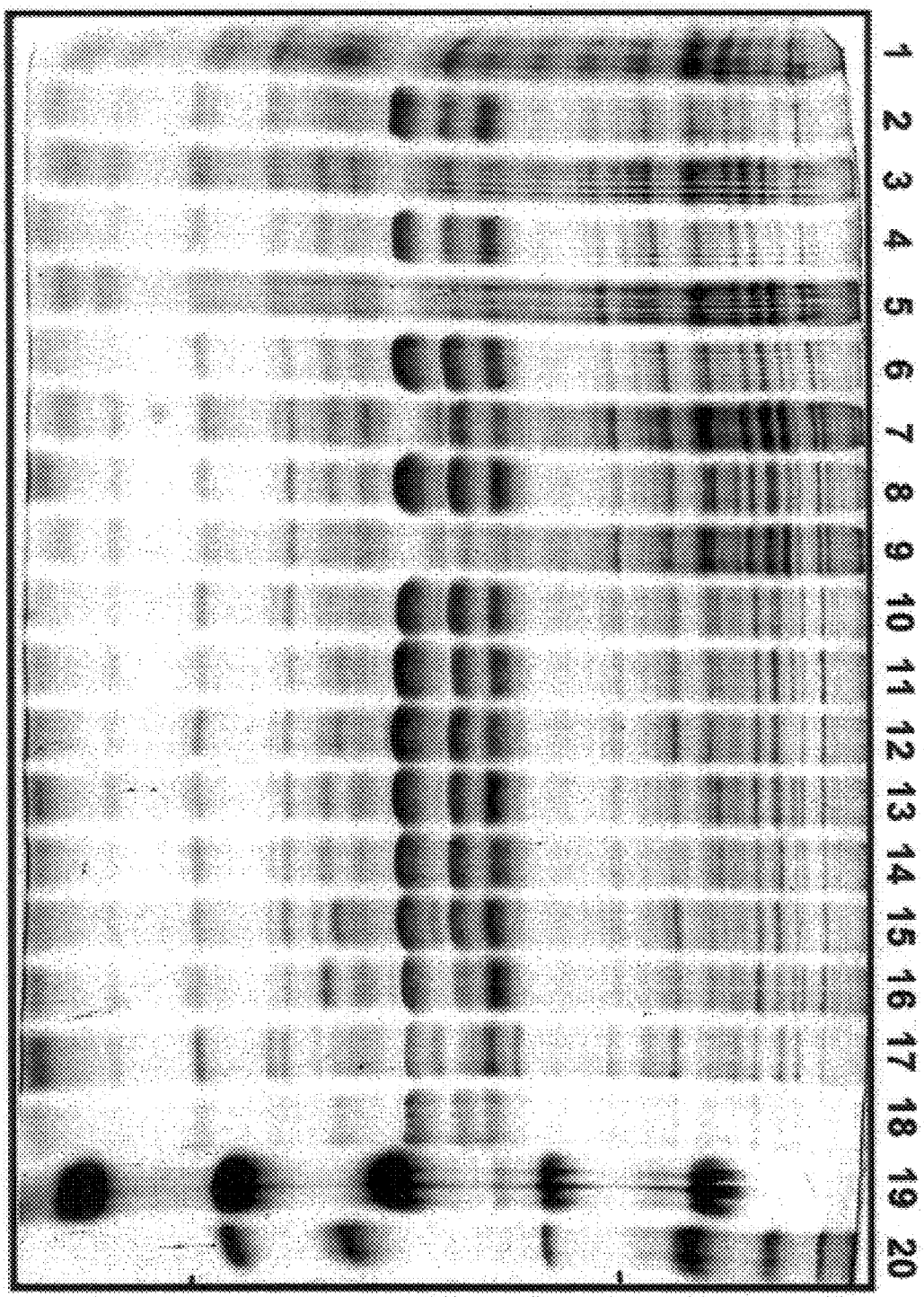
FIG. 7 shows SDS-PAGE analysis of zein extracts of proteins from individual kernels of segregating populations resulting from crosses of hemizygous transformants and untransformed inbreds. pDPG530 transformant KP015 (AW×KP015, lanes 1–2; CV×KP015, lanes 3–4; KP015× AW, lanes 5–6, and KP016 (CV×KP016, lanes 7–8; KP016× AW, lanes 9–10) andpDPG531 transformant KQ018 (KQ018×AW, lanes 11–12). Lanes 13–18 are untransformed controls CW, AR, CV, AW, W64A, O2 and W64A, respectively. Lanes 19–20 contain molecular weight markers.

Zein proteins were extracted from mature kernels from maize plants transformed with plasmids pDPG530 and crossed to inbreds AW or CV as follows. Fifty milligrams of ground kernel was suspended in 0.5 ml 70% ethanol, 1% β-mercaptoethanol and extracted at room temperature for 30 minutes to overnight. The sample was vortexed, centrifuged at 12,000 rpm for 5 minutes. Fifty microliters of the supernatant containing zein proteins was removed and dried. Zein proteins are resuspended in 50 μl SDS polyacrylamide gel loading buffer containing 1% β-mercaptoethanol. Protein was separated on SDS polyacrylamide gels and stained with Coomassic blue. Reduced amounts of 19 kD and 22 kD α-zeins were observed in five analyzed transformants. A Coomassie blue stained polyacrylamide gel of pDPG530 transformants and isogenic controls is shown in FIG. 6. In one transformant, designated KP014, expression of the 27 kD zein protein, a γ type zein protein was also depressed, suggesting that expression of an antisense DNA sequence in a maize may reduce expression of a related family of genes, i.e., the α-zeins, but also a member of a related family of proteins, i.e., 27 kD zein. A similar reduction in 27 kD was also observed for sense DNA sequences (see FIG. 10). Isogenic controls were segregating kernels derived from plants lacking pDPG530 DNA sequences, recovered from crosses of pDPG530 transformed plants to untransformed inbreds. Furthermore, overall protein expression in the kernel appears to be the greater in antisense transformants than in untransformed maize lines as evidenced by overall protein staining by Coomassie blue on polyacrylamide gels (FIG. 7). Reduction of α-zein synthesis is observed in opaque-2 mutants, but the reduction is much less than in Z4 antisense expressing maize transformants.

Figure 8A:
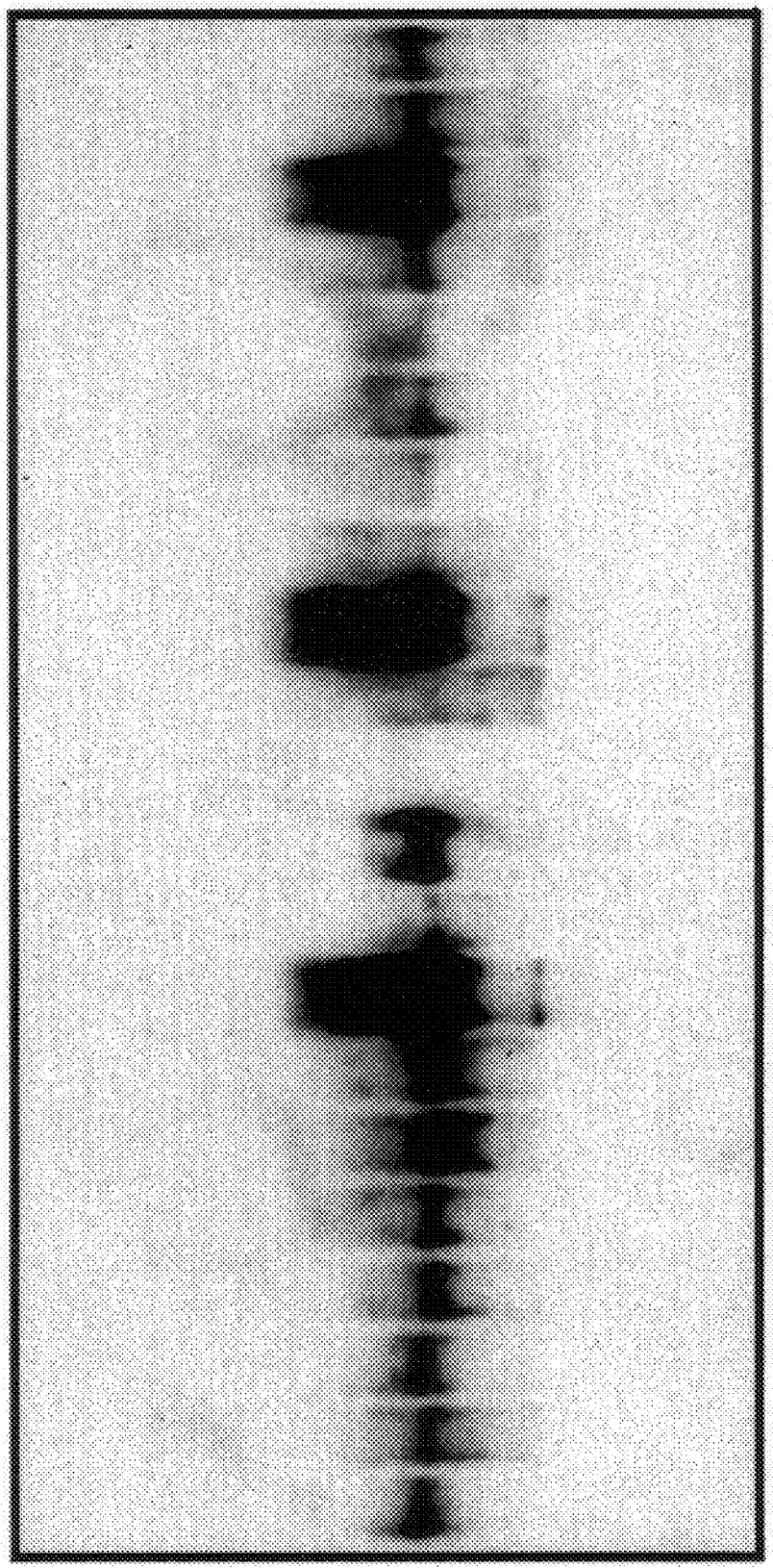
FIG. 8 shows α-zein mRNA levels in developing kernels from a segregating population resulting from crosses of hemizygous pDPG530 and pDPG531 transformants to untransformed inbreds AW and CV. AW×KP015 (pDPG530 transformant; lanes 1–10; top panel); KP015×AW (pDPG530 transformant; lanes 11–20; top panel); CV×KP015 (pDPG530 transformant; lanes 1–10; lower panel); and KQ012×AW (pDPG531 transformant; lanes 11–20; lower panel). Kernels were isolated 21 days post-pollination.
Figure 8B:
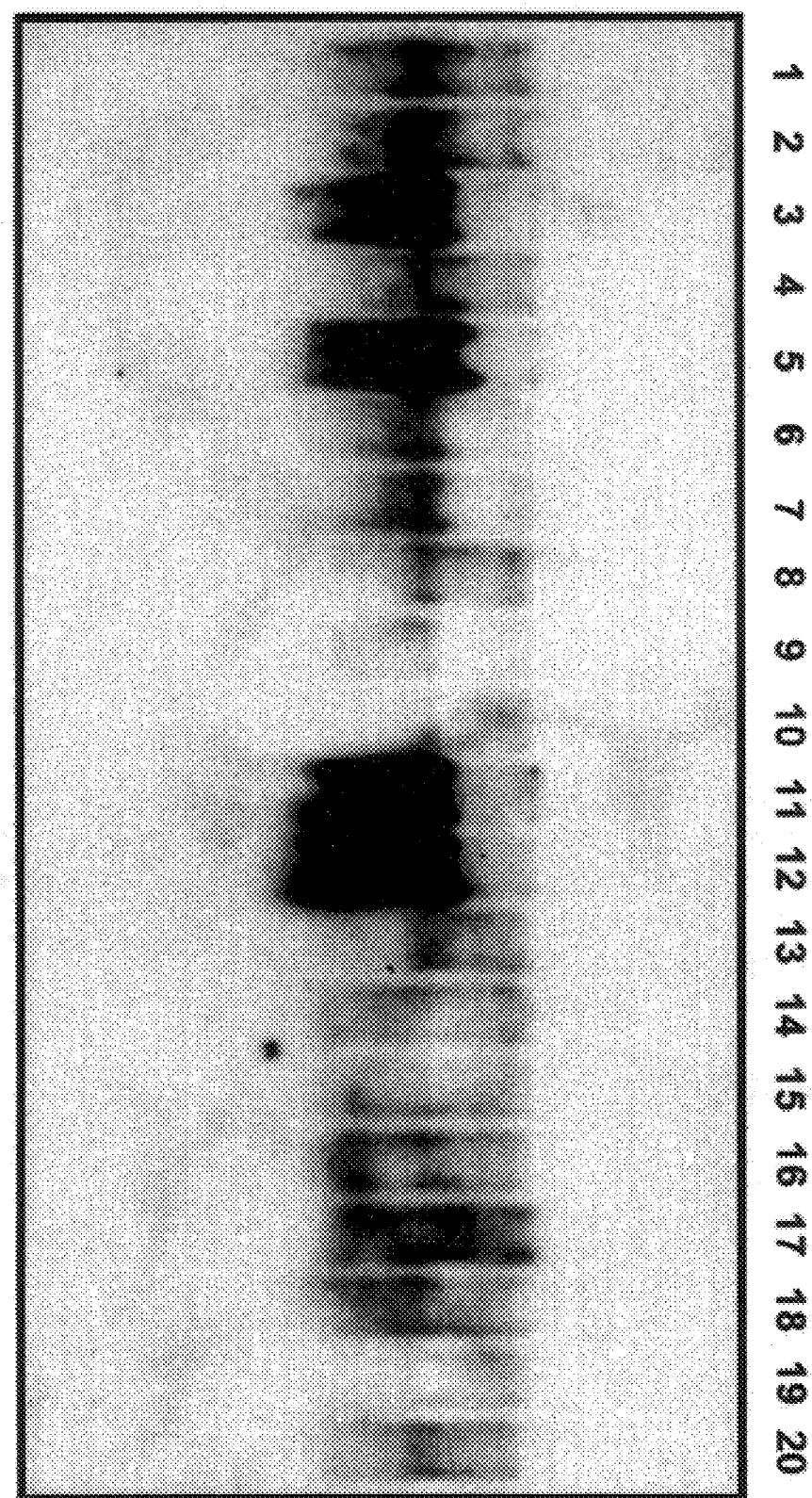

It is contemplated that antisense repression of zein protein synthesis in the seed is a result of reduction in the amount of zein RNA present in the cell and consequently less synthesis of zein proteins. Northern blot analysis was completed to determine the level of steady state zein RNA synthesis in pDPG580 transformants. Procedures for Northern blot analysis are described in Sambrook et al. (1989). RNA isolated from maize kernels 21 days after pollination was separated by agarose gel electrophoresis and blotted to a Nitrobind membrane. The blot was probed with the Z4 coding sequence. A Northern blot analysis of the KP015 transformant is shown in FIG. 8. Darker signals on the autoradiograph, e.g., lanes 3, 9, and 14 (upper panel) and lanes 3, 5, 11, and 12 (lower panel), correspond to untransformed seeds which showed normal level of zein synthesis. Other lanes (lighter signals) correspond to kernels that showed reduced levels of zein synthesis and the opaque phenotype in seeds containing the expression cassette.

Analysis of the amino acid composition of Z27-antisense DNA transformants was undertaken. Amino acids were extracted from mature kernels derived from three independent transformed lines as follows. Fifty milligrams of ground corn meal was hydrolyzed in 1 ml 6N HCl under argon gas for 24 hours at 110° C. Samples were diluted to 50 ml and filtered through a 0.45 micron filter. Norvaline as added to each sample as an internal standard prior to HPLC analysis. Amino acids are separated on a Supelcosil LC-8 HPLC column (Jarrett et al. , 1986; Jones et al., 1983; AACC, 1995). Results from analysis of single kernels are summarized in Table VI. Data was analyzed by t-tests and differences noted between transformed and untransformed kernels that were significant at the $p<0.05$ level of significance. Transformed and untransformed kernels are isogenic segregants from a breeding population. Lysine levels were statistically significantly increased in all kernels analyzed from the KP015 and KP016 transformants and lysine was increased in four of six kernels analyzed from the KP014 transformant. As expected leucine levels were decreased in most transformed kernels that were analyzed. These data demonstrate that expression of an antisense Z4 DNA sequence in transformed maize kernels causes reduction in the quantities of α-zeins present in the kernel. Total protein in the antisense expressing kernel does not appear to be reduced. Furthermore, the observed decrease in α-zeins correlates with transformed kernels with an opaque phenotype.

TABLE VI

| Trans- | Lysine[a, b] | | Leucine[a, b] | |
|---|---|---|---|---|
| formant | Transformed | Untransformed | Transformed | Untransformed |
| KP014 | 2.60* | 2.08 | 13.94 | 16.85 |
|  | 2.85* | 2.22 | 15.03* | 17.08 |
|  | 3.09* | 2.40 | 15.66 | 18.14 |
|  | 2.94* | 2.45 | 15.27* | 19.14 |
|  | 2.60 | 2.56 | 10.08 | 14.95 |
|  | 2.45* | 2.08 | 9.21 | 10.58 |
| KP015 | 1.90* | 1.02 | 3.85* | 7.80 |
|  | 1.92* | 1.02 | 3.86* | 7.98 |
|  | 1.48* | 0.94 | 4.44* | 5.87 |
|  | 1.43* | 1.01 | 4.32* | 6.26 |
| KP016 | 2.10* | 1.52 | 8.58* | 11.90 |
|  | 2.17* | 1.54 | 8.95* | 11.65 |
|  | 2.66* | 2.03 | 14.16* | 20.37 |
|  | 2.76* | 1.81 | 14.68* | 18.66 |
|  | 4.65* | 2.14 | 11.01* | 21.32 |
|  | 4.51* | 2.31 | 11.26* | 23.28 |
|  | 3.91* | 2.22 | 12.96* | 23.99 |
|  | 3.98* | 2.36 | 13.29* | 24.06 |
|  | 2.47* | 1.76 | 9.60* | 16.55 |
|  | 2.48* | 1.70 | 9.70* | 14.83 |

*Denotes differences from untransformed kernels that are statistically significant at the $p < 0.05$ level of confidence.

Figure 9A:
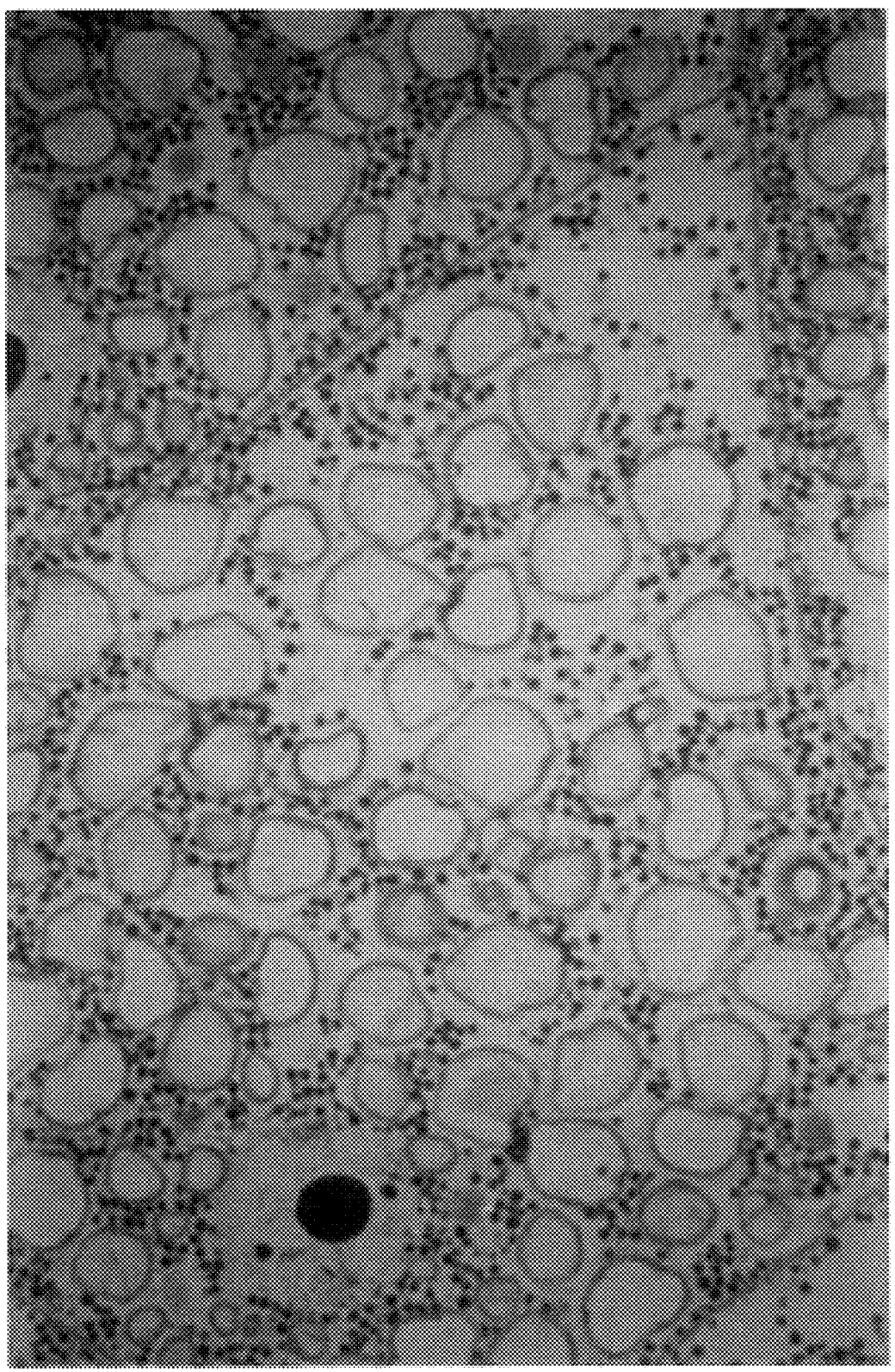
FIG. 9 shows the ultrastructure of pDPG530 transformed (right) and untransformed (left) kernels.
Figure 9B:
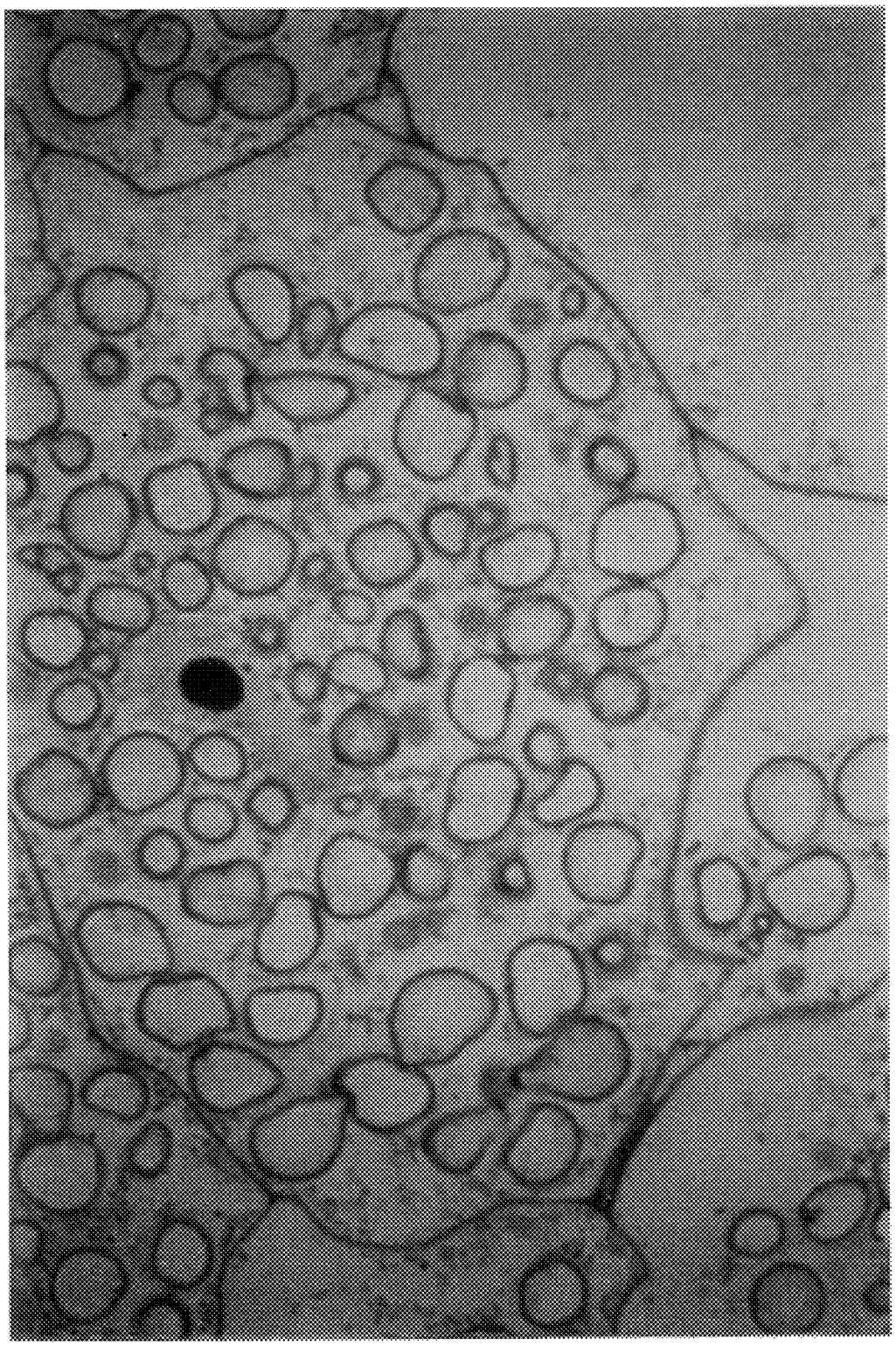

Endosperm cells in the maize kernel are comprised primarily of large starch granules and protein sequestered in protein bodies (Lopes and Larkins, 1993). Zein proteins are essential for maintaining structure of the protein bodies (Lending and Larkins, 1989). A reduction in the number of protein bodies present in endosperm cells derived from a Z27 promoter-antisense transformant was observed by light microscopy (FIG. 9). This observation is further evidence that α-zein synthesis was reduced in the Z27 promoter-antisense DNA transformants.

EXAMPLE 7

Transformation of Maize with Z27 Promoter-Sense Expression Cassettes

In higher plants the phenomenon of co-suppression of gene expression has been described (Napoli et al., 1990). Co-suppression refers to the suppression of endogenous gene expression by expression of a transgenic sense DNA expression cassette. It was contemplated that a sense zein expression cassettes in maize may result in suppression of endogenous zein expression in a manner similar to that described in Example 6 following expression of an antisense expression cassette.

Plasmid vector pDPG531 comprises a Z27 promoter-Z4 sense coding sequence-nopaline synthase 3' region expression cassette. pDPG531 differs from pDPG530 in that the Z4 coding sequence is operably linked to the Z27 in the opposite orientation, i.e., pDPG531 is capable of being transcribed and translated into the 22 kD zein protein. Plasmid pDPG531 and pDPG165 were introduced into maize cells as described in Example 6. Transformants were selected and regenerated as described in Example 6. Plants were regenerated from three Z27-Z4 sense expression cassettes and crossed to inbreds designated AW, CV, and CN.

Figure 10:
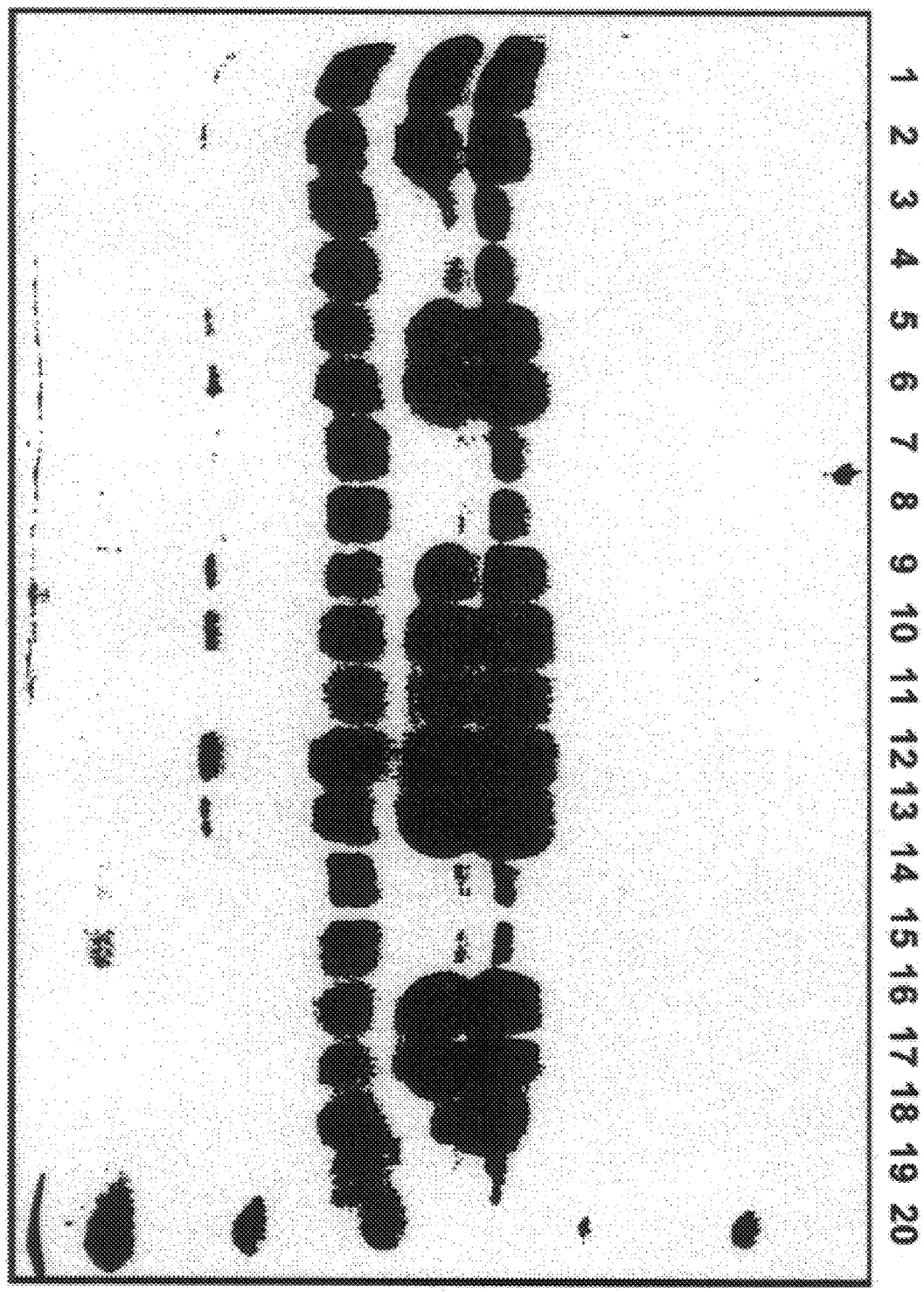
FIG. 10 shows SDS-PAGE analysis of zein extracts from segregating populations resulting from crosses of pDPG531 transformants to untransformed inbreds AW and CV. CV×KQ012 (lanes 1–4); KQ012×AW (lanes 5–8); KQ020× AW (lanes 13–15); KQ020×CV (lanes 16–19). Controls CW, AR, CV and AW (lanes 9–12, respectively). Lane 20 contains a molecular weight marker.

The amount of α-zein proteins present in untransformed and Z27-Z4 sense transformants was compared on Coomassie blue stained polyacrylamide gels as described previously in reference to analysis of antisense transformants. Sample preparation and analysis were performed as described in Example 6. FIG. 10 shows a Coomassie blue stained polyacrylamide gel. Each lane represents zein proteins extracted from a single seed of a segregating population of untransformed and sense expression cassette transformed seed. Lanes 1 through 8 represent seed derived from the transformant designated KQ012, and lanes 13 through 19 represent seed derived from a second transformant designated KQ020. Lanes 9 through 12 represent untransformed maize seed. Lanes 3, 4, 7, 8, 14, and 15 represent sense expression cassette transformed seed in which the α-zein levels are surprisingly greatly reduced in a manner comparable to that observed in antisense transformants. In addition to the unexpected reduction in zein protein concentration in sense transformants, seed with reduced zein content also generally exhibit the opaque phenotype, and a reduction in Z27 zein levels.

In order to further determine whether the phenotype of Z27 promoter- Z4 sense transformants was similar to antisense transformants, lysine and leucine concentrations were analyzed in seed derived from individual kernels. Amino acids were analyzed as described in Example 6. In one transformant, designated KQ018, lysine and leucine levels were statistically the same in isogenic transformed and untransformed seed. However, in a transformant designated KQ012, lysine levels were statistically increased in the transformant and leucine levels were statistically significantly decreased in the transformant. It is therefore apparent, that the Z27 promoter- Z4 sense transformants produce a seed morphology, protein, and amino acid composition phenotype, similar to that observed in antisense transformants.

EXAMPLE 8

Method to Increase Content of Methionine in Plants

A method for increasing the methionine content of seeds involves cotransforming maize tissue culture with a zein sense or antisense DNA sequence (either A20 or Z4) and a DNA sequence containing a gene encoding a 10 kD zein protein. It is known that the 10 kD zein proteins are rich in methionine. A decrease in expression of A20 and/or Z4 zein proteins combined with an increase in expression in the 10 kD zein proteins is likely to lead to about a 50% to 300% increase in total weight percent of methionine in the seed.

Antisense or sense DNA sequences containing a DNA sequence complementary or homologous to A20 and/or Z4 have been prepared as described in Examples 2 and 7. Conditions for successful transformation of maize cell lines with the sense or antisense DNA sequence have been described in Examples 5 and 6.

A DNA sequence containing a gene encoding a 10 kD zein protein was prepared as described in U.S. Pat. No. 5,508,468, which is hereby incorporated reference. Preferably, a Z10 DNA sequence contains a gene encoding a 10 kD zein protein including the 3' noncoding sequence combined with the promoter from a 27 kD zein protein. A plasmid with this DNA sequence has been prepared and is designated pZ27Z10 and is described in U.S. Pat. No. 5,508,468.

Transformed callus lines, plants, and seeds containing a DNA sequence encoding a 10 kD zein protein were prepared as described in Examples 5 and 6. Met1 seeds were generated as described in U.S. Pat. No. 5,508,468.

The expression of the chimeric Z10 gene at the RNA level in Met1 seeds was demonstrated. Immature endosperms (21 DAP) were harvested from a segregating ear of the background Met1×A654 BC2. Both DNA and RNA were prepared from individual endosperm samples. The DNA was analyzed by PCR for the presence/absence of the Z27Z10 gene. The RNA samples were analyzed by Northern blot, probing with an oligonucleotide spanning the junction between the Z27 promoter and the Z10 coding region. The results demonstrate that the gene is expressed in endosperm tissue of PCR+ seeds and not in that of PCR− seeds.

Seeds containing a DNA sequence containing the 10 kD zein protein combined with the 27 kD promoter were field tested. A total of 130 ears were genotyped by PCR (using DNA from pooled leaf samples of germinated seedlings) and analyzed for methionine content by amino acid analysis, and 10 kD zein levels by ELISA. There is a positive correlation between 10 kD zein levels and methionine content in several maize backgrounds tested. It is, therefore, contemplated that if α-zein synthesis is reduced by expression of sense or antisense zein constructs, expression of a transgenic 10 kD zein will increase the methionine content of a seed. The results indicate that if it is possible to elevate the expression of the 10 kD zein at least about 5–10 fold, methionine contents in maize seed can be significantly raised (up to 2.5 to 3%). Additional transformants with the 10 kD zein functionally linked to the 27 kD zein promoter and/or the Z4 22 kD zein promoter and/or the 10 kD zein promoter which show elevated levels of 10 kD zein and methionine in transformed seed have also been generated as described above and in U.S. Pat. No. 5,508,468.

Maize tissue cultures are cotransformed with a sense or antisense DNA sequence and a 10 kD zein DNA sequence and a selectable marker gene. Transformed cell lines containing both DNA sequences are identified by PCR analysis.

The transformed cell lines positive for PCR analysis for both an antisense and the 10 kD zein DNA sequences are used to regenerate transformed plants and seeds, as described in Example 6. Seeds are analyzed for expression of 10 kD zein and Z4 (22 kD) using Western blots. Total methionine content of the seed is determined as described in Examples 5 and 6.

An increase in the 10 kD zein expression combined with a decrease in the A20 and/or Z4 zein protein results in a significant increase (up to about 50 to 300%) in the total methionine content of the seed.

EXAMPLE 9

Method to Increase Amino Acid Content of Particular Amino Acids in Seeds

The amino acid content of seeds is increased by expression of a gene encoding a synthetic polypeptide that comprises one or more amino acids for which altered levels are desired in the seed. Amino acid content is altered by expression of a gene encoding a naturally occurring or synthetic polypeptide comprising one or more desired amino acids, in a seed in which expression of endogenous seed storage proteins have been repressed by expression of a sense or antisense seed storage protein DNA sequence.

For example, a gene encoding the synthetic protein MB1 is introduced into a plant in which storage protein synthesis is repressed by expression of a sense or antisense DNA sequence. The MB1 coding sequence is introduced into a transgenic plant with reduced expression of storage protein, wherein said plant was previously transformed with a storage protein sense or antisense DNA sequence. Alternatively, the MB1 sequence is transformed into a plant simultaneously with a storage protein sense or antisense DNA sequence. In a preferred embodiment of the present invention, a storage protein antisense or sense expression cassette and an MB1 expression cassette are transformed into maize simultaneously or sequentially as described in Examples 5, 7, and 8.

A plasmid vector, designated pDPG780, containing an MB1 plant expression cassette was constructed. The MB1 protein coding sequence was obtained from Mary A. Hefford (Center for Food and Animal Research, Agriculture and Agri-Food Canada, Ottawa, ON, K1A 0C6, Canada) and the DNA sequence is disclosed in Beauregard et al., 1995. MB1 is a synthetic protein enriched in methionine, threonine, lysine and leucine and exhibits α-helical structure similar to a zein protein. Plasmid vector pDPG780 was constructed by operably linking an endoplasmic reticulum signal sequence (Pedersen et al., 1986) from the 15 kD zein protein encoding gene 5' to the MB1 coding sequence. The 15 kD zein-MB1 sequence was inserted in plasmid vector pZ27-nos between the Z27 promoter element and the nopaline synthase 3' region (nos). The expression cassette comprises in 5' to 3' orientation, the Z27 promoter, Z15 signal sequence, MB1 coding sequence, and nos 3' region. One of skill in the art could construct addition plasmid vectors containing a seed specific promoter operably linked to an endoplasmic reticulum signal sequence, protein encoding sequence, and 3' region, wherein said protein encoding sequence comprises a DNA sequence encoding a protein of desired amino acid composition.

The plasmid vector pDPG780 is introduced into maize in conjunction with a vector comprising a selectable marker gene, e.g., pDPG165 comprising the bar gene. The MB1 expression cassette is transformed into maize plants containing a sense or antisense zein transgene in which synthesis of δ-zein proteins is repressed. Alternatively, the sense or antisense zein construct is transformed into maize simultaneously with the MB1 expression cassette.

Plants are regenerated as described in Examples 5, 6 and 7. Protein composition of seed is analyzed by polyacrylamide gel electrophoresis as described in Examples 5 and 6. Reduction in zein proteins is observed and expression of a protein of desired amino acid composition is observed. Amino acid composition of seed is determined as described in Examples 5, 6, and 7. Levels of desired amino acids are altered in accordance with the amino acid composition of the protein encoded by the transgene.

While the present invention has been described in connection with the preferred embodiment thereof, it will be understood many modifications will be readily apparent to those skilled in the art, and this application is intended to cover any adaptations or variations thereof. All patents, patent documents and publications described herein are hereby incorporated by reference.

REFERENCES CITED

Altenbach, S. B., Pearson, K. W., Meeker, G., Staraci, L. C., Sun, S. S. M. 1989. *Plant Molecular Biology* 13:513–522. Enhancement of the methionine content of seed proteins by the expression of a chimeric gene encoding a methionine-rich protein in transgenic plants.

American Association of Cereal Chemists. 1995. Approved Methods. Vol. 1. Ninth edition.

An, G. 1987. *Methods in Enzymology*. 153:292.

Armstrong, C. L., Green, C. E., & Phillips, R. L. 1991. *Maize Genetics Cooperation Newsletter*. 65:92–93. Development and availability of germplasm with high Type II culture formation response.

Bass, H. W., Webster, C., O'Brian, G. R., Roberts, J. K. M., Boston, R. S. 1992. *Plant Cell*. 4:225–234. A Maize Ribosome-Inactivating Protein Is Controlled By The Transcriptional Activator Opaque-2.

Beauregard, M., Dupont, C., Teather, R. M., Hefford, M. A. 1995. *Bio/Technology*. 13:974–981. Design, Expression, And Initial Characterization Of MB1, A De Novo Protein Enriched In Essential Amino Acids.

Bevan M., Barnes, W. M., Chilton, M. D. 1983. *Nucleic Acid Research*. 11:369–385. Structure and transcription of the the Nopaline synthac gene of T-DNA.

Brandle, J. E., McHugh, S. G., James, L., Labbé, H., and Miki, B. L. 1995. *Bio/Technology*. 13:994–998. Instability of Transgene Expression in Field Grown Tobacco Carrying the csr1-1 Gene for Sulfonylurea Herbicide Resistance.

Chandler V. L., Radicella, J. P., Robbins, P. P., Chen, J., and Turks, D. 1989. *The Plant Cell*. 1:1175–1183. Two Regulatory Genes of the Maize Anthocyanin Pathway are Homologous: Isolation of B Utilizing R Genomic Sequences.

Christou, P., Murphy, J. E., & Swain, W. F. 1987. *PNAS*. 84:3962–3966. Stable transformation of soybean by electroporation and root formation from transformed callus.

Coe, E. H., Neuffer, M. G., and Hoisington, D. A. 1988. in *Corn and Corn Improvement*, eds. Sprague, G. F. & Dudley, J. W. (Am. Soc. Agron., Madison, Wis.), pp. 81–258.

Coruzzi, G., Broglie, R., Edwards, C. & Chua, N.-H. 1971. *EMBO J*. 3:1671. Tissue-specific and light-regulated expression of a pea nuclear gene encoding the small subunit of ribulose-1,5-bisphosphate corboxylase.

D'Halluin, K., Bonne, E., Bossut, M., De Beuckeleer, M., and Leemans, J. 1992. *The Plant Cell*. 4:1495–1505. Transgenic Maize Plants by Tissue Electroporation.

Dale, N. 1996. Feedstuffs Reference Issue. 68:24–31.

Dekeyser, R., Claes, B., De Rycke, R. M. U., Habets, M. E., Van Montague, M. C., & Caplan, A. B. 1990. *The Plant Cell*. 2:591–602. Transient Gene Expression in Intact and Organized Rice Tissues Dellaporta, S., Greenblatt, B. J., Kermicle, J., Hicks, J. B., Wessler, S. 1988. In: *Chromosome Structure and Function: Impact of New Concepts*, 18th Stadler Genetics Symposium, Jp.P. Gustafson and R. Appels, eds. (New York: Plenum Press) pp. 263–282

DiFonzo, N., Hartings, H., Brembilla, M., Motto, M., Soave, C., Navarro, E., Palau, J., Rhode, W. and Salamini, F. 1988. *Mol. Gen. Genet*. 212: 481–487. The B-32 Protein From Maize Endosperm, An Albumin Regulated By The O2 Locus: Nucleic Acid (cDNA) And Amino Acid Sequences.

Ebert, P. R., Ha, S. B., An. G. 1987. *Proc. Natl. Acad. Sci. USA*. 84:5745–5749. Identification of an essential upstream element in the nopaline synthase promoter by stable and transient assays.

Flavell, R. B. 1994. *Proc. Natl. Acad. Sci. USA*. 91:3490–3496. Inactivation Of Gene Expression In Plants As A Consequence Of Specific Sequence Duplication.

Fromm, M. E., Morrish, F., Armstrong, C., Williams, R., Thomas, J. and Klein, T. M. 1990. *Bio/Technology*. 8:833–839. Inheritance And Expression Of Chimeric Genes In The Progeny Of Transgenic Maize Plants.

Geraghty, D. E., Messing, J., Rubinstein, I. 1982. *EMBO J*. 1:1329. Sequence Analysis And Comparison Of cDNAs Of The Zein Multigene Family.

Gordon-Kamm, W. J., Spencer, T. M., Mangano, M. L., Adams, T. R., Daines, R. J., Start, W. G., O'Brien, J. V., Chambers, S. A., Adams, Jr., W. A., Willetts, N. G., Rice, T. B., Mackey, C. J., Krueger, R. W., Kausch, A. P., & Lemaux, P. G. 1990. *The Plant Cell*. 2:603–618. Transformation of Maize Cells and Regeneration of Fertile Transgenic Plants.

Hansel, L. W., Tsai, C. Y., Nelson, O. E. 1973. *Cereal Chem*. 50:383. The Effect Of The Floury-2 Gene On The Distribution Of Protein Fractions And Methionine In Maize Endosperm.

Hayashimoto, A., Li, Z., Murai, N. 1990. *Plant Physiol*. 93:857–863. A Polyethylene Glycol-Mediated Protoplast Transformation System For Production Of Fertile Transgenic Rice Plants.

Heidecker, G. and Messing, J. 1986. *Ann Rev Plant Physiol*. 37:439–466. Structural Analysis Of Plant Genes.

Hinchee, M. A. W., Connor-Ward, D. V., Newell, C. A., McDonell, R. E., Sato, S. J., Gasser, C. S., Fischhoff, D. A., Re, C. B., Fraley, R. T., Horsch, R. B. 1988. *Bio/Technology*. 6:915–922. Production Of Transgenic Soybean Plants Using Agrobacterium-Mediated DNA Transfer.

Horsch, R. B., Fry, J. E., Hoffmann, N. L., Eichholtz, D., Rogers, S. G. and Fraley, R. T. 1985. *Sciencep*. 227:1229–1231. A Simple And General Method For Transferring Genes Into Plants.

Hu, N.-T., Peifer, M. A., Heidecker, G., Messing, J., Rubenstein, I. 1982. *EMBO J*. 1:1337. Primary Structure Of A Genomic Zein Sequence Of Maize.

Hudspeth, R. L. and Grula, J. W. 1989. *Plant Molecular Biology*. 12:579–589. Structure and expression of the maize gene encoding the phosphoenolpyruvate carboxylase isozyme involved in $C_4$ photosynthesis. Ikuta, N., Souza, M. B. N., Valencia, F. F., Castro, M. E. B., Shenberg, A. C. G. Pizzirani-Kleiner, A., Astolfi-Filho, S. 1990. *Bio/technology*. 8:241–242. The α-amylase gene as a marker for gene cloning: Direct screening of recombinant clones.

Jarrett, H. W., Cooksy, K. D., Ellis, B., and Anderson, J. M. 1986. Analytical Biochemistry. 153:189–198 The Separation of o-Phthalaldehyde Derivatives of Amino Acids by Reversed-Phase Chromatography on Octylsilica Columns.

Jefferson, R. A. 1987. *Plant Molecular Biology Reporter*. 5:387–405 Assaying Chimeric Genes In Plants: The GUS Gene Fusion System.

Jones, R. A. 1978. *Biochem. Genet*. 16:27. Effects Of Floury-2 Locus On Zein Accumulation And RNA Metabolism During Maize Endosperm Development.

Jones, R. A., Larkins, B. A., Tsai, C. Y. 1977. *Plant Physiol*. 59:525. Storage Protein Synthesis In Maize II. Reduced Synthesis Of A Major Zein Component By The Opaque-2 Mutant Of Maize.

Jones, B. N. and Gilligan, J. P. 1983. Journal of Chromatography. 266:471–482 O-Phthalaldchyde Precolumn Derivatization and Reversed-Phase High-Perfornance Liquid Chromatography of Polypeptide Hydrolysates and Physiological Fluids.

Katz, E., Thompson, C. J., Hopwood, D. A. 1983. *J. Gen. Microbiol*. 129:2703–2714. Cloning and expression of the tyrosinase gene from *Streptomyces antibioticus* in *Streptomyces lividans*.

Keller, B., Schmid, J., and Lamb, C. J. 1989. *EMBO J*. 8:1309–1314. Vascular Expression Of A Bean Cell Wall Glycine-Rich Protein: β-Glucuronidase Gene Fusion In Transgenic Tobacco.

Kirihara, J. A., Hunsperger, J. P., Mahoney, W. C., Messing, J. 1988. *Mol. Gen. Genet*. 211:477–484.

Lawton, M. A., Tierney, M. A., Nakamura, I., Anderson, E., Komeda, Y., Dube, P., Hoffman, N., Fraley, R. T., Beachy, R. N. 1987. *Plant Molecular Biology*. 9:315–324. Expression of a soybean β-conclycinin gene under the control of the Cauliflower Mosaic Virus 35S and 19S promoters in transformed petunia tissues.

Lending, C. R. and Larkins, B. A. 1989. *Plant Cell*. 1:1011–1023. Changes in the Zein Composition of Protein Bodies during Maize Endosperm Development.

Lopes, M. A. and Larkins, B. A. 1993. *Plant Cell*. 5:1383–1399. Endosperm Origin, Development And Function.

Lopes, M. A. and Larkins, B. A. 1991. *Crop Science*. 31:1655–1662. Gamma-Zein Content Is Related to Endosperm Modification in Quality Protein Maize.

Matzke, M. A. and Matzke, A. J. M. 1995. *Plant Physio*. 107:679–685. How And Why Do Plants Inactivate Homologous (Trans)Genes?

McCabe, D. E., Swain, W. F., Martinell, B. J., Christou, P. 1988. *Bio/Technology*. 6:923–926. Stable Transformation Of Soybean (Glycine Max) By Particle Acceleration.

McElroy, D., Zhang, W., Cao, J., & Wu, R. 1990. *The Plant Cell*. 2:163–171, Isolation of an Efficient Actin Promoter for Use in Rice Transformation.

Mertz, E. T., Bates, L. S., and Nelson, O. E. 1964. *Science*. 145:279–280. Mutant gene that changes protein composition and increases lysine content of maize endosperms.

Messing, J., Geraghty, D., Heidecker, G., Hu, N.-T., Kridl, J., Rubenstein, I. 1983. in *Genetic Engineering of Plants*, Kosuge, T. Meredith, C. P., and Hollaender, A., eds. Plenum Press, NY. 211–227. Plant Gene Structure.

Misra, P. S., Jambunathan, R., Mertz, E. T., Glover, D. V., Barbosa, H. M., McWhirter, K.S. 1972. *Science*. 176:1425. Endosperm Protein Synthesis In Maize Mutants With Increased Lysine Content.

Murakami, T., Anzai, H., Imai, S., Satoh, A., Nagaoka, K., Thompson, C.J. 1986. *Mol Gen. Genet*. 205:42–50. The bialaphos biosynthetic genes of *Streptomyces hygroscopicus*: Molecular cloning and characterization of the gene cluster.

Murashige, T. and Skoog, F. 1962. *Physiol. Plant*. 15:473–497. A Revised Medium For Rapid Growth And Bioassays With Tobacco Tissue Cultures.

Napoli, C., Lemieux, C., Jorgensen, R. 1990. *Plant Cell*. 2:279–289. Introduction of a Chimeric Chalcone Synthase Gene into Petunia Results in Reversible Co-Suppression of Homologous Genes in trans.

Niedz et al. 1995. *Plant Cell Reports*. 14:403.

Odell, J. T., Nagy, F., Chua, N. H. 1985. *Nature*. 313:810–812. Identification of DNA sequences required for activity of the cauliflower mosaic virus 35S promoter.

Ow, D. W., Wood, K. V., DeLuca, M., deWet, J. R., Helinski, D. R., Howell, S. H. 1986. *Science*. 234:856–859.

Paulis et al. 1978. *Cereal Chem*. 55:705 Origin Of High Methionine Content In Sugary-I Corn Endosperm.

Pedersen, K., Argos, P., Naravana, S. V. L., Larkins, B.A. 1986. J. Biol Chem. 261:6279–6284 Sequence Analysis And Characterization Of A Maize Gene Encoding A High-Sulfur Zein Protein Of M-15,000.

Peterson, G. L. 1979. *Analytical Biochemistry*. 100:291–220.

Potrykus, I., Saul, M. W., Petruska, J., Paszkowski, J., Shillito, R. D. 1985. *Mol. Gen. Genet*. 199:183–188. Direct gene transfer to cells of a graminaceous monocot.

Potrykus I. 1989. *Trends Biotech*. 7:269–273.

Prasher et al. 1985. *Biochem. Biophys. Res. Comm*. 126:1259–1268.

Rodermel, S. R., Abbott, M. S., Bogorad, L. 1988. *Cell*. 55:673–681. Nuclear-Organelle Relationships: Nuclear Antisense Gene Inhibits Ribulose Bisphosphate Carboxylase Enzyme Levels In Transformed Tobacco Plants.

Rubenstein, J. L. R. 1982. in *Maize for Biological Research*, W. F. Sheridan, ed., U. of N. Dakota Press. pp. 189–196. The Zein Multigene Family.

Sambrook, J., Fritsch, E. F., and Maniatis, T. 1989. Molecular Cloning: A Laboratory Manual. Second Edition (Cold Spring Harbor, NY: Cold Spring Harbor Press).

Sengupta-Gopalan, C., Reichert, N. A., Barker, R. F., Hall, T. C., Kemp, J. D. 1985. *Proc. Natl. Acad. Sci. USA*. 83:3320–3324 Developmentally regulated expression of the bean β-phaseolin gene in tobacco seed.

Stalker, D. M., McBride, K. E., and Malyj, L. 1988. *Science*. 242:419–423. Herbicide Resistance in Transgenic Plants Expressing a Bacterial Detoxification Gene.

Stiefel, V., Ruiz-Avila, L., Raz, R., Valles, M. P., Gomez, J., Pages, M., Martinez-Izquierdo, J. A., Ludevid, M.D., Langdale, J. A., Nelson, T., and Puigdomenech, P. 1990. *The Plant Cell*. 2:785–793. Expression Of A Maize Cell Wall Hydroxyproline-Rich Glycoprotein Gene In Early Leaf And Root Vascular Differentiation.

Sullivan, T. D., Christensen, A. H., and Quail, P. H. 1989. *Mol. Gen. Genet*. 215:431 Isolation and characterization of a maize chlorophyll a/b binding protein gene that produces high levels of mRNA in the dark.

Sutcliffe, J. G. 1978. *Proc. Natl. Acad. Sci. USA*. 75:3737–3741. Nucleotide sequence of the ampicillin resistance gene of *Escherichia coli* plasmid pBR322.

Thillet, J., Absil, J., Stone, S. R., & Pictet, R. 1988. *J Biol. Chem*. 263:12500–12508. Site-directed Mutagenesis of Mouse Dihydrofolate Reductase.

Tsai, C. Y. 1980. *Cereal Chem*. 57:288–290. Note On The Effect Of Reducing Agent On Zein Preparation.

Tsai et al. 1978. *Biochen. Genet*. 16:883. Interaction Of The Opaque-2 Gene With Starch-Forning Mutant Genes On The Synthesis Of Zein In Maize Endosperm.

Twell, D., Klein, T. M., Fromm, M. E., and McCormick, S. 1989. *Plant Physiol*. 91:1270–1274. Transient Expression Of Chimeric Genes Delivered Into Pollen By Microprojectile Bombardment.

van der Krol, A. R., Lenting, P. E., Veenstra, J., van der Meer, I. M., Koes, R. E., Gerats, A. G. M., Mol, J. N. M. and Stuitje, A. R. 1988c. *Nature*. 333:866–869. An antisense chalcone synthase gene in transgenic plants inhibits flower pigmentation.

van der Krol, A. R., Mol, J. N. M. & Stuitje, A. R. 1988a. *Biotechniques*. 6:958–976. Regulation Of Eukaryotic Gene Expression By Complementary RNA Or DNA Sequences: An Overview.

van der Krol, A. R., Mol, J. N. M. & Stuitje, A. R. 1988b. *Gene*. 72:45. Antisense Genes In Plants: An Overview.

Walker, J. C., Howard, E. A., Dennis, E. S., and Peacock, W. J. 1987. *Proc. Natl Acad. Sci. USA*. 84:6624–6628. DNA Sequences Required For Anaerobic Expression Of The Maize Alcohol Dehydrogenase 1 Gene.

Walters, D. A., Vetsch, C. S., Potts, D. E., & Lundquist, R. C. 1992. *Plant Molecular Biology*. 18:189–200. Transformation and inheritance of a hygromycin phosphotransferase gene in maize plants.

Wang et al. 1992. *Mol. Cell. Biol*. 12:3399.

Yang, N.-S. and Russell, D. 1990. *Proc. Natl. Acad. Sci. USA*. 87:4144–4148. Maize Sucrose Synthase-1 Promoter Directs Phloem Cell-Specific Expression Of Gus Gene In Transgenic Tobacco Plants.

Zukowsky-. 1983. *Proc. Natl. Acad. Sci. USA*. 80:1101.

What is claimed:

1. A method for inhibiting the expression of a maize seed storage protein in a maize seed which comprises:

a) stably transforming maize cells with an expression cassette comprising a preselected DNA sequence operably linked to a promoter functional in a maize cell and that encodes an RNA molecule so as to yield transformed cells, wherein the RNA molecule is substantially complementary to all or a portion of a messenger RNA which encodes a maize seed storage protein; and b) regenerating the transformed cells into a fertile transgenic plant which generates maize seeds, wherein the preselected DNA sequence is expressed in the seed in an amount effective to substantially reduce expression of the maize seed storagce protein.

2. The method of claim 1, wherein said reduced expression of the seed storage protein results in an increase in the seed of an amount of at least one amino acid which is essential to the diet of animals.

3. A method for inhibiting expression of a family of maize seed storage protein genes in a maize seed, which comprises:

a) stably transforming maize cells with a first preselected DNA sequence operably linked to a promoter functional in maize and which encodes a RNA molecule so as to yield transformed cells, wherein the first preselected DNA sequence encodes an RNA molecule which is substantially complementary to a region of conserved homology in the family of maize seed storage proteins; and b) regenerating the transformed cells into a fertile transgenic plant which yields transgenic seed, wherein the preselected DNA sequence is expressed in the seed in an amount effective to substantially reduce expression of seed storage proteins in the transgenic seed relative to the expression of the family of seed storage proteins in a corresponding nontransgenic seed.

4. A method for increasing the amount of at least one amino acid essential to the diet of animals in a maize seed, which comprises:

a) stably transforming maize cells with a first preselected DNA sequence and a second preselected DNA sequence so as to yield transformed cells, wherein the first preselected DNA sequence encodes a RNA molecule substantially complementary to all or a portion of a messenger RNA encoding a maize seed storage protein, wherein the second preselected DNA sequence encodes a polypeptide having at least one amino acid essential to the diet of animals, and wherein each preselected DNA sequence is operably linked to a promoter functional in maize; and b) regenerating the transformed cell into a fertile transgenic plant which yields transgenic seeds, wherein the first preselected DNA sequence is expressed in an amount effective to substantially reduce the production of said seed storage protein in said transgenic seed relative to the amount of said seed storage protein present in the corresponding nontransgenic seed, and wherein the second preselected DNA sequence is expressed in an amount sufficient to increase the amount of the at least one essential amino acid in said transgenic seed relative to the amount of said essential amino acid present in the corresponding nontransgenic seed.

5. A method for altering the protein composition in a seed, which comprises:

a) stably transforming maize cells with a first preselected DNA sequence and a second preselected DNA sequence so as to yield transformed cells, wherein the first preselected DNA sequence encodes an RNA molecule substantially complementary to all or a portion of at least one messenger RNA encoding a maize seed storage protein, wherein the second preselected DNA molecule encodes a protein, and wherein each preselected DNA sequence is operably linked to a promoter functional in said cells; and b) regenerating the transformed cells into a fertile transgenic plant which produces transgenic seed, wherein the first preselected DNA sequence is expressed in the transgenic seed in an amount effective to substantially reduce the production of the seed storage protein relative to the amount of said seed storage protein present in the corresponding nontransgenic seed, and wherein the second preselected DNA sequence is expressed in said transgenic seed as a protein in a amount which is substantially increased over the amount of that protein in the corresponding nontransgenic seed.

6. A method for inhibiting the expression of a maize seed storage protein in a maize seed which comprises:

a) stably transforming maize cells with an expression cassette comprising a preselected DNA sequence encoding an RNA molecule operably linked to a promoter functional in maize cells so as to yield transformed cells, wherein the RNA molecule is substantially identical to all or a portion of a messenger RNA for the maize seed storage protein; and b) regenera ting the transf ormed cells into a fertile transgenic plant which generates maize seed, wherein the preselected DNA sequence is expressed in the seed in an amount effective to substantially reduce expression of the maize seed storage protein.

7. The method of claim 1, wherein said reduced expression of the seed storage protein results in an increase in the seed of an amount of at least one amino acid which is essential to the diet of animals.

8. A method for inhibiting expression of a family of maize seed storage protein genes in a maize seed, which comprises:

a) stably transforming maize cells with a first preselected DNA sequence operably linked to a promoter functional in maize cells which encodes a RNA molecule so as to yield transformed cells, wherein the first preselected DNA sequence encodes an RNA molecule which is substantially identical to a region of conserved homology in the family of maize seed storage proteins; and b) regenerating the transformed cells into a fertile transgenic plant which yields transgenic seed, wherein the preselected DNA sequence is expressed in the seed in an amount effective to substantially reduce expression of seed storage proteins in the transgenic seed relative to the expression of the family of seed storage proteins in a corresponding nontransgenic seed.

9. A method for increasing the amount of at least one amino acid essential to the diet of animals in a maize seed, which comprises:

a) stably transforming maize cells with a first preselected DNA sequence and a second preselected DNA sequence so as to yield transformed cells, wherein the first preselected DNA sequence encodes a RNA molecule substantially identical to all or a portion of a messenger RNA encoding a maize seed storage protein, wherein the second preselected DNA sequence encodes a polypeptide having at least one amino acid essential to the diet of animals, and wherein each preselected DNA sequence is operably linked to a promoter functional in maize cells; and b) rege nerating the transformed cell into a fertile transgenic plant which yields transgenic seed, wherein the first preselected DNA sequence is expressed in an amount effective to substantially reduce the production of said seed storage protein in said transgenic seed relative to the amount of said seed storage protein present in the corresponding nontransgenic seed, and wherein the second preselected DNA sequence is expressed in an amount sufficient to increase the amount of the at least one essential amino acid in said transgenic seed relative to the amount of said essential amino acid present in the corresponding nontransgenic seed.

10. A method for altering the protein composition in a seed, which comprises:

a) stably transforming maize cells with a first preselected DNA sequence and a second preselected DNA sequence so as to yield transformed cells, wherein the first preselected DNA sequence encodes an RNA molecule substantially identical to all or a portion of at least one messenger RNA encoding a maize seed storage protein, wherein the second preselected DNA molecule encodes a protein, and wherein each preselected DNA sequence is operably linked to a promoter functional in maize; and b) regenerating the transformed cells into a fertile transgenic plant which produces transgenic seed, wherein the first preselected DNA sequence is expressed in the transgenic seed in an amount effective to substantially reduce the production of the seed storage protein relative to the amount of said seed storage protein present in the corresponding nontransgenic seed, and wherein the second preselected DNA sequence is expressed in said transgenic seed as a protein in a amount which is substantially increased over the amount of that protein in the corresponding nontransgenic seed.

11. The method as in one of claims 1–10, wherein said seed storage protein is an α-zein protein.

12. The method of claim 1, 2, 6, or 7, in which the seed of the transgenic plant has an increased amount of at least one essential amino acid.

13. The method of claim 12, wherein the essential amino acid is selected from the group consisting of methionine, threonine, lysine, tryptophan, and isoleucine.

14. The method of claim 4 or 9, wherein the essential amino acid is selected from the group consisting of methionine, threonine, lysine, tryptophan, and isoleucine.

15. The method of claim 12, wherein the amount of the amino acid in the seed is increased at least about 50% to 300%.

16. The method of claim 4 or 9, wherein the amount of the amino acid in the seed is increased at least about 50% to 300%.

17. The method as in one of claims 1–10, wherein the preselected DNA sequence is operably linked to a promoter functional during plant seed development.

18. The method as in one of claims 1–10, wherein the promoter comprises the 10 kD zein promoter.

19. The method as in one of claims 1–10, wherein the promoter comprises the 27 kD zein promoter.

20. The method as in one of claims 1–10, wherein said seed storage protein is a 19 kD α-zein protein.

21. The method as in one of claims 1–10, wherein said seed storage protein is a 22 kD α-zein protein.

22. The method as in one of claims 4, 5, 9, and 10, wherein the second preselected DNA sequence encodes a prolamine.

23. The method as in one claims 1–10, which further comprses transforming the cells with at least one selectable marker gene.

24. The method of claim 12 further comprising breeding the fertile transgenic plant to yield a progeny plant that has an increase in the amount of at least one amino acid as a dominant trait.

25. The method as in one of claims 1–10, further comprising recovering the transgenic seed.

26. The method of claim 3 or 8, wherein the protein is substantially homologous in α-zein proteins.

27. The method of claim 4, 5, 9, or 10, wherein the second preselected DNA sequence encodes MB1.

28. The method of claim 4, 5, 9, or 10, wherein the second preselected DNA sequence encodes a 10 kD zein.

29. The method of claim 4, 5, 9, or 10, wherein the cells are transformed with a third preselected DNA sequence which encodes a prolamine.

30. The method of claim 29, wherein the third preselected DNA sequence encodes a 27 kD zein protein.

31. The method of claim 3 or 6 wherein the cells are transformed with a second preselected DNA sequence which encodes a prolamine.

32. The method of claim 31 wherein the second preselected DNA sequence encodes a 27 kD zein protein.

33. The method of claim 4 or 9 further comprising breeding the fertile transgenic plant to yield a progeny plant that has an increase in the amount of at least one amino acid as a dominant trait.

34. The method of claims 22, 29, 31, or 32, wherein the prolamine is a zein.

* * * * *

UNITED STATES PATENT AND TRADEMARK OFFICE
CERTIFICATE OF CORRECTION

PATENT NO. : 6,326,527 B1  
DATED : December 4, 2001  
INVENTOR(S) : Kirihara et al.

It is certified that error appears in the above-identified patent and that said Letters Patent is hereby corrected as shown below:

Title page,  
Item [57], ABSTRACT,  
Line 7, please delete "an" after "with".

Column 14,  
Line 23, please delete "3.3" and insert -- 3. 3' -- therefore.

Column 55,  
Line 12, please delete "storagce" and insert -- storage -- therefor.

Column 56,  
Line 27, please delete "regenerat ing" and insert -- regenerating -- therefor.  
Line 27, please delete "transf ormed" should read -- transformed --.

Column 57,  
Line 1, please delete "rege nerating" and insert -- regenerating --  
Line 35, please delete "a amount" and insert -- an amount --

Column 58,  
Line 18, please insert -- of -- between "one" and "claims".  
Line 47, please delete "32" and insert -- 33 -- therefor.

Signed and Sealed this

Ninth Day of September, 2003

JAMES E. ROGAN  
*Director of the United States Patent and Trademark Office*